US011285204B2

(12) United States Patent
Dutta et al.

(10) Patent No.: US 11,285,204 B2

(45) Date of Patent: Mar. 29, 2022

(54) TOBAMOVIRUS-BASED VIRUS-LIKE PARTICLES AND VACCINES

(71) Applicant: Government of the United States, as represented by the Secretary of the Army, Fort Detrick, MD (US)

(72) Inventors: Sheetij Dutta, Silver Spring, MD (US); Adrian Batchelor, Baltimore, MD (US); Farhat Khan, Columbia, MD (US); Mark Langowski, Vienna, VA (US)

(73) Assignee: THE GOVERNMENT OF THE UNITED STATES, AS REPRESEN, Fort Detrick, MD (US)

( * ) Notice: Subject to any disclaimer, the term of this patent is extended or adjusted under 35 U.S.C. 154(b) by 0 days.

(21) Appl. No.: 16/649,567

(22) PCT Filed: Sep. 21, 2018

(86) PCT No.: PCT/US2018/052193

§ 371 (c)(1),
(2) Date: Mar. 20, 2020

(87) PCT Pub. No.: WO2019/060703

PCT Pub. Date: Mar. 28, 2019

(65) Prior Publication Data

US 2020/0368341 A1 Nov. 26, 2020

Related U.S. Application Data

(60) Provisional application No. 62/561,956, filed on Sep. 22, 2017.

(51) Int. Cl.

*A61K 39/12* (2006.01)
*A61K 39/015* (2006.01)
*A61K 39/00* (2006.01)

(52) U.S. Cl.

CPC ............ *A61K 39/12* (2013.01); *A61K 39/015* (2013.01); *A61K 2039/5258* (2013.01); *A61K 2039/6075* (2013.01); *A61K 2039/64* (2013.01)

(58) Field of Classification Search

None
See application file for complete search history.

(56) References Cited

U.S. PATENT DOCUMENTS

2003/0118596 A1 6/2003 Pogue et al.
2009/0117144 A1 5/2009 Rasochova et al.

OTHER PUBLICATIONS

Letschert et al., Journal of Virological Methods, 2002, 106:1-10. (Year: 2002).*

Bruckman et al., ACS Nano, 2011, 5(3):1606-1616. (Year: 2011).*

McCormick et al., Expert Rev. Vaccines, 2008, 7(1):33-41. (Year: 2008).*

International Preliminary Report on Patentability for PCT/US2018/052193 dated Apr. 2, 2020.

UniProtKB_Q80P12, Capsid protein. UniProtKB Accession No. Q80P12. Last Sequence 4 Update: Jun. 1, 2003.

Yin et al., Tobacco Mosaic Virus as a New Carrier for Tumor Associated Carbohydrate Antigens Bioconjug Chem. 2012, vol. 23(8), p. 1694-1703.

Davies DR, Sheriff S, Padlan EA. Antibody-antigen complexes. J Biol Chem. 1988, 263: 10541-10544.2.

Macraild CA, Zachrdla M, Andrew D, Krishnarjuna B, Novacek J, Zidek L, Sklenar V, Richards JS, Beeson JG, Anders RF, Norton RS. Conformational dynamics and antigenicity in the disordered malaria antigen merozoite surface protein 2. PLoS One. 2015, 10: be01 19899.

Neafsey DE, Juraska M, Bedford T, Benkeser D, Valim C, et al. Genetic Diversity and Protective Efficacy of the RTS,S/AS01 Malaria Vaccine. N Engl J Med. 2015, 373: 2025-2037.3.

Kaba SA, McCoy ME, Doll TA, Brando C, Guo Q, et al. Protective antibody and CD8+ T-cell responses to the Plasmodium falciparum circumsporozoite protein induced by a nanoparticle vaccine. PLoS One. 2012, 7(10): e48304.4.

White MT, Bejon P, Olotu A, Griffin JT, Riley EM, et al. The relationship between RTS,S vaccine-induced antibodies, CD4(+) T cell responses and protection against Plasmodium falciparum infection. PLoS One. 2013, 8: e61395.

Espinosa DA, Gutierrez GM, Rojas-Lopez M, Noe AR, Shi L, Tse SW, Sinnis P, Zavala F., Proteolytic cleavage of the Plasmodium falciparum circumsporozoite protein is a target of protective antibodies. The Journal of infectious diseases. 2015, 212(7): 1111-1119.

Zhao L, Seth A, Wibowo N, Zhao CX, Mitter N, Yu C, Middelberg AP. Nanoparticle vaccines. Vaccine. 2014, 32(3): 327-337.

Dedeo MT, Duderstadt KE, Berger JM, Francis MB: Nanoscale protein assemblies from a circular permutant of the tobacco mosaic virus. Nano Lett. 2010, 10:181-186.

Porter MD, Nicki J, Pool CD, DeBot M, Illam RM, Brando C, Bozick B, De La Vega P, Angra D, Spaccapelo R, et al: Transgenic parasites stably expressing full-length Plasmodium falciparum circumsporozoite protein as a model for vaccine downselection in mice using sterile protection as an endpoint. Clin Vaccine Immunol. 2013, 20: 803-810.

Tan J, Sack BK, Oyen D, Zenklusen I, Piccoli L, Barbieri S, Foglierini M, Fregni CS, Marcandalli J, Jongo S, Abdulla S. A public antibody lineage that potently inhibits malaria infection through dual binding to the circumsporozoite protein Nature Medicine. 2018, 24(4): 401-407.

(Continued)

*Primary Examiner* — Stacy B Chen

(74) *Attorney, Agent, or Firm* — McBee Moore & Vanik, IP, LLC

(57) ABSTRACT

The disclosure generally provides recombinant proteins comprising Tobamovirus capsid proteins and an immunogenic epitope of an antigen of interest. The recombinant protein can be used to assemble an array comprising a plurality of associated recombinant proteins that can enhance the immunogenicity of the epitope and induce and/or enhance an immune response to the antigen. The disclosure also provides compositions, such as vaccines, that include the recombinant protein as well as methods for inducing and/or enhancing an immune response in a mammal.

20 Claims, 29 Drawing Sheets

Specification includes a Sequence Listing.

(56) References Cited

OTHER PUBLICATIONS

Kisalu NK, Idris AH, Weidle C, Flores-Garcia Y, Flynn BJ, Sack BK, Murphy S, Schon A, Freire E, Francica JR, Miller AB. A human monoclonal antibody prevents malaria infection by targeting a new site of vulnerability on the parasite. Nature Medicine. 2018, 24(4): 408-416.

Oyen D, Torres JL, Wille-Reece U, Ockenhouse CF, Emerling D, Glanville J, Volkmuth W, Flores-Garcia Y, Zavala F, Ward AB, King CR. Structural basis for antibody recognition of the NANP repeats in Plasmodium falciparum circumsporozoite protein. Proceedings of the National Academy of Sciences. Nov. 14, 2017: 201715812.

Triller G, Scally SW, Costa G, Pissarev M, Kreschel C, Bosch A, Marois E, Sack BK, Murugan R, Salman AM, Janse CJ. Natural parasite exposure induces protective human anti-malarial antibodies. Immunity. 2017, 47(6) 1197-1209.

Collins KA, Snaith R, Cottingham MG, Gilbert SC, Hill AVS: Enhancing protective immunity to malaria with a highly immunogenic virus-like particle vaccine. Sci. Rep 2017, 7: 46621.

Kim DE, Chivian D, Baker D: Protein structure prediction and analysis using the Robetta server. Nucleic Acids Res. 2004, 32: W526-531.

Schwenk R, DeBot M, Porter M, Nikki J, Rein L, Spaccapelo R, Crisanti A, Wightman PD, Ockenhouse CF, Dutta S: IgG2 antibodies against a clinical grade Plasmodium falciparum CSP vaccine antigen associate with protection against transgenic sporozoite challenge in mice. PLoS One. 2014, 9: el 11020.

Wang H, Planchart A, Stubbs G. Caspar carboxylates: the structural basis of tobamovirus disassembly. Biophysical Journal. 1998, 74(I): 633-8.

Lu B., Stubbs G, Culver JN. Carboxylate interactions involved in the disassembly of tobacco mosaic tobamovirus. Virology. 1996, 225: 11-20.

Bendahmane M, Koo M, Karrer E, Beachy RN. Display of epitopes on the surface of tobacco mosaic virus: impact of charge and isoelectric point of the epitope on virus-host interactions! Journal of molecular biology. 1999, 290: 9-20.

Zhang YB, Howitt J, McCorkle S, Lawrence P, Springer K, Freimuth P. Protein aggregation during overexpression limited by peptide extensions with large net negative charge Protein expression and purification. 2004, 36(2): 207-16.

Qari SH, Goldman IF, Povoa MM, di Santi S, Alpers MP, Lai AA. Polymorphism in the circumsporozoite protein of the human malaria parasite Plasmodium vivax. Molecular and Biochemical Parasitology. 1992, 55(1-2): 105-13.

RTS,S CTP, Agnandji ST, Lell B, Fernandes JF, Abossolo BP, Methogo BG, Kabwende AL, Adegnika AA, Mordmuller B, Issifou S, et al.: A phase 3 trial of RTS,S/AS01 malaria vaccine in African infants. N Engl J Med. 2012, 367: 2284-2295.

PCT International Search Report and Written Opinion for PCT Patent Application No. PCT/US2018/052193 dated Jan. 15, 2019. 14 pages.

UniProtKB_Q80P12, Capsid Protein. UniProtKB Accession No. Q80P12 Last Sequence Updated: Jun. 1, 2003. Retrieved from the Internet. https:/www.uniprot.org/uniprot/Q80P12.

Yin et al., Tobacco Mosaic Virus as a New Carrier for Tumor Associated Carbohydrate Antigens. Bioconjug Chem 2012,vol. 23(8), p. 1694-703.

* cited by examiner

FIG. 1A
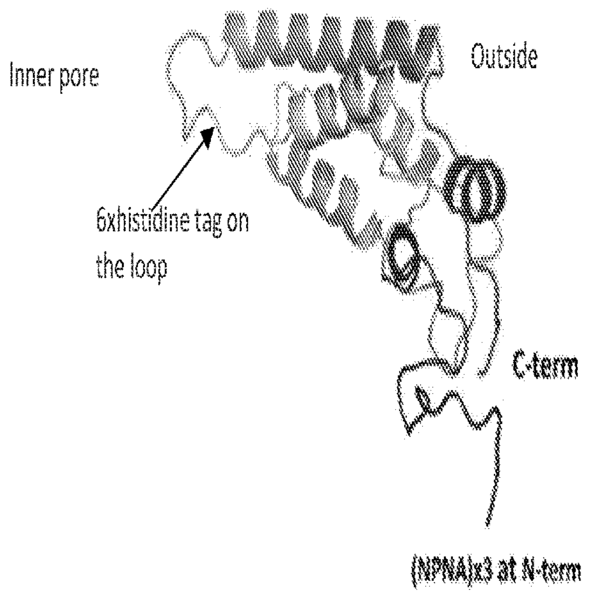
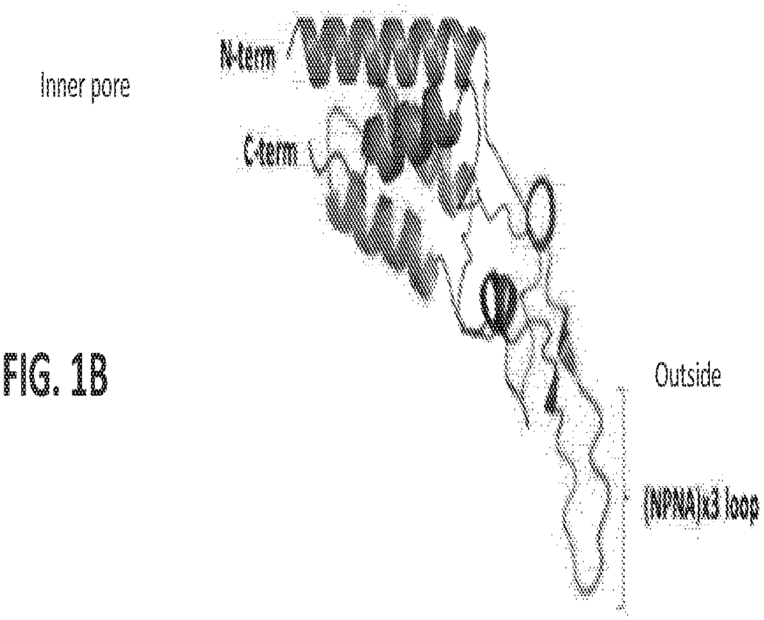
FIG. 1B

FIG. 2A
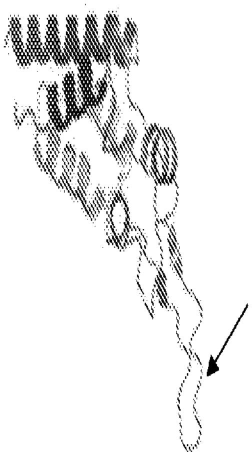
(NPNA)x3
FIG. 2B
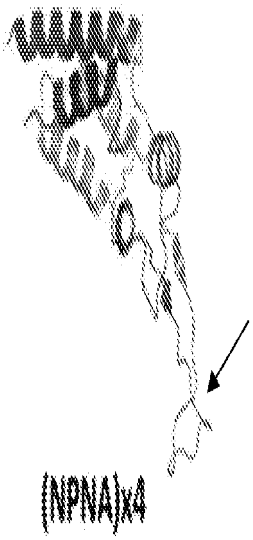
(NPNA)x4
FIG. 2C
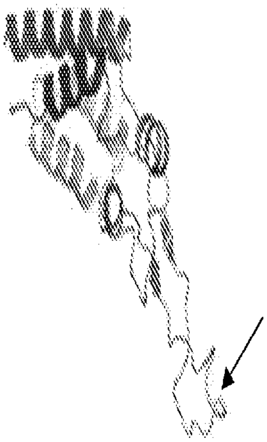
(NPNA)x5
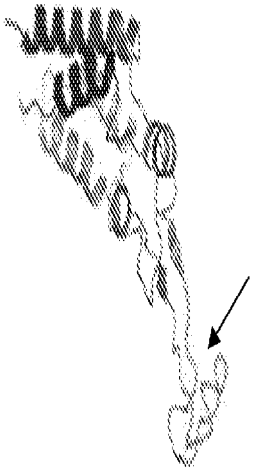
(NPNA)x7
FIG. 2D
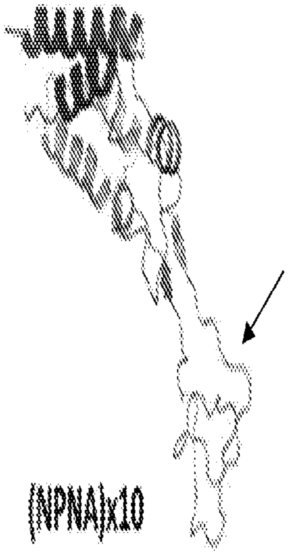
(NPNA)x10
FIG. 2E
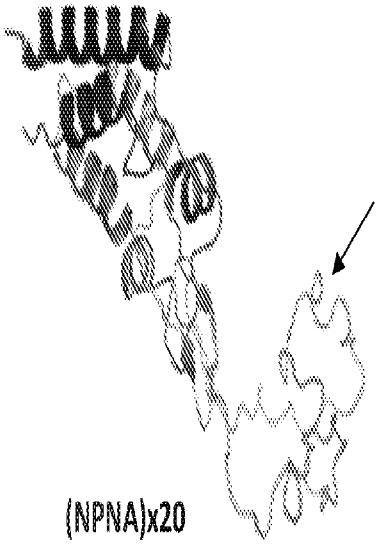
(NPNA)x20
FIG. 2F FIG. 3A
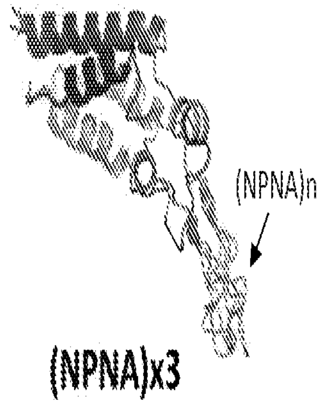
FIG. 3B
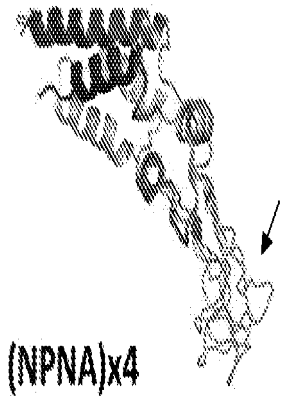
FIG. 3C
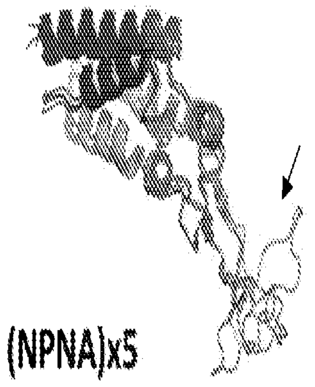
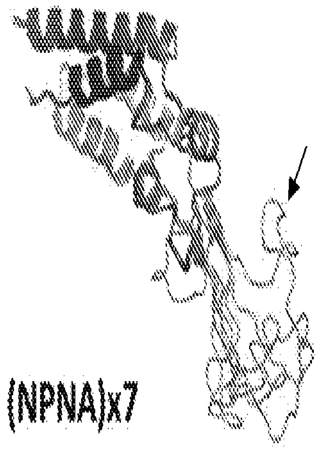
FIG. 3D
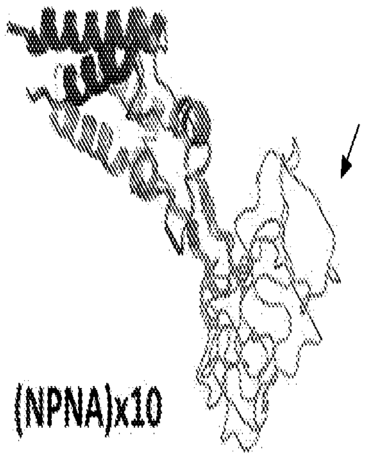
FIG. 3E (NPNA)x5 loop (NPNA)x5 NT (NPNA)x5 CT

```
Buried/exposed      eebeeeeeebeebbeebbbeeeeebeeebeebeebebeeeeeeeeeebeeeebeeb
ZMV                 MPYSTSGIRSLPAFSKSFFPYLELYNLLITNQGAALQTQNGKDILRESLVGL
eC                   2     4   2       254  5 4 41    1        4     3
TMV                 MSYSITTPSQFVFLSSAWADPIELINLCTNALGNQFQTQQARTVVQRQFSEV
eC                      4122            24  4 4 1  4     1  1 13
Species conserved       .*        :   :  :     . .        :*:* ..  .   :

Buried/exposed      eeeebeeeeebeeeeeebbebeeeeeebeebeebeeeeeeeee
ZMV                 LSSVASPTSQFPSGVFYVWSRESRIAALIDSLFGALDSRN --- pore loop ----
eC                  4  3  21   2  36  2     4 14    6 14
TMV                 WKPSPQVTVRFPDSDFKVYRYNAVLDPLVTALLGAFDTRN --- pore loop ----
                    7 2   313  2   6  6 5 134 24 11 4 16 1
Species conserved         . .:*           :     .:  : *

Buried/exposed      eeeebeebbeebeebbeebbebbeeebbeeeeebbeebebeeeeeee
ZMV                 AVKRNDDASTAAHNDIPQILSALNEGAGVFDRASFESAFGLVWTAGSS
eC                  13       21    2            6  1    1   322   =112
TMV                 ATRRVDDATVAIRSAINNLIVELIRGTGSYNRSSFESSSGLVWTSGPA
eC                  11       31          3  4     5          321   =117
Species conserved   ...* **::.: .  :       :       .   **    .  *
```

FIG. 5

2wP3 Study 4

FIG. 16B

TMV-NPNAx5L:

MHHHHHHTRRVDDATVAIRSAINNLIVELIRGTGSYNRSSFESSS
GLVWTNPNANPNANPNANPNANPNASYSITTPSQFVFLSSAWA
DPIELINLCTNALGNQFQTQQARTVVQRQFSEVWKPSPQVTVRF
PDSDFKVYRYNAVLDPLVTALLGAFDTRN

TMV-NPNAx5-Acidic-Out:

MHHHHHHTRRVDDATVAIRSAINNLIVELIRGTGSYNRSSFESSS
GLVWTSDNPNANPNANPNANPNANPNAEGSYSITTPSQFV
FLSSAWADPIELINLCTNALGNQFQTQQARTVVQRQFSEVWKPS
PQVTVRFPDSDFKVYRYNAVLDPLVTALLGAFDTRN

TMV-NPNAx5-Acidic-In:

MHHHHHHDATRRVDDATVAIRSAINNLIVELIRGTGSYNRSSFE
SSSGLVWTNPNANPNANPNANPNANPNASYSITTPSQFVFLSSA
WADPIELINLCTNALGNQFQTQQARTVVQRQFSEVWKPSPQVT
VRFPDSDFKVYRYNAVLDPLVTALLGAFDTRNRIIE

FIG. 17D
TMV-NPNAx5-Acidic-Out
TMV-NPNAx5-Acidic-In

Ammonium
Sulfate precipitation

Q Column

TMV-NPNAx5-Acid-out

TMV-(VK247)x5

TMV-(VK247)x5

TOBAMOVIRUS-BASED VIRUS-LIKE PARTICLES AND VACCINES

PRIORITY

The present application is a National Phase Entry of PCT International Application No. PCT/US2018/052193 which was filed on Sep. 21, 2018, which claims priority to provisional patent application Ser. No. 62/561,956, filed Sep. 22, 2017, both of which are hereby incorporated by reference in their entireties.

GOVERNMENTAL RIGHTS

This invention was made with support from the United States Government and the Walter Reed Army Institute of Research. Accordingly, the United States government has certain rights in this invention. Funding for this work was provided by the US department of defense and United States Agency for International Development, Malaria Vaccine Program.

FIELD

This disclosure generally relates to recombinant proteins comprising capsid proteins from Tobamovirus and an immunogenic epitope from an antigen, compositions, vaccines, and methods of enhancing an immune response in a mammal.

BACKGROUND

While vaccines have provided a huge benefit to human health, there remains a need to develop improved vaccines and vaccine technology such as, for example, those that may provide enhanced safety and/or improve immune response against an antigen. For example, it has been shown that epitope flexibility and density significantly influence the immunogenicity of vaccines. Crystallographic studies using lysozyme it was found that the most immunogenic regions of this enzyme were the surface exposed loops, which were relatively flexible [1]. In contrast, an NMR study of an inherently disordered malaria antigen, MSP-2, demonstrated that the most flexible regions were in fact less immunogenic than structured regions [2]. It is possible that in rigid tightly folded globular proteins like lysozyme, flexible regions can adapt conformations that bind tightly to a diverse repertoire of antibody molecules on B-cell surface by an induced fit mechanism while in non-structured proteins such as MSP-2, the flexibility of some regions was too high to overcome the entropic cost of induced fit.

Structure based immunogen design is of considerable interest as it can make vaccines more effective, simpler and cheaper. One promising recombinant malaria vaccine is RTS,S (GlaxoSmithKline) that is based on the Circumsporozoite protein (CSP), that is abundantly present on the mosquito-transmissible, sporozoite, stage of *Plasmodium falciparum*. RTS,S contains the repeat and C-terminal regions of *P. falciparum* 3D7 strain CSP and it can confer 60-80% sterile protection against controlled human malaria infection (CHMI) with a homologous strain of the parasite. The efficacy of RTS,S against diverse malaria parasite populations in the field however remains below 50% [3,5]. Protection in humans has been associated with the titer and avidity of antibodies against the NPNA repeat-region of CSP [4,5], although epitopes at the N-terminal (Nterm or NT) and C-terminal regions (Cterm or CT) are also being targeted for vaccine purposes [6].

Another factor that influences immunogenicity is epitope density or epitope valency, in particular, for repeating antigenic epitopes. The packing density can be controlled by varying the number of repeating units (valency) within each molecule. While many spherical virus-like particle (VLP) systems can accommodate external peptides, there is a limit to the size of the displayed epitopes due to the steric constraints on packaging. In contrast, if there was no need for sphere closure, spiral particles may be more amenable to insertion of epitopes and structural modifications thus allowing for the display of larger epitopes without disturbing the formation of particle scaffold.

A further factor controlling immunogenicity is the size of the antigen. Soluble antigens that are <10 nm size are generally considered weakly immunogenic and often require oil emulsions, liposomes, crosslinking or conjugation to larger carrier proteins to gain immunogenicity. Virus-like particles (VLP) are 10-200 nm in size and these are highly effective in augmenting immunogenicity [7]. VLPs are readily taken up and processed by B-cells and antigen presenting cells. Many of the recombinant protein based vaccines are VLPs including GlaxoSmithKline's Engerix® (hepatitis B virus) and Cervarix® (human papillomavirus), and Merck's Recombivax HB® (hepatitis B virus) and Gardasil® (human papillomavirus).

There remains an acute need for vaccines capable of inducing an immune response profile which will protect the recipient from the spectrum of disease, e.g. malaria infection, resulting from infectious agents, and without risking the potential for reactogenicity. Moreover, there is a need to reduce complex adjuvants that contain potentially expensive and reactogenic immune modulators. Improving the immunogenicity of vaccines can assist in creating a vaccine that is highly effective toward the desired target.

SUMMARY OF THE DISCLOSURE

In one aspect the disclosure relates to a recombinant protein comprising a Tobamovirus capsid protein and an immunogenic epitope of an antigen of interest. In some embodiments, the capsid protein comprises the native amino acid sequence. In other embodiments the Tobamovirus capsid protein comprises a modified amino acid sequence to allow easy production of a vaccine in *E. coli* host. In some embodiments, the Tobamovirus capsid protein is selected from the group consisting of Tobacco mosaic virus (TMV) and zucchini green mottled mosaic virus (ZMV). In further embodiments, the capsid protein comprises SEQ ID NO: 1, SEQ ID NO: 2, SEQ ID NO: 3, or SEQ ID NO: 4.

In embodiments of this aspect, the immunogenic epitope may be derived from an antigen that induces an immune response against cells such as, for example, cancer cells; an antigen that induces an immune response against a disease (e.g., an infectious disease) that may be induced, caused, or exacerbated by a microbe (e.g., viruses, fungi, bacteria, archaea, protists, yeast, or microscopic animals); or an antigen that induces an immune response against allergens. In further embodiments, the immunogenic epitope is derived from a microbe such as a virus or bacterium. In yet further embodiments, the immunogenic epitope can be derived from a *Plasmodium* species.

In some embodiments, the recombinant protein is selected from the group consisting of: SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 23; SEQ ID NO: 24; and SEQ ID NO: 25.

In another aspect, the disclosure provides a composition comprising at least one of the recombinant proteins described herein.

In an aspect, the disclosure provides a vaccine comprising at least one of the recombinant proteins described herein, optionally with an adjuvant. In embodiments, the vaccine may comprise an array of at least one of the recombinant proteins described herein, wherein the array forms an interior pore and an external displayed epitope loop, and wherein the immunogenic epitope is displayed on the external region of the array (TMV disk).

In some embodiments of the above aspects, the immunogenic epitope comprises the amino acid sequence NPNA(n) of circumsporozoite protein (CSP) from *P. falciparum*, wherein n is an integer selected from 1 to 20, 1 to 10, and 5.

In another aspect, the disclosure relates to a method for purifying a recombinant protein as described herein, where the method comprises expressing the recombinant protein in a host cell; and isolating the recombinant protein either as soluble or insoluble protein.

In a further aspect, the disclosure provides a method of inducing an immune response in a mammal comprising administering to the mammal an effective amount of a recombinant protein as described herein, or a composition or vaccine that includes an effective amount of a recombinant protein described herein.

In a related aspect, the disclosure provides a method of enhancing immunogenicity of an amino acid antigen, where the method comprises expressing a recombinant protein that comprises the amino acid antigen and a Tobamovirus capsid protein; isolating the recombinant protein under conditions that allow the recombinant protein to assemble in an array of monomers that forms an interior region (pore) and an external region (exposed loop on a disk), wherein the amino acid antigen is displayed on the external region of the array of monomers.

In embodiments of the above aspects relating to methods, the Tobamovirus capsid protein may be selected from the group consisting of Tobacco mosaic virus (TMV) and zucchini green mottled mosaic virus (ZMV). In further embodiments, the capsid protein comprises SEQ ID NO: 1, SEQ ID NO: 2, SEQ ID NO: 3, or SEQ ID NO: 4, SEQ ID NO 21, SEQ ID NO 22.

Other aspects will be apparent to one of skill in the art upon review of the description and exemplary aspects and embodiments that follow.

BRIEF DESCRIPTION OF THE DRAWINGS

For the purpose of illustrating the disclosure, there are depicted in the drawings certain features of the aspects and embodiments of the disclosure. However, the disclosure is not limited to the precise arrangements and instrumentalities of the aspects depicted in the drawings.

FIG. 1A-1C show various conformations of TMV. The monomer is shown in FIG. 1A and FIG. 1B and the disk form is shown in FIG. 1C. FIG. 1A shows the 'native' crystal structure of the TMV monomer [8]. The N- and C-termini are on the "exposed outside" surface of the TMV particle (disk form) and a flexible loop is located within the pore. In this case the (NPNA)x3 peptide is shown linked at the N-terminus (N-term), and the loop in the inner pore has been replaced by a 6xhistidine tag. FIG. 1B shows the circular permutant or 'exposed loop' form of TMV. N-terminus and the C-terminus both point towards the center of ring or spiral pore and the exposed loop (NPNA)x3) is accessible for B-cell receptor recognition on the disk surface. FIG. 1C shows a model of the exposed loop protein displaying the (NPNA)x3 loop multimerized into a ring (based on the PDB accession #3KML crystal structure). Pictures generated using Pymol software (available at the Pymol website).

FIG. 2A-2F depict the exposed loop forms of TMV displaying (NPNA)x3 (FIG. 2A), (NPNA)x4 (FIG. 2B), (NPNA)x5 (FIG. 2C), (NPNA)x7 (FIG. 2D), (NPNA)x1 (FIG. 2E) and (NPNA)x20 (FIG. 2F) loop. Image of the backbone of the minimum energy structures were predicted by Robetta website (robetta.bakerlab.org). The arrow represents the NPNA epitope.

FIG. 3A-3E illustrate overlaid images of the backbone of the lowest 4 energy structures predicted by Robetta for TMV displaying (NPNA)x3 (FIG. 3A), (NPNA)x4 (FIG. 3B), (NPNA)x5 (FIG. 3C), (NPNA)x7 (FIG. 3D), (NPNA)x10 (FIG. 3E). The arrow represents the NPNA epitope.

FIG. 5 shows a comparison of TMV and ZMV sequences (SEQ ID NOs: 1 and 3, respectively). Alignment of sequences in the native form with the flexible pore loop deleted. 'e' and 'b' indicate exposed and buried residues. eC is the number of surf ace exposed carbons determined manually by examining the TMV structure or the predicted ZMV structure. Total eC count was 117 for TMV and 112 for ZMV.

FIG. 6A shows coomassie blue stained reduced gels of purification of NPNAx5, 7, 10 and 20 displaying TMV particles over Ni-NTA chromatography (Step 1), Q-Sepharose chromatography (Step 2) and the final refolding that results in the particles (Step 3). FIG. 6B shows purified products for NPNAx5-NT, NPNAx5-CT and NPNAx5-L analyzed by reduced SDS-PAGE. FIG. 6C shows Coomassie blue stained particles analyzed by SDS-PAGE (left) and Western blot (right) with anti-CSP mouse polyclonal serum.

FIG. 8A Constructs showing the GST fusion proteins representing the N-terminal, the (NPNA)n repeat region (Rep) or the C-terminal region (Cter) of CSP expressed in *E. coli*. FIG. 8B Mice were vaccinated with these proteins and analyzed for antibody titers by ELISA at 2 weeks post $3^{rd}$ dose (2WP3) and for protection by challenging with transgenic *P. falciparum* gene carrying rodent *P. berghei* parasites [9]. FIG. 8C Percentage of mice (y axis) that exhibited sterile protection (no blood stage parasites detected) over the 2 week follow up period (x axis) after parasite challenge. FIG. 8D Results of an in vitro liver invasion assay confirmed that only the repeat region antibodies present in the positive control mAb 2A10, FLCSP (1:100 diluted serum) or Repeat containing GST fusion protein serum could inhibit parasite burden in liver cells by at least 2× log (dotted line) compared to the pre-immune control serum.

FIG. 9A NANP peptide ELISA data at 2 weeks post $3^{rd}$ vaccine (2WP3) (mean and SE). FIG. 9B Percentage of mice (y axis) that exhibited sterile protection over the 2 week follow up period (x axis) after parasite challenge.

FIG. 10A NANP ELISA data at 2 weeks post $3^{rd}$ vaccine (2WP3) (mean and SE). FIG. 10B Percentage of mice (y axis) that exhibited sterile protection over the 2 week follow up period (x axis) after parasite challenge.

FIG. 11A Repeat peptide ELISA data at 2 weeks post $3^{rd}$ vaccine (2WP3) (mean and SE). FIG. 11B Percentage of mice (y axis) that exhibited sterile protection over the 2 week follow up period (x axis) after parasite challenge.

FIG. 12A Study 5, repeat peptide specific titers of individual C57BL/6 mice immunized with 2.5 μg CSP and TMV-NPNAx5 in Liposome+3DPHAD+QS21 containing adjuvant (ALF-Q) at 2 weeks post $3^{rd}$ dose (2WP3). FIG. 12B Survival curves of immunized C57BL/6 mice shown in FIG. 12A (study-5) at 14 days after challenge with transgenic *P. berghei* expressing full-length PfCSP. FIG. 12C Study 6, NANP titers of C57BL/6 mice immunized with 2.5 TMV-NPNAx5, -NPNAx7, -NPNAx10, and -NPNAx20 formulated in Liposome+3DPHAD+QS21 adjuvant 2 weeks post $3^{rd}$ dose. FIG. 12D Survival curves of immunized C57BL/6 mice in Study-6 over 14 days after challenge with transgenic *P. berghei* expressing full-length PfCSP.

FIG. 13A Outline of Rhesus (Indian Origin) immunization study design. Three doses formulated in a Liposomal adjuvant ALF-Q containing 3DPHAD (Avanti Polar Lipids) and QS21 (Desert King) containing TMV construct were given 1 month apart and ELISA performed to compare immunogenicity at 2 weeks post $3^{rd}$ dose (2WP3). FIG. 13B Repeat titers of Rhesus monkeys at 2 weeks post $3^{rd}$ vaccination (2WP3). *indicate statistically significant differences. Numbers within each bar is the group mean. FIG. 13C Avidity index of Rhesus monkeys at 2 weeks post $3^{rd}$ immunization. * represents statistically significant difference. Numbers in blue within each bar represent the group mean.

FIG. 15A Competition ELISA was performed using serum from one mouse vaccinated with CSP, TMV-NPNAx5 and an unvaccinated negative control. FIG. 15B Antibody secreting cells generated by TMV vaccines. ELISPOT was performed using cells isolated from bone marrow or spleen. FIG. 15C Mean ratio of IgG2c and IgG1 titers determined for individual mice.

FIG. 16A-16B depicts information on constructs. FIG. 16A TMV-NPNAx5L Robetta predicted structure (image generated in PyMOL) and arrows showing the location of the amino acid insertions/additions to the TMV monomer. FIG. 16B Amino acid sequences of TMV-NPNAx5 constructs where the acidic residues were inserted/restored shown in large font. TMV-NPNAx5L (SEQ ID NO: 7), TMV-NPNAx5-Acidic-Out (SEQ ID NO: 19) and TMV-NPNAx5-Acidic-In (SEQ ID NO: 20) sequences.

FIG. 17A-17D shows data on expression and purification of constructs containing the additional acidic residues under denaturing conditions. FIG. 17A) Localization of TMV NPNAx5 variants in pellet (insoluble) or supernatant (soluble) fraction. FIG. 17B Ni-NTA purification under denaturing (7M Urea) conditions; M=Marker (SeeBlue 2), L=Load, FT=Flow-Through fraction, W=Wash, E=Elution. FIG. 17C Q-column purification under denaturing conditions; M=Marker (SeeBlue2), L=Load, FT=Flow-Through, W=Wash, E=Elutions. Flow through protein was used for re-folding. FIG. 17D Negative stain electron microscopy of purified TMV-NPNAx5 variants (×80 k magnification).

FIG. 18A Protein purification of TMV-NPNAx5-Acid Out construct showing the crude pellet and supernantant after cell lysis (P1 and 51). The 51 fraction was subjected to 25% ammonium sulfate precipitation and the resulting pellet P2 was re-suspended in 20 mM Tris, 20 mM Sodium chloride (pH 7.5). Supernatant after the ammonium sulfate precipitation (S2) was discarded. FIG. 18B Coomassie blue stained reduced gel showing TMV-NPNAx5-Acid Out purification over the Q sepharose column. L=Load, FT=Flow through, W=Wash. TMV-NPNAx5-Acid Out was eluted with 150 mM sodium chloride. FIG. 18C Negative stain electron microscopy of purified TMV-NPNAx5-Acid-out particles (×80K magnification).

FIG. 19C Negative Stain Electron Microscopy of ZMV-(VK247)x3 forms large rods and disks, whereas ZMV-(VK210)x5 only forms disks. FIG. 19D Ammonium sulfate (25% w/v) precipitated TMV-(VK247)x5 purified particles. (S1=soluble fraction of *E. coli* lysate, S2=supernatant after ammonium sulfate precipitation, P2=pellet after ammonium sulfate precipitation. P2 was used for load for Q sepharose binding. Only bound to Q sepharose in small amounts, most of protein in flow through. FIG. 19E Electron micrograph of TMV-(VK247)5 particles.

DETAILED DESCRIPTION

Figure 1C:
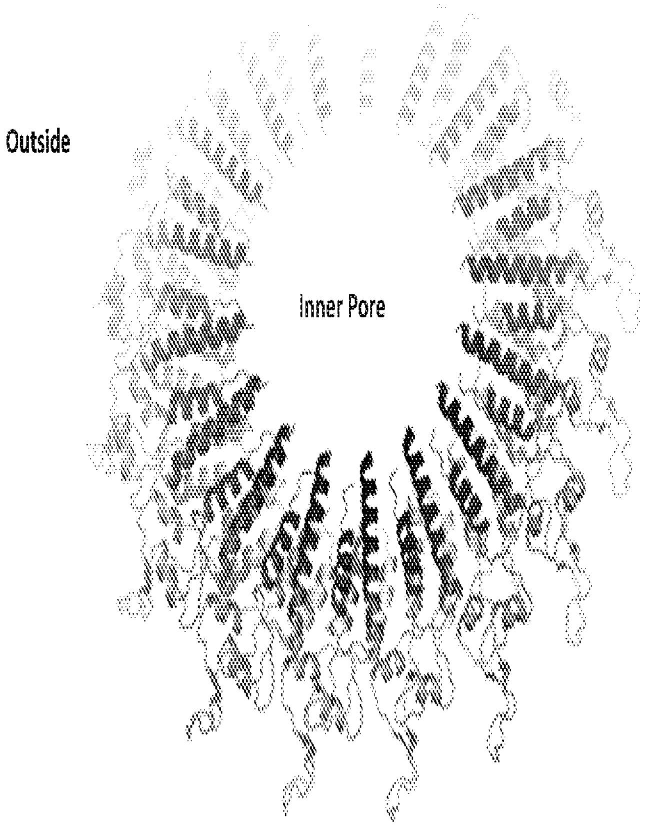

Before continuing to describe various aspects and embodiments in further detail, it is to be understood that this disclosure is not limited to specific compositions or process steps and may vary. As used in this specification and the appended claims, the singular form “a”, “an” and “the” include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

A "vaccine" as referred herein is defined as a pharmaceutical or therapeutic composition used to inoculate an animal in order to immunize the animal against disease and/or infection by an organism. Vaccines typically comprise one or more antigens derived from one or more organisms that when administered to an animal will stimulate an immune response.

The disclosure relates to the unexpected finding that recombinant proteins based on Tobomavirus capsid proteins and immunogenic epitopes can associate in a way that improves immune response to the epitopes. The inventors have studied the effects of density, valency and flexibility of epitopes on its immunogenicity in mice and Rhesus monkeys. Illustrating the technology using the circumsporozoite protein (CSP) repeat epitope (NPNA)n displayed on a Tobacco Mosaic Virus-like particle (VLP) as a model epitope, it was shown that optimal immunogenicity can be achieved by varying the number of repeating units and the location of this epitope on the VLP. The resulting vaccine was able to confer high level protection that was superior to the soluble CSP and it may not require complex adjuvants that contain potentially expensive and reactogenic immune modulators in humans. In one embodiment, a novel malaria vaccine based on this concept is described. In other embodiments, a similar approach can be carried out with other vaccine epitopes.

The disclosure illustrates that the immunogenicity of small peptides derived from infectious diseases can be improved. Vaccines based on short epitope sequences are inherently non-immunogenic. Particulate carriers are often used to make epitopes more immunogenic; however, many of the carrier proteins are based in non-lethal or attenuated forms of human pathogens. These include, for example, adenovirus, flu, hepatitis B, yellow fever, *shigella*, and *salmonella*. There can be pre-existing immunity to many of these human pathogens that affects the immune responses to target epitopes displayed on these particles. This problem can be solved as described herein by utilizing the Tobacco Mosaic Virus (TMV) virus capsid to which no significant pre-existing immunity exists in humans.

Tobacco Mosaic Virus coat protein is a 17 kDa monomer that can self-assemble into disks that can stack together into ~300 nm long and 18 nm wide rods (FIG. 1A, 1C). In its native conformation, the TMV capsid protein monomer has its N- and C-termini in close proximity pointing towards the outside of the disk (FIG. 1B). Dedeo et al. showed that the N- and C-termini can be re-engineered to point towards the inner pore [8] and the space created within the pore can be used to add prosthetic groups for building nano-machinery, thus resulting in a circular permutant of TMV [8]. A by-product of the circular permutant was that an extraneous loop was created that folded on to the surface of the TMV spiral. The inventors have developed an exposed loop variant of the circular permutant by placing a N-terminal hexa-histidine tag in the inner pore (for efficient purification) and the external loop has been utilized for antigenic presentation (FIG. 1B, 1C). While many spherical VLP systems can accommodate external peptides, there is a limit on the size of the displayed epitopes due to the steric constraints on packaging and sphere closure. In contrast, that spiral and flexible nature of stacked disks, the TMV exposed loop form is more amenable to structural modifications and display of larger epitopes.

As disclosed herein, the inventors have mapped protective *P. falciparum* CSP (PfCSP) epitopes by vaccinating mice with recombinant PfCSP GST fusion proteins that represented the N-terminal, the central repeat region or the C-terminal regions of CSP. Control mice received the GST fusion protein alone and naïve control mice received PBS. Mice were vaccinated with these proteins and challenged with transgenic mouse parasites that carry a copy of the *P. falciparum* CSP. Protection was observed only in the repeat region containing vaccine groups. Further when these antibodies were tested in an in vitro liver stage development assay, only repeat antibodies present in mAb 2A10, FL CSP serum and repeat-GST fusion protein serum inhibited liver stage development of the malaria parasite. Hence the protective epitope of CSP was the (NPNA)n region; specifically, the central repeat (NPNA)n region is the primary neutralizing epitope of the malaria vaccine candidate CSP.

Antigen size can be optimized, as described herein, by expressing the repeat epitope on the exposed loop form of TMV. Epitope density was modulated by changing the number of (NPNA)n units. The flexibility of the inherently unstructured (NPNA)n epitope was modulated by positioning it on the native N-terminal or the native C-terminal or the exposed loop of TMV. The most optimally immunogenic vaccine found in mice was then tested in Rhesus leading to a second generation malaria vaccine candidate. Finally a scale-up method for expression and purification of this TMV-based malaria vaccine was developed.

Thus, the inventors have developed capsids of the Tobamovirus genus as a vaccine delivery system. As such, the recombinant protein disclosed herein may include any suitable Tobamovirus protein, or circular permutant thereof, that allows for the production of the recombinant protein that induces or improves an immune response to an immunogenic epitope(s) of interest. In some embodiments, the Tobamovirus capsid protein may be a protein sequence, or circular permutant thereof, from the non-limiting group of Tobamovirus selected from Bell pepper mosaic virus (BPeMV), Beet necrotic yellow vein virus (BNYVV), Brugmansia mild mottle virus, Cactus mild mottle virus (CMMoV), Chara corallina virus (CCV), Clitoria yellow mottle virus, Cucumber fruit mottle mosaic virus, Cucumber green mottle mosaic virus(CGMMV), Cucumber mottle virus, Frangipani mosaic virus (FrMV), Hibiscus latent Fort Pierce virus (HLFPV), Hibiscus latent Singapore virus (HLSV), Kyuri green mottle mosaic virus, Maracuja mosaic virus (MarMV), *Nicotiana velutina* mosaic virus (NVMV), Obuda pepper virus (ObPV), Odontoglossum ringspot virus (ORSV), Paprika mild mottle virus, Passion fruit mosaic virus, Peanut clump virus (PCV), Pepper mild mottle virus (PMMoV), Potato mop-top virus (PMTV), Rattail cactus necrosis-associated virus(RCNaV), Rehmannia mosaic virus, Ribgrass mosaic virus (HRV), Sammons's Opuntia virus (SOV), Soil-borne wheat mosaic virus (SBWMV), Streptocarpus flower break virus, Sunn-hemp mosaic virus (SHMV), Tobacco latent virus, Tobacco mild green mosaic virus, Tomato mosaic virus (ToMV), Tobacco mosaic virus (TMV)—Type Species, Tomato mottle mosaic virus, Tropical soda apple mosaic virus, Turnip vein-clearing virus (TVCV), Ullucus mild mottle virus, Wasabi mottle virus (WMoV), Yellow tailflower mild mottle virus, Youcai mosaic virus (YoMV) aka oilseed rape mosaic virus (ORMV), and Zucchini green mottle mosaic virus.

As illustrated by the examples, the (NPNA)n protective epitope was used as a model antigen for display on this platform. (NPNA)n epitope was displayed on TMV and ZMV (Tobacco or Zucchini green mottle mosaic virus) capsid and these particles were expressed in *E. coli* and purified. The genes contained an N-terminal histidine tag for efficient purification. Purified particle vaccines were immunologically compared to soluble CSP vaccine which contains 18 copies of the NPNA epitope Immunized mice were tested for immunogenicity using a repeat peptide ELISA. Mice were also challenged using the PfCSP transgenic parasites. The TMV platform was found to be better than the soluble protein and also better than the ZMV platform for displaying certain CSP epitopes. Thus in some embodiments, epitopes can be made highly immunogenic by displaying them on the TMV particle delivery platform. In other embodiments, some epitopes may be made highly immunogenic by displaying them on the ZMV particle delivery platform.

In an aspect, the disclosure provides TMV- and ZMV-derived platforms that can be used to display epitopes derived from a wide variety of vaccine targets. Such targets may include antigens that cause, induce, or amplify diseases or clinical indications, antigens associated with infectious agents, or allergenic antigens.

The disclosure illustrates the effect of varying the epitope density and valency by displaying varying copies of the *Plasmodium falciparum* (NPNA)n epitope on the TMV particle. NPNAx3, NPNAx4, NPNAx5, NPNAx7, NPNAx10 and NPNAx20 were displayed on an exposed loop of TMV, the particles were expressed in *E. coli* and purified to homogeneity. These particles were then used as immunogens in a mouse transgenic parasite challenge model for malaria. The data showed that while (NPNA)x3 was antigenic, but increasing the density to NPNAx5 achieved optimal antigenicity. The immunogenicity did not increase further beyond NPNAx7. TMV VLP system was therefore found to be highly accommodative allowing for the presentation of up to 80 amino acid long loops. In one embodiment, the disclosure provides TMV based malaria vaccines containing an optimal number of repeat epitopes (e.g. NPNAx5) of the circumsporozoite protein.

The disclosure also illustrates the effect of flexibility on immunogenicity of epitopes on TMV, by placing the (NPNA)x5 epitope on either the N-terminal, C-terminal or an exposed loop part of the TMV capsid protein. TMV particles displaying these epitopes were expressed and purified from *E. coli* and used as immunogens in a mouse transgenic parasite challenge model for malaria. The looped form of the NPNAx5 antigen (tethered on both ends) was significantly more immunogenic and protective than the C- or N-terminally tethered forms, confirming that a structurally constrained and less flexible NPNA peptide was more immunogenic. In one embodiment, the disclosure provides TMV based vaccines that enhance immunogenicity of epitopes by placing them on the exposed loop region.

In one aspect the disclosure relates to a recombinant protein comprising a Tobamovirus capsid protein and an immunogenic epitope of an antigen of interest. In some embodiments, the capsid protein comprises the native amino acid sequence. In other embodiments the Tobamovirus capsid protein comprises a modified amino acid sequence. In some embodiments, the Tobamovirus capsid protein is selected from the group consisting of Tobacco mosaic virus (TMV) and zucchini green mottled mosaic virus (ZMV). In further embodiments, the capsid protein comprises SEQ ID NO: 1, SEQ ID NO: 2, SEQ ID NO: 3, or SEQ ID NO: 4, SEQ ID NO 21, or SEQ ID NO 22. In some embodiments, the recombinant protein is selected from the group consisting of: SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 23; SEQ ID NO: 24; and SEQ ID NO: 25.

As another aspect of the disclosure, nucleotide sequences are provided which encode a recombinant protein as described herein. Suitable nucleotide sequences include nucleotide sequences that encode for any of the amino acid sequences disclosed herein as well as sequences that are at least 85% homologous the amino acid sequences, at least 90% homologous, at least 95% homologous, at least 96%, 97%, 98%, or 99% homologous to the disclosed amino acid sequences. The nucleotide sequences can include at least one expression tag if desired.

As another aspect of the present technology, novel expression vectors are provided for any type of host cell such as, for example, eukaryotic cells (e.g., yeast) or prokaryotic cells (e.g., *E. coli*) where the vectors comprise a nucleotide sequence described herein. In some embodiments, the expression vectors can be stably cloned into a bacterial cell. In some embodiments, a suitable bacterial cell can be transformed with such an expression vector.

In another aspect of the disclosure, processes of producing and/or purifying the recombinant proteins are provided. The processes may comprise providing vectors or host cells that containing a nucleotide sequence that expresses one or more of the recombinant proteins described herein. The cells may be provided in a cell culture. The processes also comprise inducing expression of the recombinant protein in the cells, and collecting the cells or growth medium after a period of expression. The processes may also comprise lysing cells to obtain a cell lysate, collecting supernatant from the cell lysate or cell paste, and purifying the recombinant protein from the lysate or paste depending on the solubility of the particular protein. In embodiments, the proteins may be produced in a culture media that is free or substantially free of animal-derived components, such as media containing one or more or all of Phytone, yeast extract, ammonium sulfate, potassium phosphate monobasic, sodium phosphate dibasic, $MgSO_4$, glycerol, dextrose or kanamycin. The processes can include one or more purification steps, such as isolating and purifying the recombinant protein using chromatographic techniques (e.g., affinity, ion exchange, size exclusion, etc.) that are generally known in the art.

Purification of the recombinant proteins and VLPs may be performed by physical or chemical techniques or any combinations thereof that are routinely used in the art. Physical methods utilize the physical properties of the virus such as density, size, mass, sedimentation coefficient, and the like, and include but are not limited to, ultracentrifugation, density gradient centrifugation, ultrafiltration, size-exclusion chromatography, and the like. Chemical purification can employ methods such as adsorption/desorption through chemical or physiochemical reactions such as ion exchange chromatography, affinity chromatography, hydrophobic interaction chromatography, hydroxyapatite matrix, precipitation with inorganic salts such as ammonium sulfate, and the like.

In some embodiments, the purification method comprises expressing the recombinant protein in a host cell such as, for example *E. coli*, and subsequently purifying the protein and particle to levels of homogenenity required for human vaccines.

As discussed in the aspects and embodiments, the purified and isolated recombinant proteins disclosed herein may be high purity and suitable for human vaccination against a target antigen (e.g., virus, pathogen, microbe, etc.). Further, the recombinant proteins of the present technology can be produced under current good manufacturing practices to produce a vaccine grade protein composition made in animal-free media, a media free of animal-derived components. A human-grade vaccine suitable for administration to human subjects can be produced.

The recombinant Tobamovirus capsid protein vaccine platform was a surprisingly effective vaccines which are illustrated in the Examples that follow. In one embodiment, the disclosure provides vaccines containing *Plasmodium falciparum* (NPNA)n epitope (TMV-NPNA vaccines). The demonstrated protection for the TMV-NPNA vaccines as shown is notable because sterile protection in a mouse challenge model was achieved using an adjuvant that did not contain immune-modulators like MPL and QS21. While MPL and QS21 are known to be critical for protection induced by CSP vaccines in humans e.g. GlaxoSmithKline's (GS K) RTS,S [5] and R21 (reported recently by Oxford University [14]), the TMV based malaria vaccines disclosed herein achieved high level protection in the mouse model without MPL and QS21. These features indicate the described delivery platform can provide for vaccines that are less expensive to produce, more thermo-stable, and less reactogenic than current malarial vaccines being proposed and under investigation in humans.

The disclosure illustrates that the immunogenicity of epitopes can be improved by display within the Tobamovirus particle. In one embodiment, the immunogenicity of the inherently unstructured (NPNA)n epitope of Circumsporozoite protein was further improved by modulating the flexibility of this epitope by positioning it at various places within the Tobamovirus particle (N-terminal, C-terminal or within an exposed loop). Furthermore, the density of the (NPNA)n epitope could be varied by changing the number of copies (valency) of the NPNA repeats within the particle. Optimum flexibility and density can enhance the immunogenicity of the NPNA peptide antigen.

The inventors have studied the effects of particle size, density (valency) and flexibility on the immunogenicity of epitopes. Using the circumsporozoite protein repeat epitope (NPNA)n displayed on a Tobacco Mosaic Virus-like particle, it was shown that optimal immunogenicity can be achieved by varying the number of repeating units and the location of this epitope on the VLP. The resulting vaccine was able to confer high level protection that was superior to the soluble CSP and it did not require complex adjuvants that contain potentially expensive and reactogenic immune modulators. In one embodiment, a novel malaria vaccine based on this concept is described. In other embodiments, a similar approach can be carried out with other vaccine epitopes.

In one aspect, the disclosure provides a malaria vaccine developed by optimizing flexibility, density and epitopes using TMV particles as a display platform. The vaccine was highly immunogenic and protected mice in an adjuvant that did not contain immune modulators.

As another aspect of the present technology, methods of eliciting an immune response against an immunogenic epitope in an animal or human comprise administering a vaccine or recombinant protein as described herein. Methods of immunizing an animal or human against viruses and/or pathogens that cause diseases (e.g., such as malaria) are also provided. The methods comprise administering to the animal or human a vaccine or recombinant protein as described herein. In these methods, the vaccine can be administered intramuscularly or by another route known in the art.

The disclosure provides methods for raising or generating an immune response in a subject, comprising the step of administering an effective amount of a recombinant protein or vaccine that includes a recombinant protein as disclosed herein. The vaccines can be administered prophylactically (i.e. to prevent infection) or to provide protective and preferably involves induction of antibodies and/or T cell immunity against an immunogenic epitope of interest. The method may raise a primary immune response, a secondary immune response, a booster response or a combination of immune responses.

Bulk vaccine may be tested for sterility, protein, antigen and nucleic acid content using established assays. Vaccines may be diluted to a protein concentration that is suitable for an immunizing dose in a subject (e.g., a mammal such as a human). The final, vialed vaccine may be tested for purity, identity, osmolality, endotoxin, and sterility by various, standardized assays generally known in the art.

Reactogenicity of the vaccines disclosed herein may be monitored and evaluated as may be necessary. A reactogenicity event is typically identified as an adverse event that is commonly known to occur for the candidate therapeutic/prophylactic product being studied. Typically, such events are collected in a standard, systematic format using a graded scale based on functional assessment or magnitude of reaction. This helps to provide a risk profile of the candidate product and a defined listing of expected (or unexpected) adverse events, and whether such events are local or systemic events.

Vaccines are prepared for administration to mammals, suitably humans, mice, rats or rabbits, by methods known in the art, which can include filtering to sterilize the solution, diluting the solution, adding an adjuvant and stabilizing the solution.

The vaccines or compositions disclosed herein may be administered to a human or animal by a number of routes, including but not limited to, for example, parenterally (e.g. intramuscularly, transdermally), intranasally, orally, mucosally, topically, or other routes know by one skilled in the art. The term parenteral as used hereinafter includes intravenous, subcutaneous, intradermal, intramuscular, intraarterial injection, or by infusion techniques. The vaccine may be in the form of a single dose preparation or in multi-dose vials which can be used for mass vaccination programs. Suitable methods of preparing and using vaccines can be found in Remington's Pharmaceutical Sciences, Mack Publishing Co., Easton, Pa., Osol (ed.) (1980) and New Trends in Developments in Vaccines, Voller et al. (eds.), University Park Press, Baltimore, Md. (1978), incorporated by reference.

In some embodiments, a vaccine composition as disclosed herein may be administered parenterally in dosage unit formulations containing standard, well-known nontoxic physiologically acceptable carriers, adjuvants, and/or vehicles.

In some embodiments, the vaccine compositions may further comprise one or more adjuvants. An "adjuvant" is a substance that serves to enhance, accelerate, or prolong the antigen-specific immune response of an antigen when used in combination with specific vaccine antigens but do not stimulate an immune response when used alone. Suitable adjuvants include inorganic or organic adjuvants. Suitable inorganic adjuvants include, but are not limited to, for example, an aluminium salt such as aluminum hydroxide gel (alum) or aluminum phosphate, but may also be a salt of calcium (particularly calcium carbonate), iron or zinc, or may be an insoluble suspension of acylated tyrosine, or acylated sugars, cationically or anionically derivitised polysaccharides or polyphospharenes. Other suitable adjuvants are known to one skilled in the art. Suitable Th1 adjuvant systems may also be used, and include, but are not limited to, for example, Monophosphphorly lipid A, other non-toxic derivatives of LPS, and combination of monophosphoryl lipid A, such as 3-de-O-acrylated monophosphorly lipid A (#D-MPL) together with an aluminum salt.

Other suitable examples of adjuvants include, but are not limited to, Addavax (Invivogen), Matrix M (Novavax), AS01 (GSK), Depovax (Immunovaccines), MF59 (Seqirus), ALFQ (US Army), MPLA, *Mycobacterium tuberculosis, Bordetella pertussis*, bacterial lipopolysaccharides, aminoalkyl glucosamine phosphate compounds (AGP), or derivatives or analogs thereof, which are available from Corixa (Hamilton, Mont.), and which are described in U.S. Pat. No. 6,113,918; e.g., 2-[(R)-3-Tetradecanoyloxytetradecanoylamino]ethyl, 2-Deoxy-4-O-phosphono-3-O—[(R)-3-tetradecanoyoxytetradecanoyl]-2-[(R)-3-tetradecanoyoxytetradecanoylamino]-b-D-glucopyranoside, MPL™ (3-O-deacylated monophosphoryl lipid A) (available from Corixa) described in U.S. Pat. No. 4,912,094, synthetic polynucleotides such as oligonucleotides containing a CpG motif (U.S. Pat. No. 6,207,646), COG-ODN (CpG oligodeoxynucleotides), polypeptides, saponins such as Quil A or STIMULON™ QS-21 (Antigenics, Framingham, Mass.), described in U.S. Pat. No. 5,057,540, a pertussis toxin (PT), or an *E. coli* heat-labile toxin (LT), particularly LT-K63, LT-R72, CT-5109, PT-K9/G129; see, e.g., International Patent Publication Nos. WO 93/13302 and WO 92/19265, cholera toxin (either in a wild-type or mutant form). Alternatively, various oil formulations such as stearyl tyrosine (ST, see U.S. Pat. No. 4,258,029), the dipeptide known as MDP, saponin, cholera toxin B subunit (CTB), a heat labile enterotoxin (LT) from *E. coli* (a genetically toxoided mutant LT has been developed), and Emulsomes (Pharmos, LTD., Rehovot, Israel). Various cytokines and lymphokines are suitable for use as adjuvants. One such adjuvant is granulocyte-macrophage colony stimulating factor (GM-CSF), which has a nucleotide sequence as described in U.S. Pat. No. 5,078,996. The cytokine Interleukin-12 (IL-12) is another adjuvant which is described in U.S. Pat. No. 5,723,127. Other cytokines or lymphokines have been shown to have immune modulating activity, including, but not limited to, the interleukins 1-alpha, 1-beta, 2, 4, 5, 6, 7, 8, 10, 13, 14, 15, 16, 17 and 18, the interferons-alpha, beta and gamma, granulocyte colony stimulating factor, and the tumor necrosis factors alpha and beta, and are suitable for use as adjuvants.

Further suitable adjuvants include, but are not limited to, aluminum salts such as aluminum hydroxide or aluminum phosphate, salts of calcium, iron or zinc, insoluble suspensions of acylated tyrosine, or acylated sugars. Other suitable adjuvants cationically or anionically derivatized saccharides, polyphosphazenes, biodegradable microspheres, nanoparticles, liposome based formulations, monophosphoryl lipid A (MPL), lipid A derivatives (for example, of reduced toxicity), 3-O-deacylated MPL, quil A, Saponin, QS21, Freund's Incomplete Adjuvant (Difco Laboratories, Detroit, Mich.), Merck Adjuvant 65 (Merck and Company, Inc., Rahway, N.J.), emulsion or a water-in-oil emulsion, ASO (Smith-Kline Beecham, Philadelphia, Pa.), AS)1 (GlaxoSmithKline), CpG oligonucleotides, bioadhesives and mucoadhesives, polyoxyethylene ether formulations, polyoxyethylene ester formulations, muramyl peptides or imidazoquinolone compounds (e.g. imiquamod and its homologues), or Montanide ISA 720. Human immunomodulators suitable for use as adjuvants in the invention include cytokines such as interleukins (e.g. IL-1, IL-2, IL-4, IL-5, IL-6, IL-7, IL-12, etc), macrophage colony stimulating factor (M-CSF), tumor necrosis factor (TNF), granulocyte and macrophage colony stimulating factor (GM-CSF).

The adjuvant may be provided in the form of microparticles or liposomes containing one or more of the adjuvants disclosed herein or other adjuvants, either inside the particle or on the surface. Alternatively, some adjuvants can be provided in the form of an oil and water emulsion, such as an oil-in-water emulsion or a water-in-oil emulsion. In some embodiments, the adjuvant can be selected to induce a specific type of immune response, such as a B-cell response or a T-cell response. In one embodiment of the present technology, the vaccine induces an immune response. Suitable adjuvants which promote an immune response include, but are not limited to, derivatives of lipid A (preferably of reduced toxicity), Monophosphoryl lipid A (MPL) or a synthetic derivative thereof, particularly 3-de-O-acylated monophosphoryl lipid A (3D-MPL), QS21 and a combination of monophosphoryl lipid A and QS21, or adjuvants that promote TLR4, TLR,7, TLT8, TLR9, optionally 3-de-O-acylated monophosphoryl lipid A together with an aluminum salt. In another aspect, the disclosure provides vaccines comprising the recombinant proteins disclosed herein and at least one adjuvant. The vaccines can be used to vaccinate a subject (such as a human or animal) and elicit an immune response. In some aspects, the vaccine produces high titer antibodies in the subject.

In some aspects, the recombinant protein induces high titer antibodies when formulated with at least one adjuvant. In further aspects, vaccination with the recombinant protein and at least one adjuvant confers partial or full protection in a vaccinated subject against a viral/pathogen challenge.

As yet another aspect of the disclosure, vaccines suitable for human administration are provided. The vaccines comprise a recombinant protein as described herein, and one or more adjuvants. In some embodiments the vaccines may have an endotoxin level less than about 5 endotoxin units per microgram of protein, and/or less than about 1 ng/ml of bacterial host proteins. In some embodiments, the vaccines have a soluble protein content, and the soluble protein content is greater than 95%, alternatively greater than 99%, recombinant protein content as measured by gel densitometry.

The vaccine compositions can be lyophilized to produce a vaccine formulation in a dried form for ease in transportation and storage. Further, the vaccine may be prepared in the form of a mixed vaccine which contains the recombinant protein(s) described herein and at least one other antigen as long as the added antigen does not interfere with the ability and/or efficacy of the vaccine, and as long as the added antigen does not induce additive or synergistic side effects and/or adverse reactions. The vaccine can be associated with chemical moieties which may improve the vaccine's solubility, absorption, biological half-life, etc. The moieties may alternatively decrease the toxicity of the vaccine, eliminate or attenuate any undesirable side effect of the vaccine, etc. Moieties capable of mediating such effects are disclosed in Remington's Pharmaceutical Sciences (1980). Procedures for coupling such moieties to a molecule are well known in the art.

The vaccine may be stored in a sealed vial, ampule or the like. The vaccines disclosed herein can generally be administered in the form of a spray for intranasal administration, or by nose drops, inhalants, swabs on tonsils, or a capsule, liquid, suspension or elixirs for oral administration. In the case where the vaccine is in a dried form, the vaccine is dissolved or suspended in sterilized distilled water before administration. Any inert carrier may be used, such as saline, phosphate buffered saline, or any such carrier in which the vaccine components have suitable solubility.

In some embodiments, the vaccines, in addition to the recombinant protein and adjuvant, comprise one or more pharmaceutically acceptable carriers or excipients. Excipients include any component that does not itself induce the production of antibodies and is not harmful to the subject receiving the composition. Suitable excipients are typically large, slowly metabolized macromolecules such as proteins, saccharides, polylactic acids, polyglycolic acids, polymeric amino acids, amino acid copolymers, sucrose, trehalose, lactose and lipid aggregates (such as oil droplets or liposomes). Suitable pharmaceutical carriers are well known to those of ordinary skill in the art, including, but not limited to, diluents, such as water, saline, glycerol, and others. Suitably, sterile pyrogen-free, phosphate buffered physiologic saline is a pharmaceutical carrier. Additionally, additives, such as wetting or emulsifying agents, pH buffering substances, and the like, may be present. If in a solution or a liquid aerosol suspension, suitable carriers can include, but are not limited to, salt solution, sucrose solution, or other pharmaceutically acceptable buffer solutions. Aerosol solutions may further comprise a surfactant.

Among the acceptable vehicles and solvents that may be used include water, Ringer's solution, and isotonic sodium chloride solution, including saline solutions buffered with phosphate, lactate, Tris and the like. In addition, sterile, fixed oils are conventionally employed as a solvent or suspending medium, including, but not limited to, for example, synthetic mono- or di-glycerides. In addition, fatty acids such as oleic acid find use in the preparation of injectables.

Vaccines may be in an aqueous form, for example, but not limited to, solutions, particles or suspensions. The vaccine can be an oil and water emulsion, such as an oil-in-water emulsion or a water-in-oil emulsion. Liquid formulations allow the compositions to be prepackaged and administered direct from their packaged form without the need for reconstitution. Compositions may be presented in vials, or they may be presented in ready filled syringes. A syringe can include a single dose of the composition, whereas a vial may include a single dose or multiple doses (e.g., 2, 3, 4, 5, 10, or more doses). Preferably, the dose is for human administration, suitably for an adult, adolescent, toddler, infant or less than one year old human and may be administered by injection.

Injectable preparations, for example sterile injectable aqueous or oleaginous suspensions, are formulated according to the known art using suitable dispersing or wetting agents and suspending agents. The sterile injectable preparation are also a sterile injectable solution or suspension in a nontoxic parenterally acceptable diluent or solvent, for example, as a solution in 1,3-butanediol.

In some embodiments, a vaccine may comprise a combination of the recombinant proteins disclosed herein, or may comprise additional immunogenic components that may provide a desired immune response.

Vaccines of the present technology are formulated into suitable dosage for the subject to which it is to be administered. The dosage administered may vary with the condition, sex, weight and age of the individual; the route of administration; and the adjuvant used. The vaccine may be used in dosage forms such as suspensions or liquid solutions. The vaccine may be formulated with an pharmaceutically acceptable carrier as described above. Suitable dosages include, but are not limited to, about 1 to about 100 micrograms, alternatively about 5 to about 50 micrograms, of a recombinant protein as described herein.

Subjects may receive one or several booster (subsequent) immunizations adequately spaced. Dosing treatment can be a single dose schedule or a multiple dose schedule. Multiple doses may be used in a primary immunization schedule and/or in a booster immunization schedule. Suitable timing between the administration of priming doses (e.g. between 4-16 weeks) and between the administration of priming and boosting doses can be determined.

Some aspects and embodiments of the disclosure are illustrated by the following examples. These examples are provided to describe specific embodiments of the technology and do not limit the scope of the disclosure. It will be understood by those skilled in the art that the full scope of the disclosure is defined by the claims appending this specification, and any alterations, modifications, or equivalents of those claims.

EXAMPLES

Example 1. Expression of GST Fusion Proteins Representing Various Regions of *P. falciparum* CSP and Design of TMV Capsid Proteins The N-terminal, repeat and the C-terminal regions of *P. falciparum* CSP were PCR amplified and expressed as GST fusion proteins in the *E. coli* host. The proteins were purified using GST columns and used to vaccinate mice as described below.

In its native conformation the TMV capsid protein has N- and C-termini in close proximity on one side of the molecule (FIG. 1A), that are on the external surface of the ring or spiral particle. However, placing the N- and C-termini to the other side of the molecule, within the pore (FIG. 1B) the original N- and C-termini can be joined by a loop. Dedeo et al., [8] used this circular permutant of TMV to create space within the TMV pore for the addition of prosthetic groups for the purpose of building 'nano machinery'. A byproduct of the published construct of Dedeo was the extraneous loop on the external surface of the TMV spiral that the inventors have recognized and utilized as a site for antigenic presentation of peptides (exposed loop form). This circular permutant of the capsid is termed the 'exposed loop' form, and the exposed loop allows for the placement of NPNA repeats in the loop linker. The (NPNA)x3 epitope, while being the less flexible by virtue of being tethered on both ends, is considerably more conformationally restrained than the (NPNA)x3 displayed as a N- or C-terminal extension (FIGS. 1, 2, 3 and 4). An N-terminal histidine tag within the TMV pore was added that allowed for efficient purification under denaturing conditions. The monomers of the TMV displaying the epitope on its surface can self-assemble in *E. coli* into a disk (FIG. 1C).

Example 2. Loop Length and Valency Optimization

To determine the optimum loop length and valency for an NPNA repeat, TMV exposed loop form capsids were generated displaying (NPNA)x3, x4, x5, x7, x10 and x20 repeats. To give a visual picture of the effect of this loop size increase, the lowest energy structures generated by Robetta [15] (available on-line at robetta.bakerlab.org) are shown in FIG. 2 with an overlay of the lowest 4 energy structures in FIG. 3. As would be expected, increasing the length of a loop results in increased density of NPNA antigen, but also results in increased flexibility with the NPNA peptide adopting multiple conformations. Interestingly, for the larger NPNAx10 or x20 loops the size of the loop starts to approach the size of the capsid protein. For these large loops interloop steric constraints would start to play a part such that loop flexibility may be diminished.

Figure 4A:
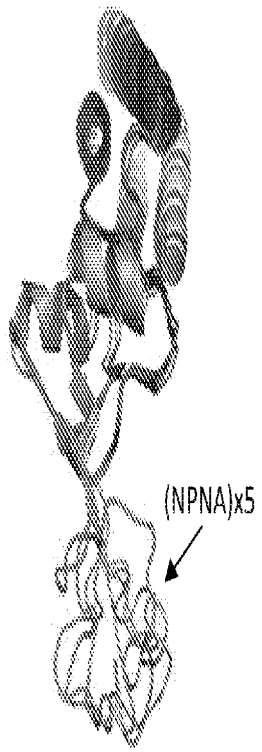
FIG. 4A-4C provides a side view down radial spiral axis comparing the flexibility of the (NPNA)x5 repeats on the loop (FIG. 4A), N-terminus (NT) (FIG. 4B) or C-terminus (CT) (FIG. 4C). 4 lowest energy structures generated by Robetta are overlaid and arrow represents the NPNA epitope.
Figure 4B:
Figure 4C:
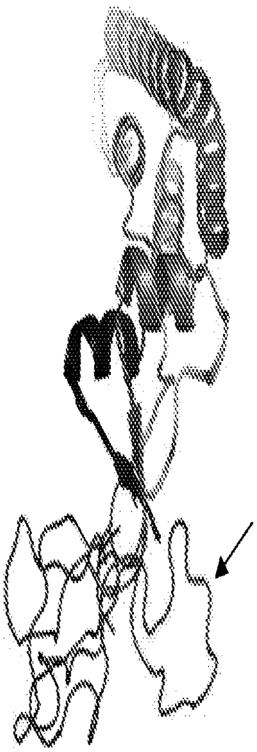

Example 3. Comparison of the Location of the Epitope on a Loop or at the N- and C-Terminal In its native conformation the TMV capsid protein has N- and C-termini on one side of the protein such that they are on the outside of the spiral. NPNA repeats can be added to the N- or C-termini such that they are accessible to the immune system (FIG. 1). As would be expected that epitopes that are only tethered at the C- or the N-terminal are considerably more flexible than NPNA epitope that are tethered at both ends as a loop of a similar size. The (NPNA)x5 epitope expressed on the exposed loop is therefore considerably more conformationally restrained than the (NPNA)x5 epitope displayed on terminal extensions (FIG. 4).

Example 4. Comparison of the TMV (Tobacco Mosaic Virus) and ZMV (Zucchini Green Mottle Mosaic Virus) Scaffolds TMV belongs to a large family of diverse Tobomavirus species that infect a variety of plants. A variety of these sequences was examined in order to identify proteins that were more hydrophilic and potentially more amenable to mass production. Overall TMV and ZMV are relatively divergent with 36% sequence identity, but there predicted tertiary structures would be identical (not shown). The sequence alignment of TMV with ZMV in FIG. 5 is shown with an e/b identifier showing if a particular amino acid was buried or exposed on the folded monomer. The number of exposed carbons was summed and found to be lower in ZMV. On the basis of sequence diversity and predicted higher solubility of the protein monomer the ZMV sequence was selected for further study. Hence, the expression of immunogenicity of the NPNA epitope was tested in two distinct members of the Tobomavirus family to determine suitability for the production of vaccines.

Example 5. Production and Purification of TMV Fused NPNA Particles

Genes for the TMV and ZMV particles were optimized for high level expression in *E. coli* (SEQ ID NOs 5, 6, 7, 8, 9, 10, 11, 12, 14, and 15). The genes were cloned in an expression plasmid and transformed into BL21(DE) cells. The cells were grown in 1 L culture in shake flask, and induced at an OD of 0.7 using 0.1 mM IPTG at 37 C. After 2 hr induction the cells were harvested by centrifugation and stored at −80 C. In a typical lab grade production run, 2 grams of *E. coli* paste was suspended in 100 ml of 20 mM Tris, 20 mM NaCl pH 9.0 (Buffer A). One ml of protease inhibitor cocktail was added to it just before microfludization. After microfludization, lyzed cells were centrifuged at 13,000 rpm for 30 min. Since most of the protein remained in the pellet, it was solubilized in 20 mM Tris, 20 mM NaCl, 7M urea pH 9.0 (Buffer B), and centrifuged at 13,000 rpm for 30 mM. Resultant supernatant was collected, and loaded onto 6 ml Ni-NTA column equilibrated in Buffer B. The column was washed with 60 ml of Buffer B, and then 70 ml of Buffer B containing 20 mM imidazole. Finally, protein was eluted in Buffer B containing 250 mM imidazole. The peak fractions of Ni-NTA column were pooled, and diluted 10× with Buffer B. This dilute protein was loaded onto 3 ml Q-Sepharose column equilibrated in Buffer B. Most of the protein was in the flow-thru. OD 280 of the flow-thru was measured, and protein was diluted to an $OD_{280}$ of 0.1 with Buffer B. 100 ml of this protein solution was dialyzed against 4.5 Lt. of Buffer A containing 0.05% β-mercaptoethanol overnight at 4 C (to remove the urea). The following day the protein is dialyzed into 4.5 Lt. of 20 mM Phosphate, 20 mM NaCl pH 7.4 (Buffer C) for 8 hrs. The buffer was replaced with 4.5 Lt. of fresh Buffer C, and dialysis was continued overnight. Next day, the protein solution was filtered through 0.22 μM filter, concentrated on a Centricon concentrator to 15 ml, and was further centrifuged to remove any precipitate.

Particle size was determined by dynamic light scattering on a Malvern Zetasizer NanoS, and by electron microscopy. The presence of the NPNA epitope on the particles was confirmed by a western blot using polyclonal antibodies against CSP. Protein was stored at −80° C. until further use.

Example 6. Immunization of Mice

Vaccines were formulated in Addavax adjuvant (Invivogen, San Diego, Calif.) as per manufacturer's instructions. Female C57Bl/6J mice (The Jackson Laboratory, Bar Harbor, Me., USA) were immunized intramuscularly (IM) with 0.05 ml of the vaccines containing 2.5 μg of antigen by injection in rear thighs at 0, 3, and 6 weeks. The animals were bled three weeks after the first and second immunizations and on the day before challenge.

Example 7. Malaria Challenge

Protective efficacy of vaccines was assessed using transgenic *P. berghei* (Tr-Pb) sporozoites expressing a functional full-length *P. falciparum* CSP gene. Animals were challenged 15 days after the last immunization with 100 μL intravenous (IV) injection of 3000 Tr-Pb sporozoites into the caudal vein, as described by Porter et al. [9]. Blood-stage parasitemia was detected by microscopy of giemsa-stained thin blood smear. Animals were considered protected if parasitemia was not detected during a two-week observation period immediately following challenge.

Example 8. ELISA (NANP)6C peptide at 100 ng/well in PBS was coated on Immulon 2HB 96-well flat bottom microtiter plates (Thermo Scientific, Rochester, N.Y., USA). Coated plates were incubated overnight at 4° C. and all subsequent incubations were at +22° C. Plates were washed three times with PBS/0.05% Tween-20 (wash buffer) and blocked 1.5 h with 0.5% casein/PBS/1% Tween-20. Plates were washed three times and incubated 2 h with serially diluted sample in 0.5% casein/PBS/0.05% Tween-20 (dilution buffer). Plates were washed three times and 25 ng/well of secondary antibody (goat anti-mouse IgG-HRP) in dilution buffer was added for 1 h. Plates were then washed a final four times before being developed for 1 h with ABTS 2-component substrate (KPL) and stopped by adding SDS to final 2% concentration. Absorbance was read at 414 nm ($OD_{414}$). Antibody titer was determined at the concentration where $OD_{414}$=1.000, using Gen5™ 4-parameter nonlinear regression (BioTek, Winooski, Vt., USA).

Figure 6A:
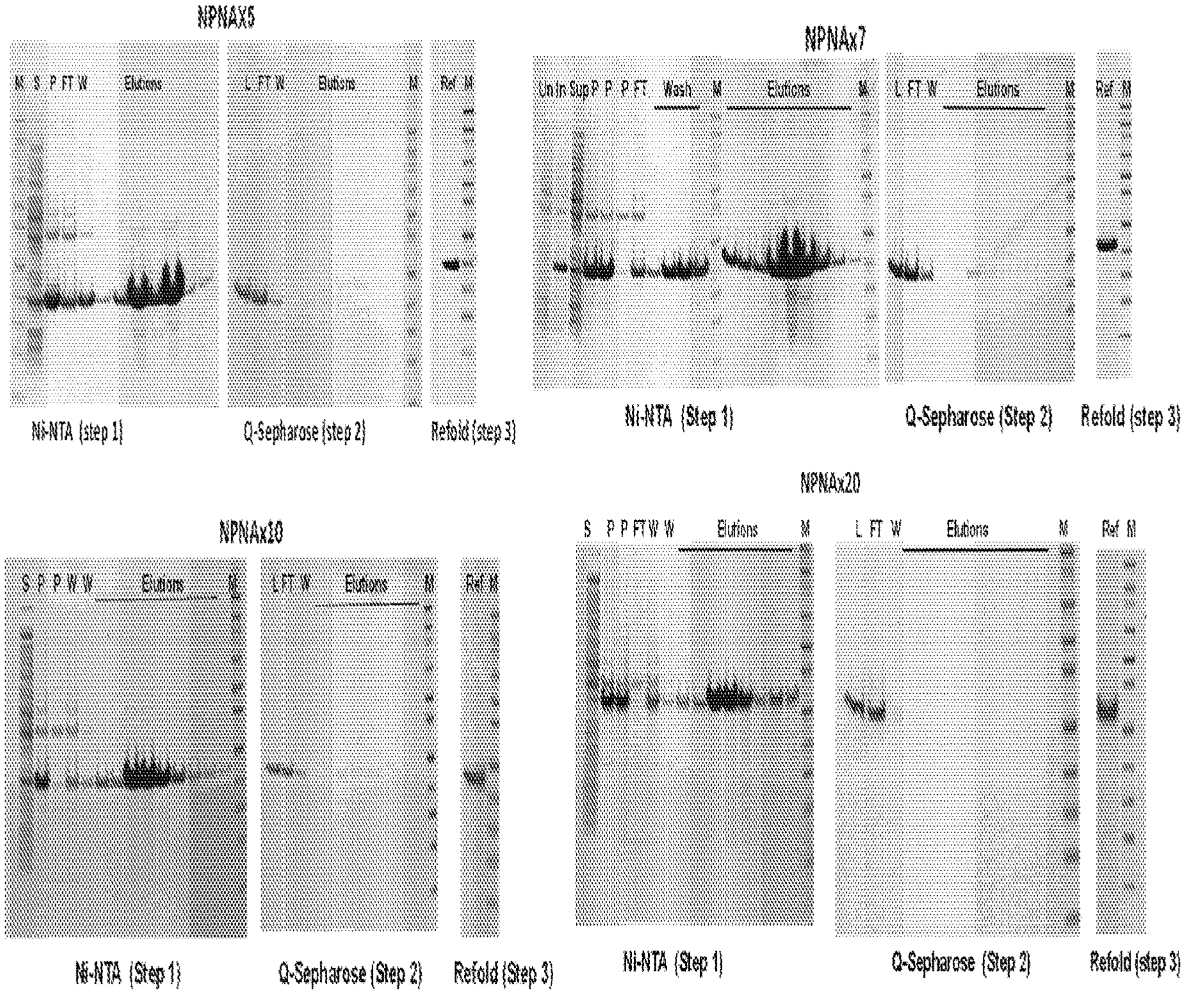
FIG. 6A-6C show purification and characterization of TMV particles from the insoluble inclusion body fraction under denaturing conditions.
Figure 6B:
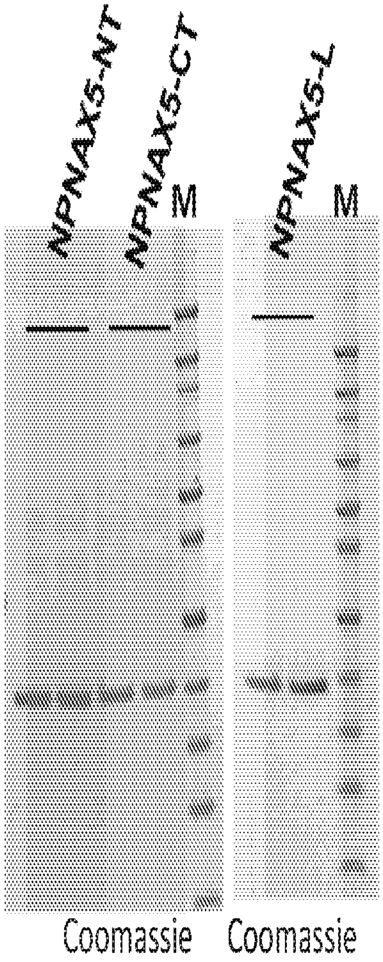
Figure 6C:
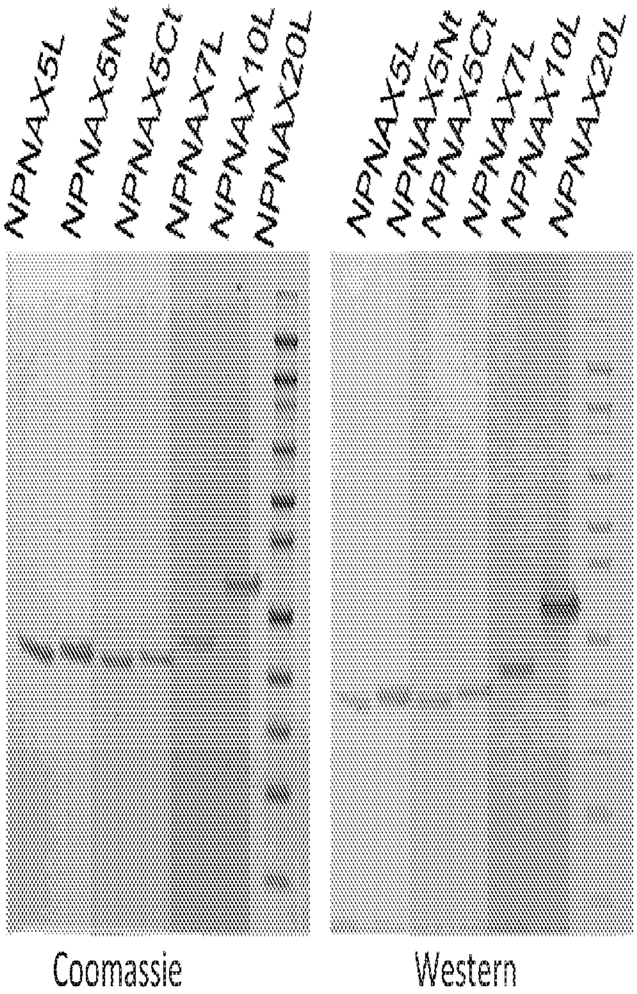
Figure 7A:
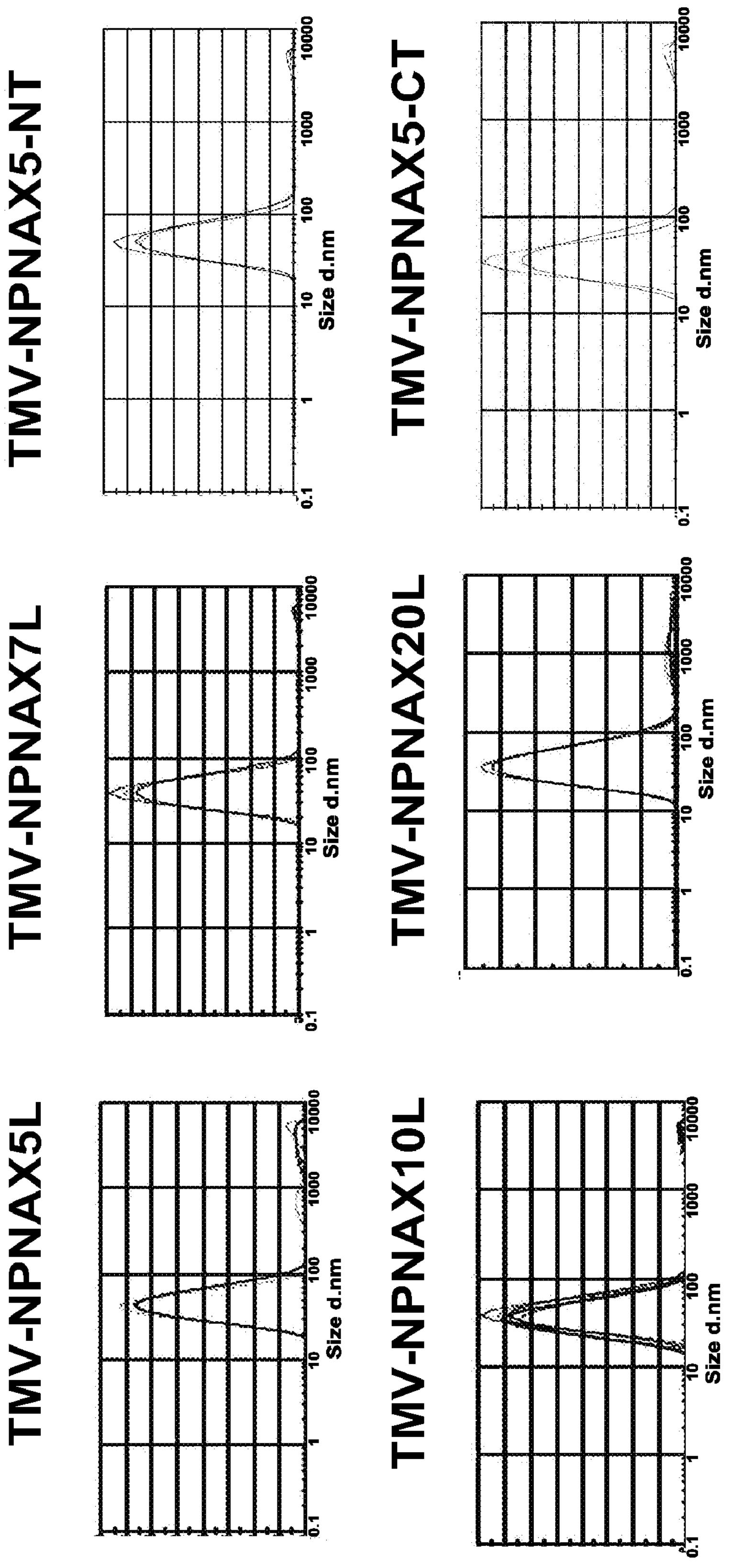
FIG. 7A-7B show characterization of TMV particles by dynamic light scatter (FIG. 7A) and electron microscopy (FIG. 7B).
Figure 7B:
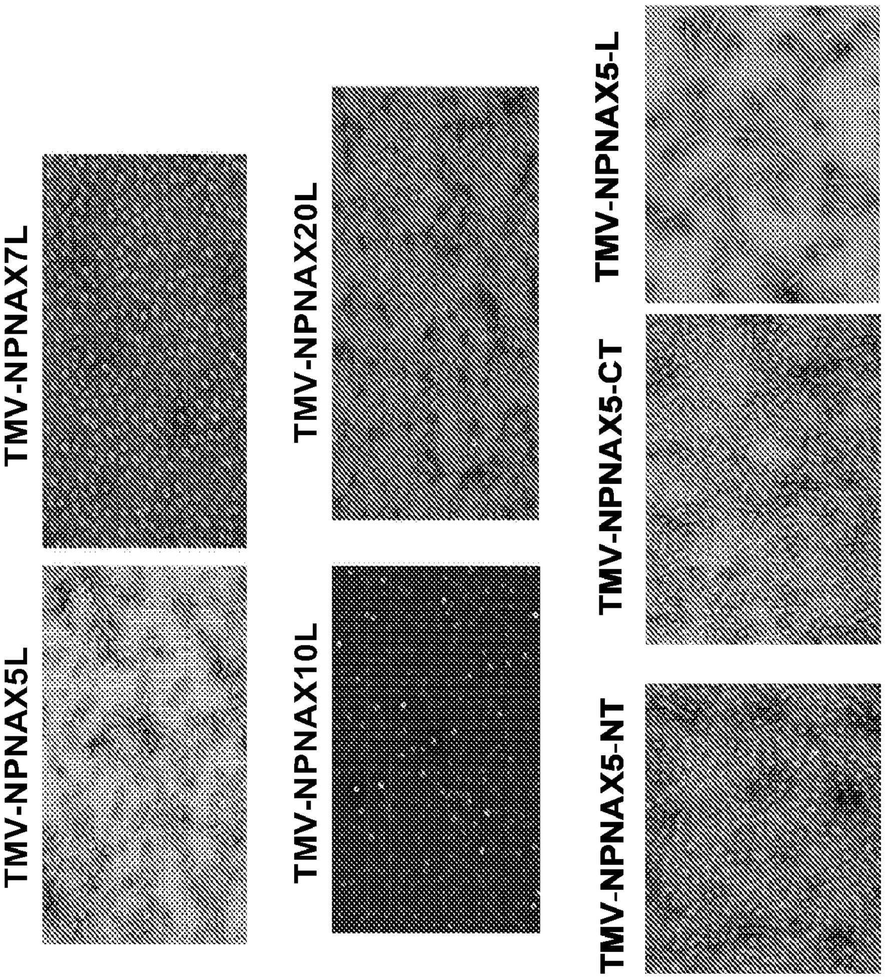

Example 9. Purification and Characterization of TMV Particles Using a 3-Step Protocol Under Denaturing Conditions FIG. 6A shows the purification of the various TMV particles. The whole cell lysate was centrifuged and separated into the soluble supernatant (lanes labelled as S) and Pellet (lanes labelled as P). Majority of the TMV monomer was in the insoluble pellet fraction, and this pellet was solubilized in urea and loaded on a Ni-NTA column. While the flow-through (lanes labelled as FT) contained some unbound protein, the majority of the protein bound to the column. The column was washed (lanes labeled as W) and protein was eluted in multiple fractions (lanes labelled as Elution). The Ni-NTA elutions were pooled, diluted and passed over a Q-sepharose column. This allowed the removal of majority of the endotoxin and the final product was collected in the flow-through (lanes labelled as FT) of the Q-Sepharose column. Table 1 shows the endotoxin contents after Q-column chromatography. Washing and elution of Q-sepharose column showed very little protein bound to the column. The FT of the Q-sepharose column was refolded using a 2-step dialysis (lanes labelled as Ref). FIG. 6B shows the purified proteins for the NPNAx5-CT, NPNAx5 -NT and NPNAx5-L (all proteins loaded in duplicate lanes) and FIG. 6C shows the identity of the particles stained by coomassie blue (left panel) and their positive reactivity to CSP specific mouse polyclonal antibodies (right panel on FIG. 6C). FIG. 7A shows dynamic light scattering analysis of the various particles refolded and used in vaccinations and 7B shows their respective electron-micrographs (EM). The vaccine preparations appeared to be a mixture of discs and rod forms of TMV and the average particle size of our vaccines by DLS was approximately 50 nm. By EM analysis the proteins expressing shorter epitopes (NPNAx3,4,5-L and NPNAx5-CT) tended to form rings and long rods, whereas proteins with higher epitope density (NPNAx7,10,20 and NPNAx5-NT) tended to form rings with short rods.

TABLE 1

Endotoxin content of some of the final products used in the mouse vaccine studies

| Constructs | Protein content by OD280 | Endotoxin level EU/mg |
|---|---|---|
| TMV-NPNAx5L | 0.356 | 0.15 |
| TMV-NPNAx7L | 0.59 | 0.27 |
| TMV-NPNAx10L | 0.747 | 0.17 |
| TMV-NPNAx20L | 0.549 | 0.127 |

Example 10. Immunogenicity Data—Mapping the Primary Neutralizing Epitope of *P. falciparum* CSP (Mouse Study 1)

Figure 8A:
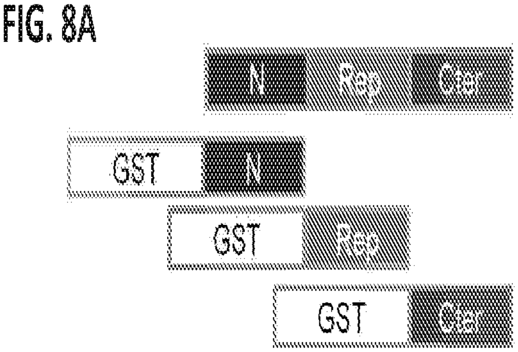
FIG. 8A-8D depict mouse protection data using GST fusion proteins (Study 1)
Figure 8B:
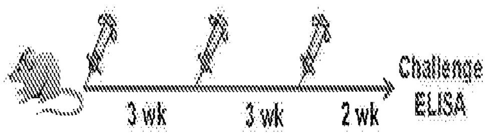
Figure 8C:
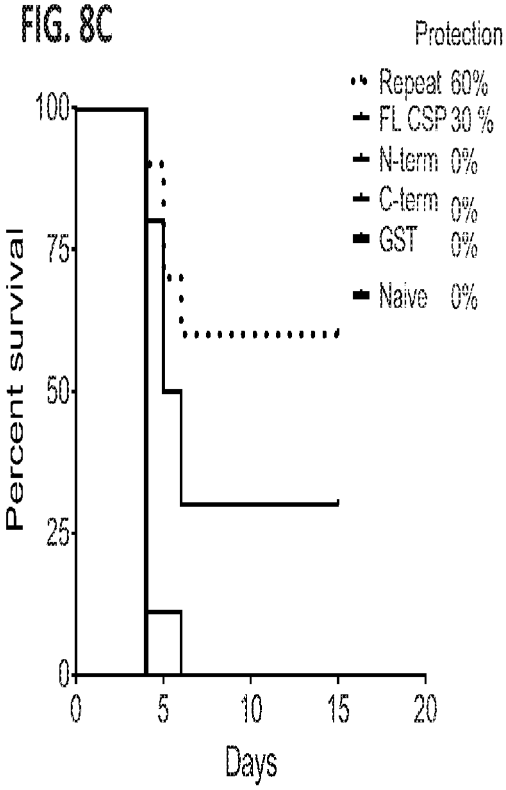
Figure 8D:
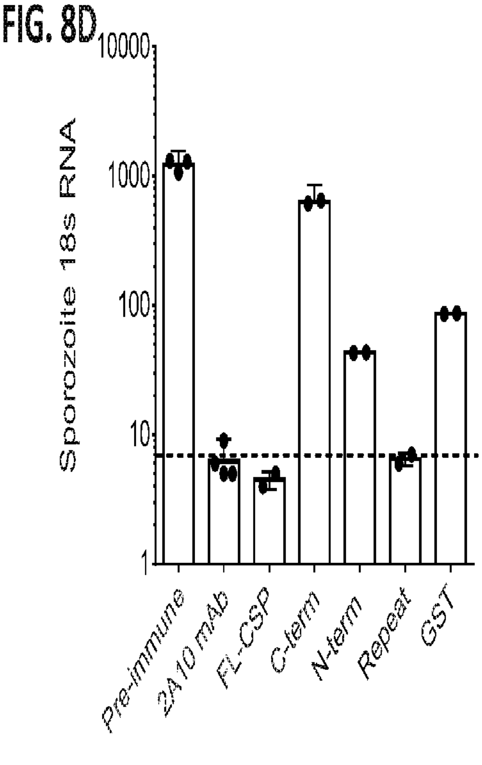

GST fusion proteins representing the N-terminal (N-ter), central repeat (NPNA)n region (Rep) or the C-terminal region (Cter) were expressed and purified from *E. coli* (FIG. 8A). Recombinant GST fusion proteins along with the full-length CSP vaccine were used to immunize C57BL6 mice (schematic of vaccination is shown in FIG. 8B). At 2 weeks after the $3^{rd}$ dose, mice were challenged with a transgenic parasite line that contains *P. falciparum* CSP expressed on *P. berghei* rodent parasites. Only the (NPNA)n repeat region protein vaccinated mice were protected against malaria (survival of 50% mice) while no other CSP protein region was protective (FIG. 8C). This experiment proved without a doubt that the central (NPNA)n repeat region was the primary neutralizing epitope of CSP. Mouse antibodies from this trial were also tested for in vitro sporozoite invasion inhibition (FIG. 8D). Only the sera that contained against the (NPNA)n region antibodies could inhibit sporozoite invasion by 2× log as compared to the No-antibody control. The level of inhibition with the repeat antibodies was similar to that obtained by polyclonal antibodies to the full-length CSP (labelled as FL) which also contains the repeat epitope and a positive control monoclonal antibody (2A10) that reacts to the repeat region and is inhibitory to sporozoite invasion (FIG. 8D).

Example 11. Immunogenicity Data—Comparison of Immunogenicity and Protective Efficacy of NPNA Expressing TMV and ZMV Particles with Soluble CSP (Mouse Study-2)

Figure 9A:
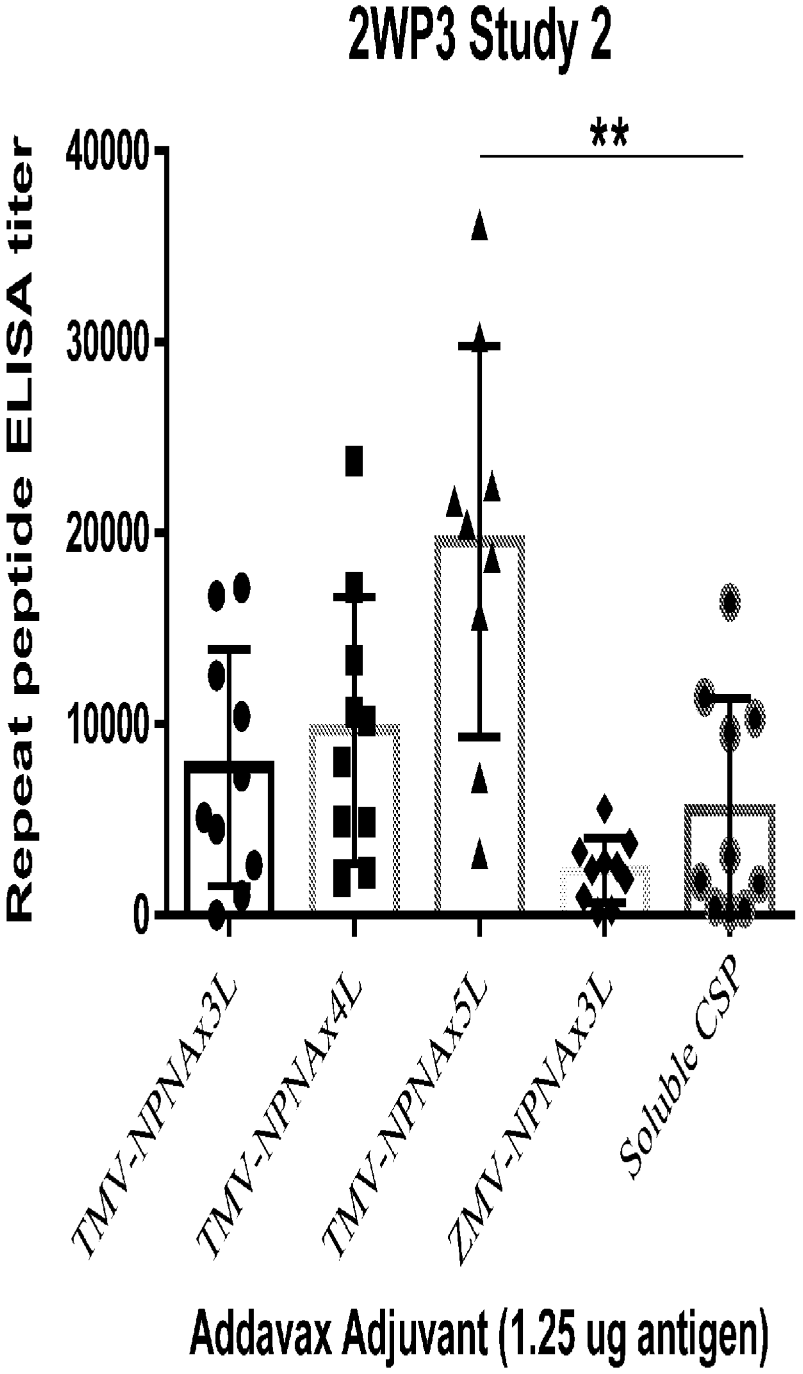
FIG. 9A-9B show immunogenicity and protection data against transgenic parasite challenge (Study 2)
Figure 9B:
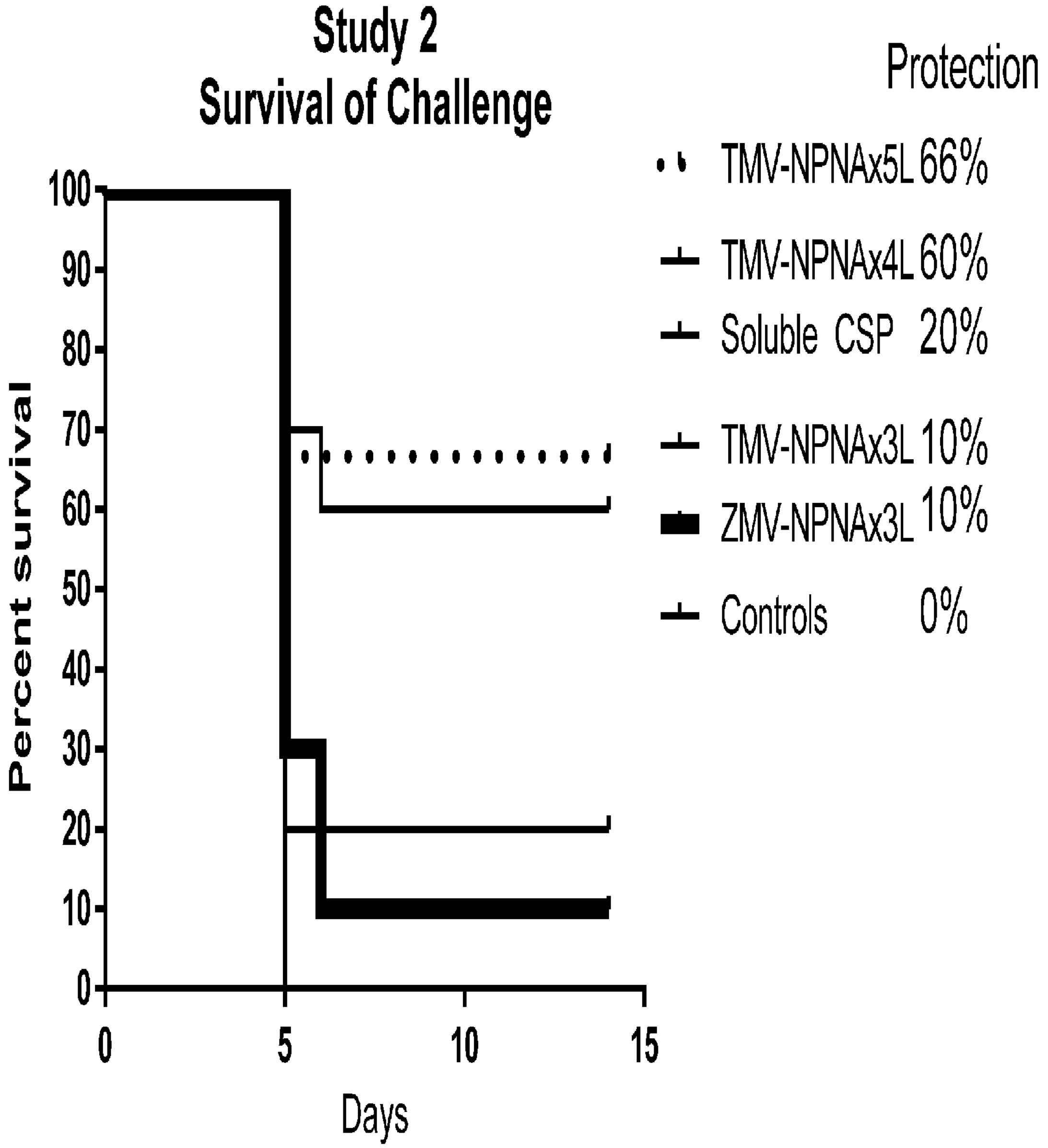

Using Addavax as the adjuvant, mice were immunized with 1.25 ug vaccines where the epitope was displayed on the exposed loop. These vaccines were: TMV-NPNAx3, TMV-NPNAx4, TMV-NPNAx5, ZMV-NPNAx3 and soluble CSP. Vaccines were given three times at 3 week intervals and NANP specific ELISA data at 2 weeks post $3^{th}$ vaccination (2WP3) were compared (FIG. 9A). To determine the functionality of these antibodies, the vaccinated mice were challenged with 3000 trangenic *P. berghei* parasites that harbored the *P. falciparum* CSP gene and determined if they were infected (FIG. 9B). The naïve control mice showed 100% infectivity and one mouse in the TMV-NPNAx5L mouse died due to causes unrelated to vaccination.

Delivery Method:

Immunogenicity of the particulate vaccines (TMV or ZMV) containing NPNAx3, NPNAx4 or NPNAx5 epitopes on the exposed loop were compared to a soluble CSP protein which also contains NPNAx18 epitopes [16]. TMV-NPNAx5 particles showed significantly higher ELISA response compared to the soluble CSP and the protection for this TMV-NPNAx5 group was 66% while soluble CSP protected only 20% of the mice (FIG. 9).

Particulate Platform:

To determine if TMV and ZMV particles had equivalent immunogenicity and protection, TMV-NPNAx3 and ZMV-NPNAx3 groups were compared. The TMV platform induced higher repeat specific ELISA titers than the ZMV platform, however, in terms of protection the ZMVx3 and TMVx3 vaccines performed similarly, both protected only 10% of the mice (FIG. 9).

Epitope Density:

To determine the effects of increasing epitope density and valency the NPNAx3, NPNAx4 and NPNAx5 displaying particles were compared on the TMV platform. The repeat peptide ELISA titers of NPNAx5-L group were better than NPNAx4 and NPNAx3 and the protection of the NANPx5 was also the highest (66%) among all groups (FIG. 9).

Example 12. Comparison of Immunogenicity and Protective Efficacy of Varying Number (Valency) and Flexibility of NPNA Epitope Expressed on TMV Particles (Mouse Study-3)

Figure 10A:
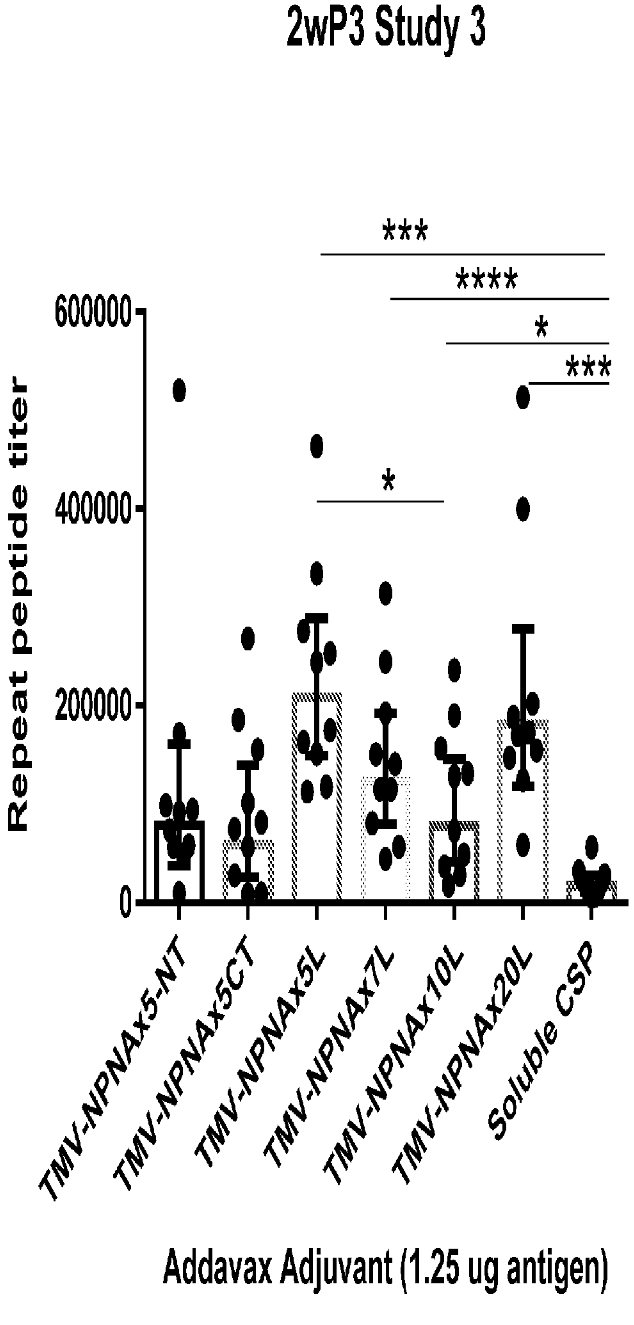
FIG. 10A-10B show immunogenicity and protection data (Mouse Study 3)
Figure 10B:
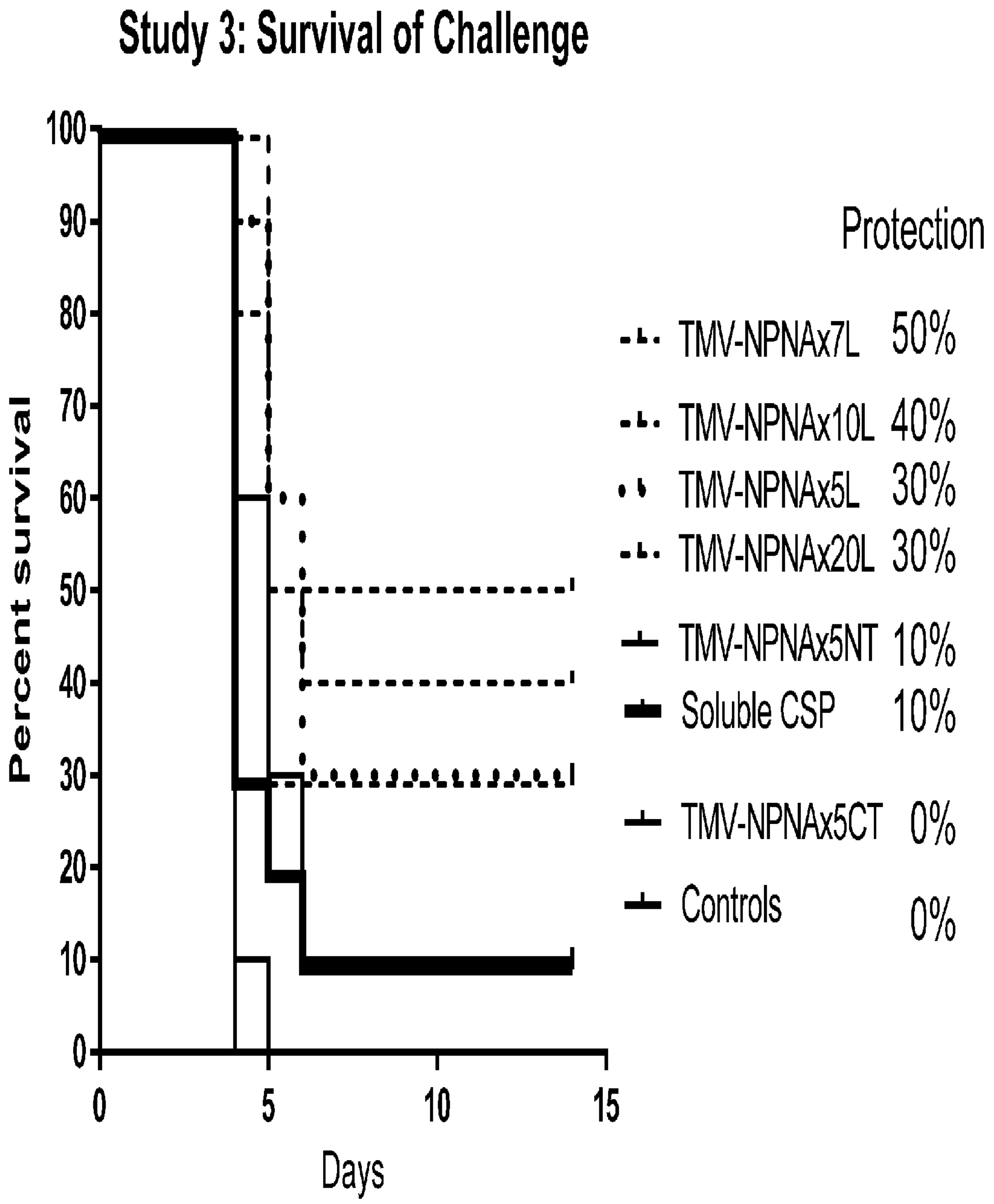

To further confirm the superiority of the particles over soluble protein and to determine the effects of epitope density mice were immunized with TMV-NPNAx5, TMV-NPNAx7, TMV-NPNAx10, TMV-NPNAx20, all on the exposed loop (-L). This experiment also tested the effect of epitope flexibility using the NPNAx5 epitope expressed on the N-Terminal (-NT), C-Terminal (-CT) as compared to the exposed loop (L) (FIG. 10). Soluble CSP again served as a control. Adjuvant Addavax was used with 1.25 μg antigen three times at 3 week intervals. The NANP specific ELISA data at 2 weeks post 3$^{1"11}$ vaccination (2WP3) were compared (FIG. 10A). To determine the functionality of these antibodies, the vaccinated mice were challenged with 3000 trangenic *P. berghei* parasites that harbored the *P. falciparum* CSP gene. The naïve control mice showed 100% infectivity (FIG. 10B).

Delivery Method:

Particulate vaccines (TMV) were compared to a soluble CSP vaccine that contains NPNAx18 epitope. The repeat peptide ELISA titer for the TMV-NPNAx5L, TMV-NPNAx7L, TMV-NPNAx10L and TMV-NPNAx20L were statistically superior to the soluble CSP repeat ELISA titer (FIG. 10A). Upon challenge the soluble CSP that contains 18 copies of the NPNA repeat showed only 10% protection, but TMV particles that contain fewer repeats (NPNAx5, x7 or x10) showed higher protection (30, 50 and 40% respectively) (FIG. 10B).

Epitope Flexibility:

To determine if the flexibility can have an effect on immunogenicity, the NPNAx5 epitope was placed at 3 different locations on the TMV particle. The epitope that was tethered at both ends as an exposed loop (NPNAx5L) had the least flexibility. The N-terminal fusion protein (NPNAx5-NT) or the C-terminal fusion protein (NPNAx5-CT) offered more flexibility to the NPNAx5 epitope. The NPNAx5 epitope on the exposed loop induced higher repeat peptide ELISA titer than the NT and CT particles (FIG. 10A). Furthermore while the NPNAx5-CT protected 0% and NPNAx5-NT protected 10%, the NPNAx5L vaccine protected 30% mice at 2 weeks post challenge period (FIG. 10B). There was also some delay in infection in the NPNAx5L group that was not seen in the NT and CT groups (FIG. 10B).

Epitope Density and Valency:

To determine the epitope density and valency effect on immunogenicity, NPNAx5L, NPNAx7L, NPNAx10L and NPNAx20L TMV particles were compared. All of these particles displayed the epitope on the exposed loop. Surprisingly, the NPNAx5 showed higher repeat peptide ELISA titer than NPNAx7L and NPNAx10L and it was not different from the NPNAx20 group titer, thus there is a critical epitope density and valency that is optimal for immunogenicity (FIG. 10A). No further increase in titer was found beyond the NPNAx5L. Optimum protection was obtained using 5 to 7 repeats (30% to 50% respectively) and that the immunogenicity/protection did not continue to increase indefinitely with increasing epitope density and valency (FIG. 10B).

Example 13. Comparison of Immunogenicity and Protective Efficacy of NPNAx5 and NPNAx7 on TMV and ZMV Particles (Mouse Study-4)

Figure 11A:
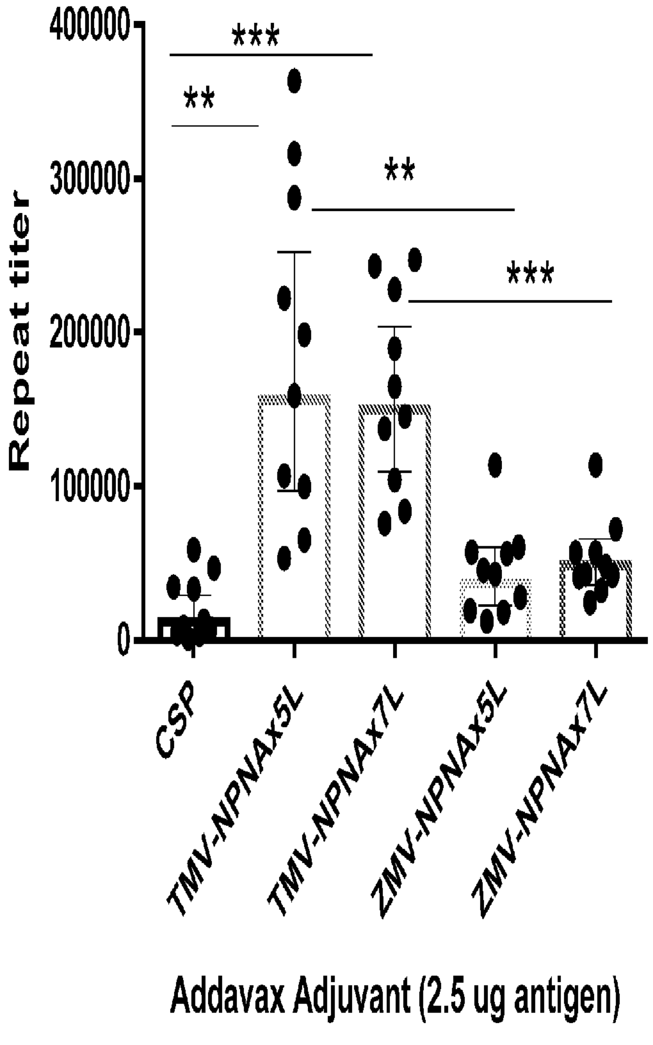
FIG. 11A-11B show immunogenicity and protection data (Mouse study 4)
Figure 11B:
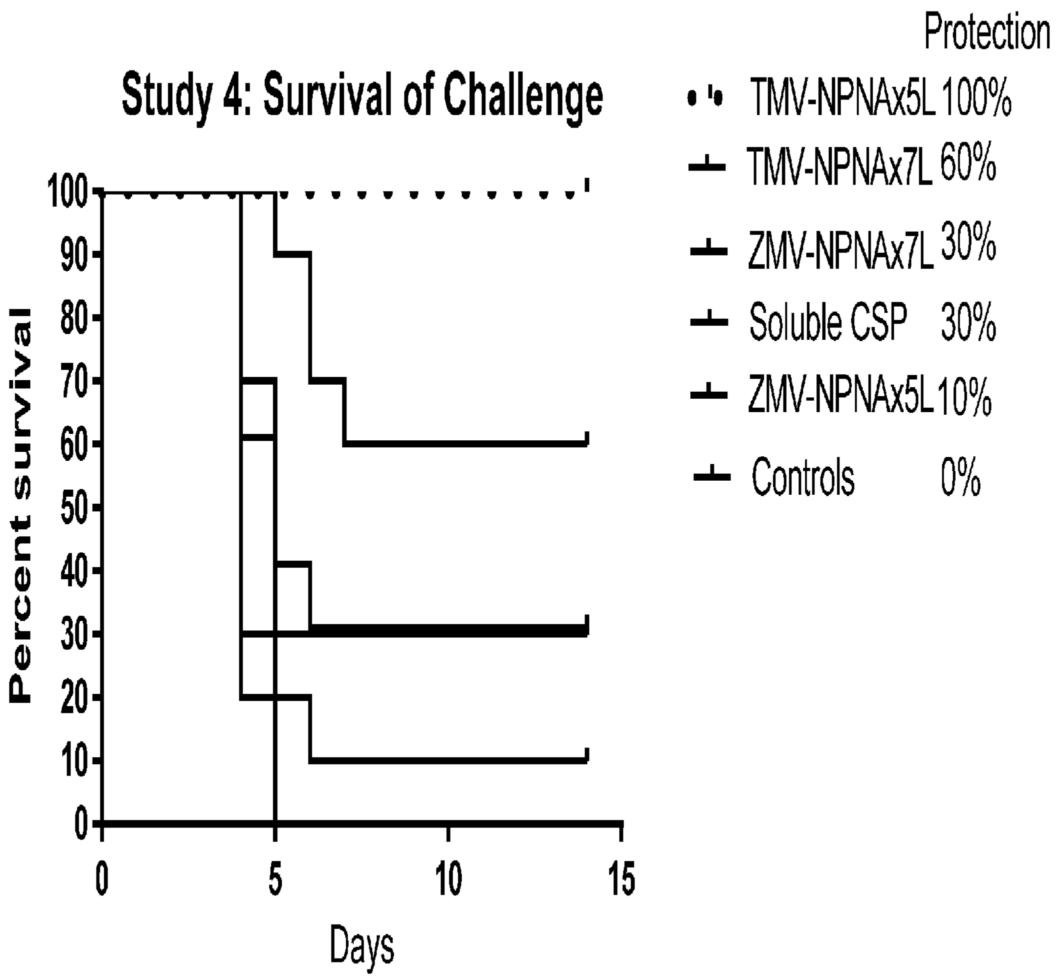

In study-2 (Example 11), the TMV-NPNAx5 vaccine gave 66% protection but it gave only 30% protection in study-3 (Example 12). Further the NPNAx7L appeared to protect better than NPNAx5L in mouse study-3. So the vaccination was repeated with two TMV particles NPNAx5L and NPNAx7L using three doses of 2.5 ug (rather than 1.25 ug per dose). This study also compared the NPNAx5L and NPNAx7L epitopes displayed on the ZMV backbone to see if epitope density data from TMV and ZMV systems match up. Soluble CSP group was again used as the control. Adjuvant Addavax was again used. The repeat specific ELISA data at 2 weeks post 3$^{rd}$ vaccination (2WP3) were compared (FIG. 11A). To determine the functionality of these antibodies, the vaccinated mice were challenged with 3000 trangenic *P. berghei* parasites that harbored the *P. falciparum* CSP gene. The naïve control mice showed 0% protection (FIG. 11B).

Delivery Method and Platform:

In this final experiment, it was conclusively confirmed that the TMV particle vaccine was vastly superior to the soluble protein vaccine. Both the NPNAx5L and NPNAx7L epitopes on the TMV particle showed statistically significantly higher titers and percent protection (100% and 60% respectively) compared to soluble CSP (30% protection), even though the soluble CSP contained NPNAx18 epitope (FIG. 11B). The clear superiority of the TMV particle over the ZMV particle vaccine was also reproduced, as the repeat peptide ELISA titers and protection of the TMV-NPNAx5L (100% protection) were higher than ZMV-NPNAx5L (10% protection) and likewise the TMV-NPNAx7L titers and protection (60%) were higher than ZMV-NPNAx7L titers and protection (30%) (FIG. 11A).

Epitope Density and Valency:

To confirm the effects of epitope density, the NPNAx5L, and NPNAx7L immunogenicity and protection were compared on both the TMV and ZMV particles. There was no difference in NPNAx5L and NPNAx7L repeat peptide ELISA titers on either the TMV or the ZMV platforms. However in terms of protection the NPNAx5L protected better (100%) than the NPNAx7L (60%) on the TMV particle (FIG. 11). This high level protection was not observed with ZMV as both the ZMV vaccines showed low protection (10 and 30%). Hence, it was confirmed that adding more repeats beyond NPNAx5 does not increase immunogenicity on the TMV backbone.

Example 14. Adjuvant Containing Additional Immune-Stimulants

Figure 12A:
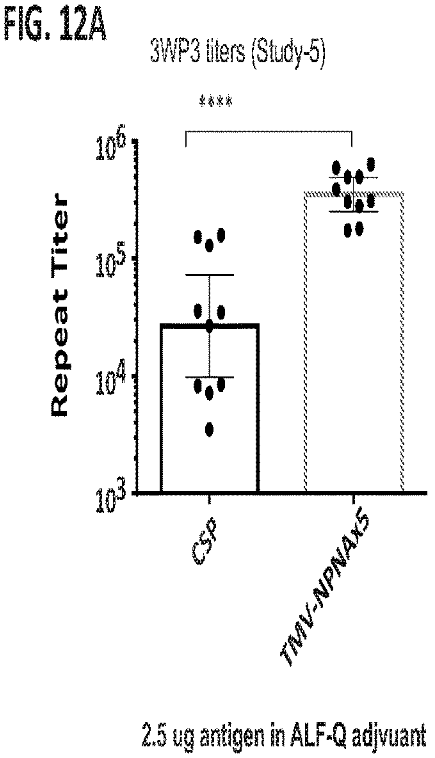
FIG. 12A-12D show results of tests with adjuvants utilizing additional immune-stimulants.
Figure 12B:
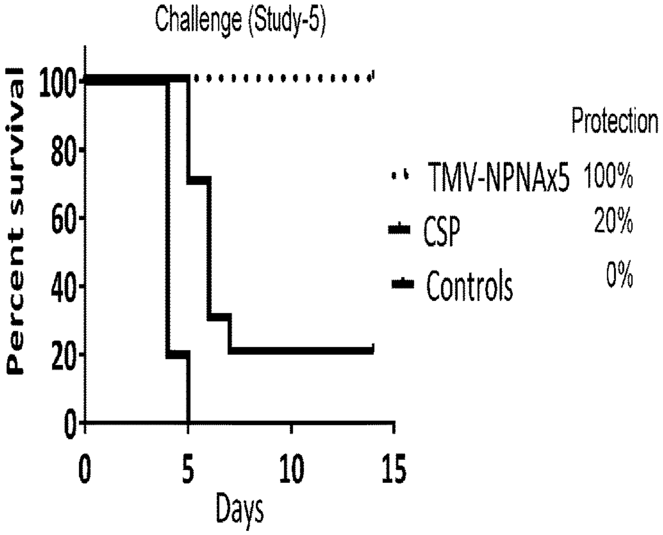
Figure 12C:
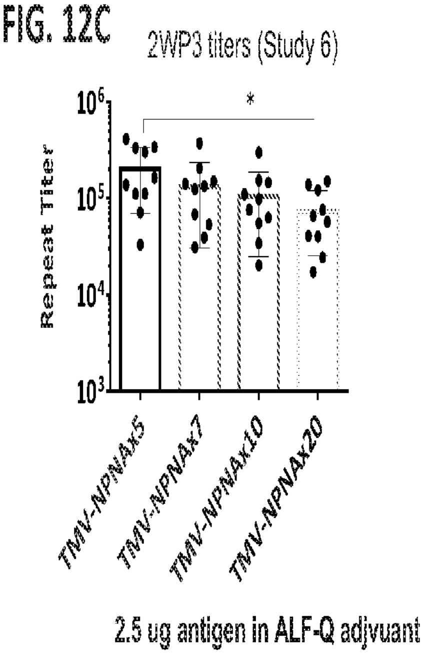
Figure 12D:
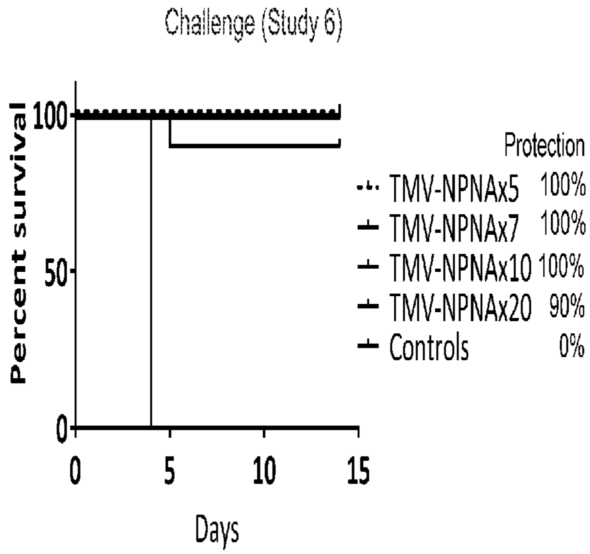

Variable degrees of protection were observed in various Addavax adjuvanted TMV vaccine trials in the mouse protection model (see Examples above). Based on this, TMV based vaccines were further tested with molecular adjuvants containing additional immune-stimulators to assess response. Unlike Addavax, that does not contain immune-stimulants, liposomal adjuvants containing TLR4 agonist and QS21 have been shown to be excellent drivers of Th1-type immune response. Examples of such adjuvants are: AS01 (GlaxoSmithkline Vaccine, Rixensaart Belgium), ALF-Q (Walter Reed Army Institute of Research, Silver Spring Md.) and GLA-SE (Infectious Disease Research Institute, Seattle). The TMV vaccines were tested in a liposomal formulation containing a TLR agonist 3D-PHAD (Avanti Polar Lipids) and QS21 (Desert King Pharmaceuticals). In the first trial, 3 doses of 2.5 ug CSP vaccine were compared to 2.5 ug TMV-NPNAx5. Statistically superior antibody titers were observed in the TMV-NPNAx5 group as compared to CSP (FIG. 12A). Following parasite challenge only 20% protection was seen for soluble CSP as compared to 100% protection in the TMV-NPNAx5 group (FIG. 12B). In a second trial, 3 doses of 2.5 ug TMV-NPNAx5, TMV-NPNAx7, TMV-NPNAx10 and TMV-NPNAx20 were compared in a Liposomal molecular adjuvant (ALF-Q). All four vaccines showed no statistical difference in antibody titers, as was shown using Addavax adjuvant (FIG. 12C). Following challenge, TMV-NPNAx5, TMV-NPNAx7, TMV-NPNAx10 and TMV-NPNAx20 conferred very strong protection—100%, 100%, 100% and 90% protection, respectively (FIG. 12D). The superiority of TMV induced titers and high level protection was upheld using multiple adjuvants.

Example 15. Rhesus Trial with TMV-NPNA Vaccines

Figure 13A:
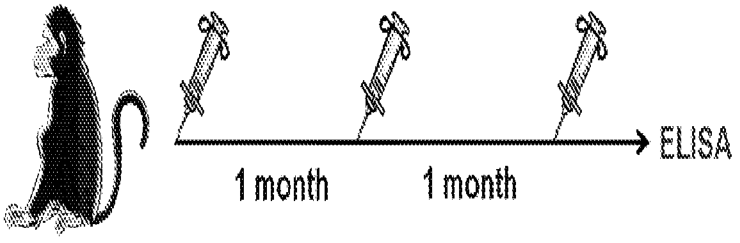
FIG. 13A-13C show the Rhesus trial with TMV-NPNA vaccines.
Figure 13B:
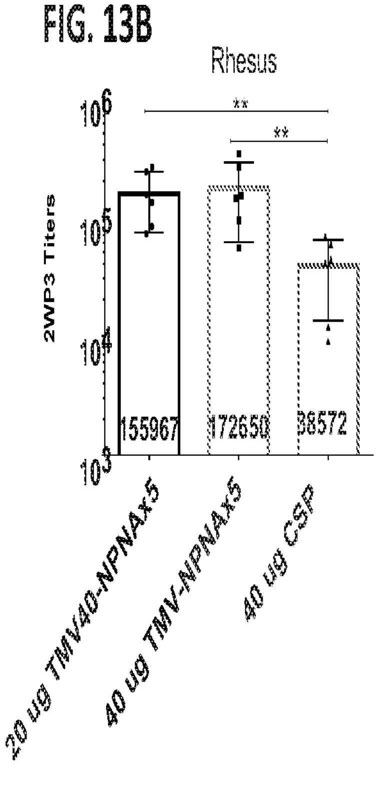
Figure 13C:
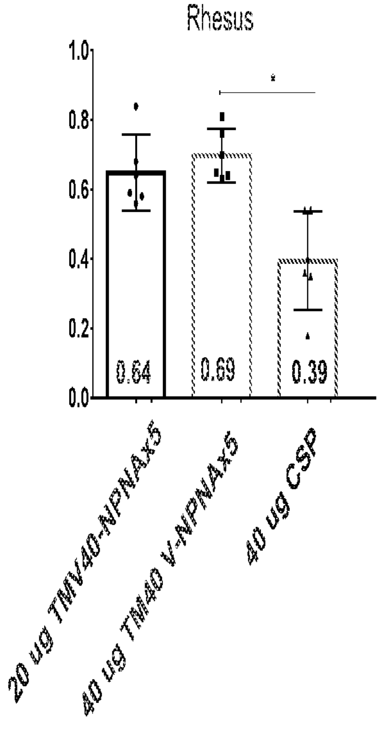
Figure 14:
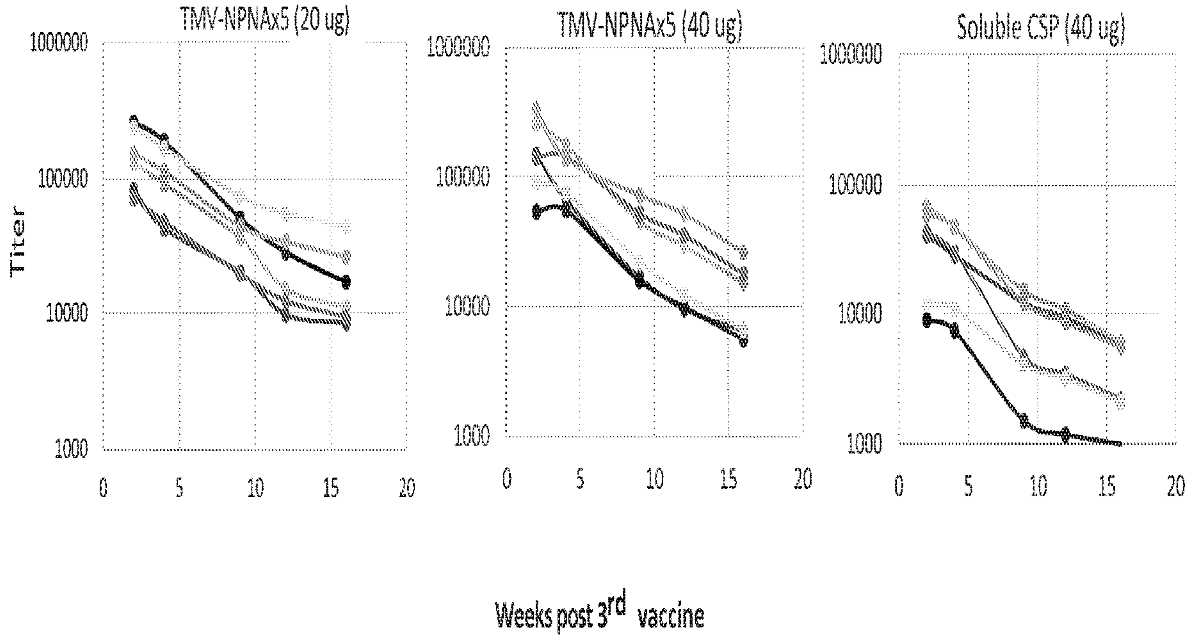
FIG. 14 shows the drop in NANP titers recorded at multiple time points after the $3^{rd}$ immunization for TMV-NPNAx5 and CSP vaccines in Rhesus monkeys. Each line represents titer in individual animal.

In order to determine if the observations made in mice would be upheld in higher mammals, tests were conducted in Rhesus monkeys. The animals were vaccinated with 3 doses of 20 and 40 ug of TMV-NPNAx5 (exposed loop form). The comparator group of monkeys received 40 ug soluble CSP in ALF-Q adjuvant (FIG. 13A). After the 3rd vaccine dose, the TMV-NPNAx5 titers for both the 20 and 40 ug groups was about 4-fold higher than soluble CSP (FIG. 13B; both p values $<0.01$). The avidity index of the sera was determined as an indicator of binding strength of the induced antibodies. The avidity index of the two TMV-NPNAx5 groups was about 2-fold higher than soluble CSP and the difference between the 40 ug TMV-NPNAx5 and CSP was statistically significant (FIG. 13C). The drop in titers was monitored in the 16 week period following the 3rd dose of the vaccine in Rhesus (FIG. 14). The titers in all monkeys (TMV-NPNAx5 and CSP) dropped steeply immediately after the 3rd dose, but by week 12, the drop of titers slowed down such that the 20 ug TMVxNPNAx5 group plateaued at an endpoint titer >10,000. In contrast, the soluble CSP group titers stayed well below the end-point titer of 10,000 and continued dropping. Thus TMVxNPNAx5 not only induced higher levels of repeat antibodies, but these antibodies persisted at significantly higher levels than soluble CSP over 16 weeks post 3rd dose.

Example 16: Mechanism of Antibody Enhancement

Figure 15A:
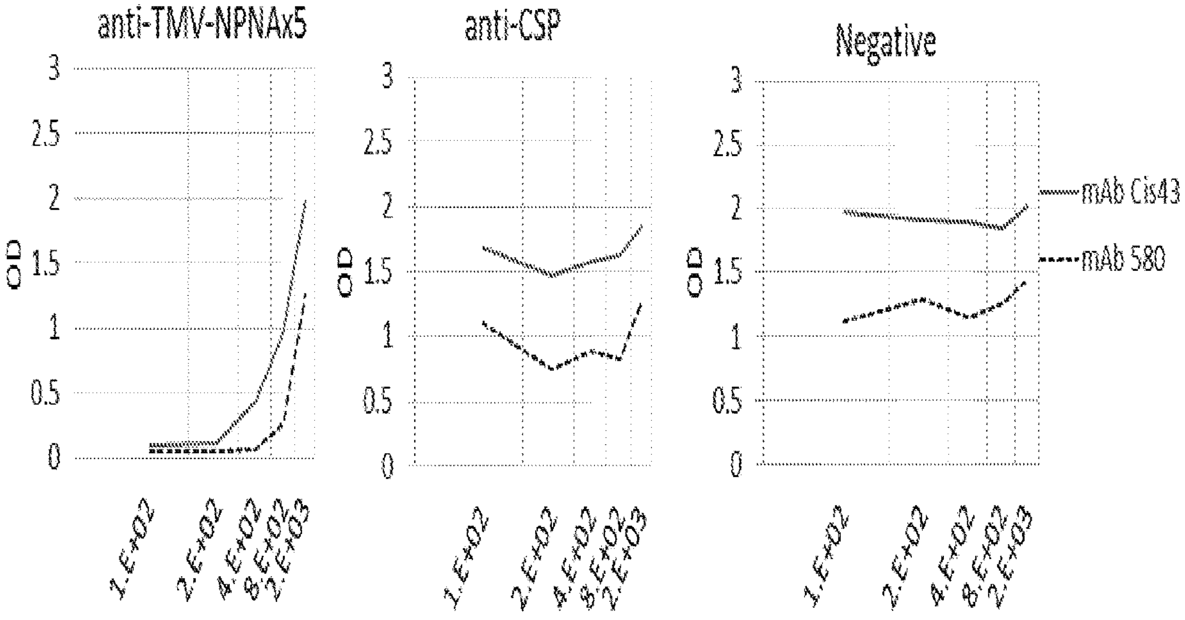
FIG. 15A-15C shows monoclonal antibody competition ELISA using 6 published monoclonal antibodies against the repeat region [10-13].

Recently reported human mAbs were shown to bind to the repeat region of CSP [10-13]. We expressed these mAbs in mammalian cells and used purified mAbs in a competition ELISA (FIG. 15A). Serum from a mice vaccinated with CSP (Addavax), TMV-NPNAx5 (Addavax) or a naïve control was used to compete out the mAb binding to a (NPNA)6 peptide bound to the ELISA plate. Fine mapping using these inhibitory mAbs revealed that soluble CSP did not induce high titers of functional repeat specific antibodies as evidenced by the inability of anti-soluble CSP serum to compete out functional mAb binding to the peptide on the plate, similar to the negative control serum (FIG. 15A). In contrast, TMV-NPNAx5 antiserum competed with the functional mAbs to various degrees, showing that mouse, vaccination with a TMV based vaccines can induce functional antibodies of novel specificities that are not induced by soluble antigen.

Figure 15B:
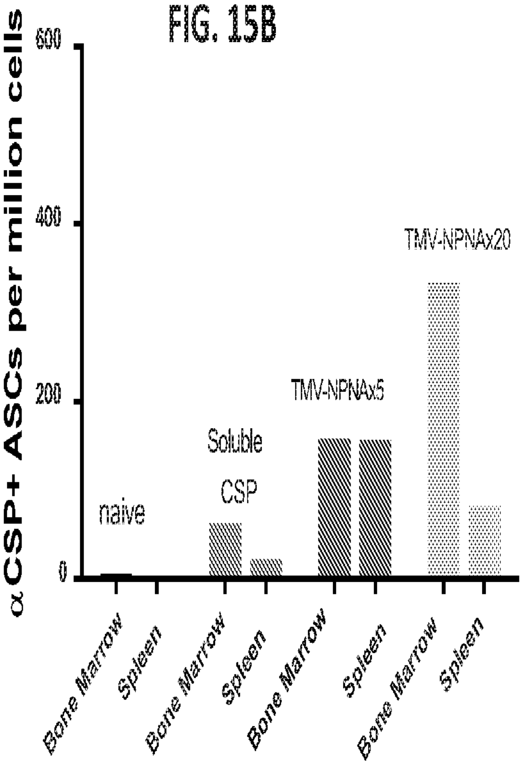
Figure 15C:
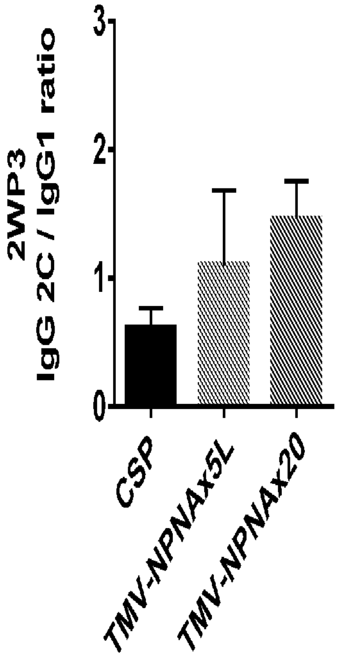

Next, the mechanism of TMV induced immune-enhancement in mice was determined. The number of CSP specific antibody secreting cells (ASCs) present in spleen and bone marrow from Addavax-adjuvanted TMVxNPNAx5, TMV-NPNAx20 and soluble CSP vaccinated mice were determined at 5 weeks post $3^{rd}$ vaccination (FIG. 15B). Both TMV based vaccines elicited higher numbers of CSP-specific ASCs as compared to soluble CSP in bone marrow and spleen. Similar levels of splenic ASCs were elicited by TMV-NPNAx5 and TMV-NPNAx20. There were, however, higher levels of bone marrow derived ASCs in the TMV-NPNAx20 vaccinated mice were seen. These results suggest that increasing epitope density or valency by adding higher number of NPNA repeats may favor the formation of the longer-lived ASCs in the bone marrow. There was no significant difference in the levels of cytophilic antibodies (IgG2c/IgG1 titer ratio) induced by the TMV-NPNA based vaccines and soluble CSP (FIG. 15C). These data suggest that immune-enhancement by TMV display may rely upon structural stabilization of epitopes that allow novel antibodies with higher ASCs to be produced in spleen and bone marrow that survive longer than soluble CSP induced ASCs.

Example 17. Development of a Process to Manufacture TMV-NPNAx5 Vaccine as a Soluble Protein in *E. coli*

Figure 16A:
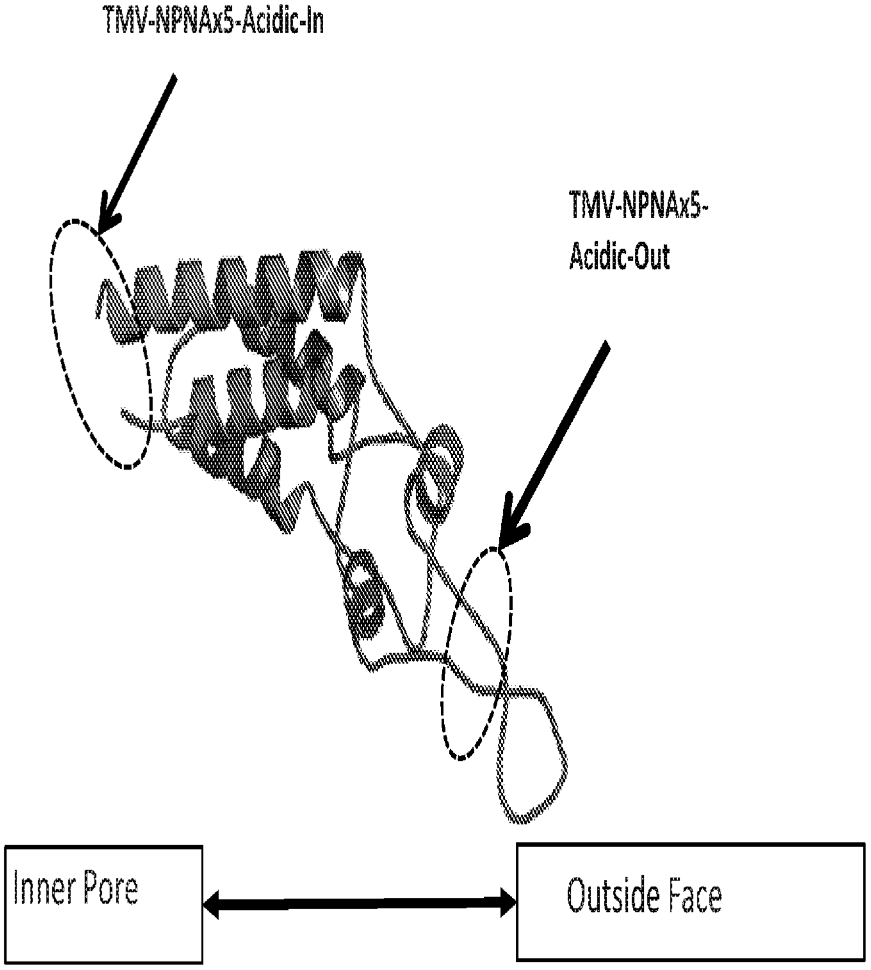

TMV assembles and disassembles through interactions between high-radius and low-radius carboxylates located around the solvent-exposed face of the TMV monomer (FIG. 16A). Wang et al (1998) [17] and Lu et al. (1996) [18] showed that low-radius carboxylates (E95, E97, E106 and D109) are far more important than high-radius carboxylates in modulating the equilibrium between assembly and disassembly. The initial TMV-NPNAx5 construct produced herein had all four low-radius carboxylates deleted to promote assembly; however, this resulted in an insoluble particle that required in vitro refolding. The loss of 4 acidic residues, the addition of a hexa-histidine tag, and a NPNAx5 epitope, raised the pI of the monomeric TMV by about 3 pI units (above the native TMV protein pI). The dependence of TMV stability on its pI has also been reported by Bendahmane et al. (1999) [19] using plant expressed TMV. Zhang et al. (2004) [20] showed that adding acidic residues (carboxylates) to immunoglobulins, expressed in *E. coli* can significantly improve its folding.

Figure 17A:
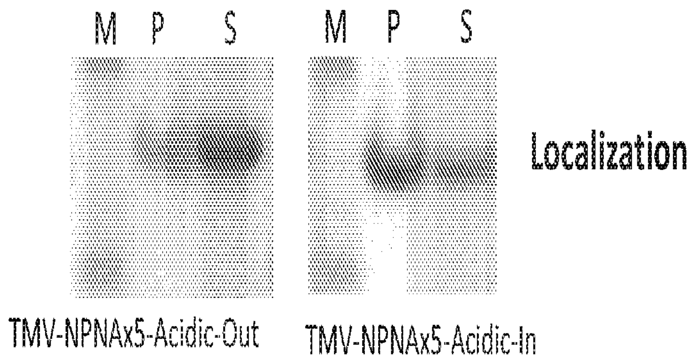
Figure 17B:
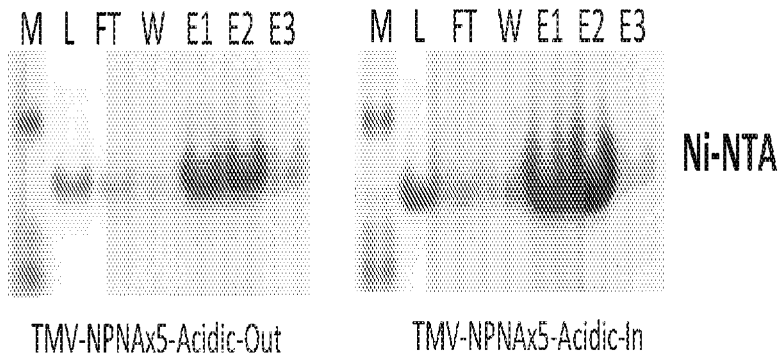
Figure 17C:
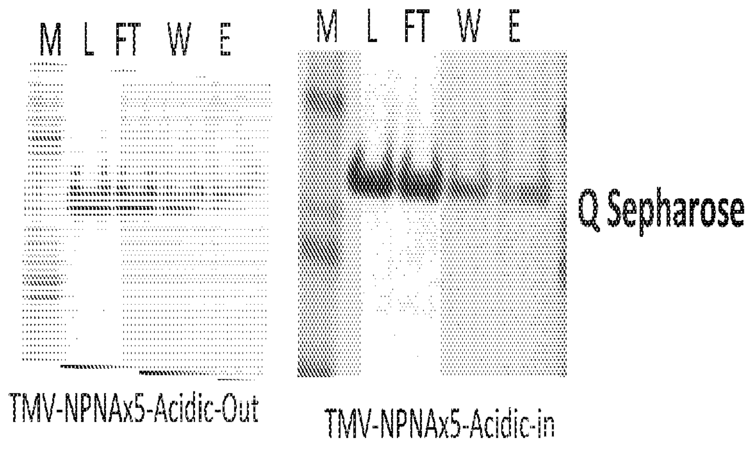
Figure 18A:
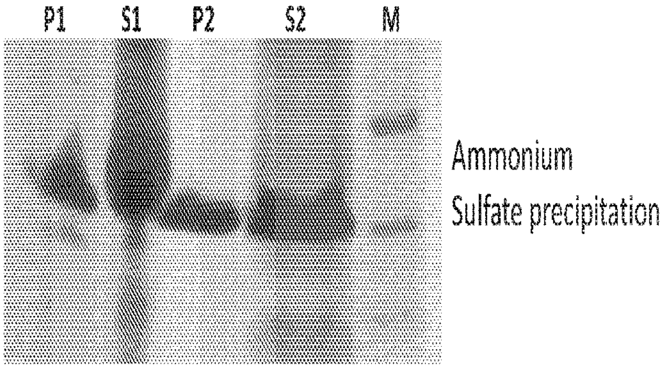
FIG. 18A-18C illustrates native purification (non-denaturing) of the TMV construct containing the acidic-out from the soluble fraction of *E. coli*.
Figure 18B:
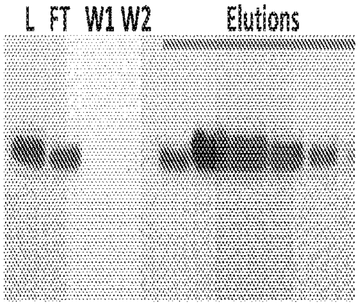

In an attempt to address the problem of insoluble TMV particle expression, native and non-native carboxylates were inserted into the TMV sequence and the resulting constructs were tested to determine solubility and self-assembly in *E. coli*. In one of the constructs, identified as TMV-NPNAx5-Acidic-out (SEQ ID NO: 19, capsid as SEQ ID NO: 21), two non-native acidic residues were added, flanking the NPNA epitope, and located on the outside of the folded particle (FIG. 16A, 16B). Another construct, identified as TMV-NPNAx5 -Acidic-in (SEQ ID NO 20, capsid as SEQ ID NO 22), had two low-radius carboxylates restored in the inner pore of TMV (FIG. 16A, 16B). Expression in *E. coli* was carried out at 30° C. for both the acidic residue containing constructs (FIG. 17A). Using the insoluble pellet under denaturing conditions, the two proteins were purified on Ni-NTA (FIG. 17B) and anion-exchange column (FIG. 17C). Yield of the particles per gram of *E. coli* paste was: 18 mg for TMV-NPNAx5-Acidic-out; 12.5 mg for TMV-NPNAx5-Acidic-in, which were much better than the 1.2 mg per gram yield of the original TMV-NPNAx5 where the carboxylates had been deleted. The electron micrographs confirmed that TMV-NPNAx5 -Acidic-out formed disks while the TMV-NPNAx5-Acidic-in formed both disks and rods (FIG. 17D). Due to the higher yield, the TMV-NPNAx5-Acidic-out construct was purified from the soluble fraction (FIG. 18). A combination of ammonium sulfate precipitation (FIG. 18A) and anion-exchange chromatography (FIG. 18B), provided up to 11.6 mg TMV-NPNAx5

Figure 18C:

-Acidic-out particles per gram wet cell paste that formed particles as evidenced by electron microscopy (FIG. 18C). The data shows a way to produce TMV based vaccines as soluble proteins by adding the non-native acidic residues on either side of the expressed epitope.

Example 18. General Particulate Display of Vaccine Epitopes

Figure 19A:
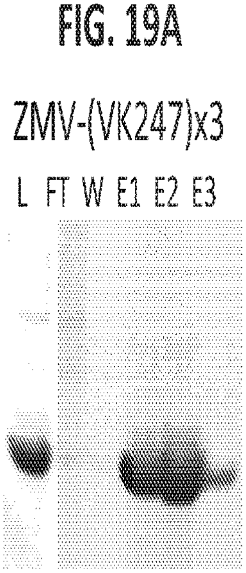
FIG. 19A-19E illustrates *P. vivax* vaccine constructs on the Tobamovirus platform. ZMV-(VK247)x3 (FIG. 19A) and ZMV-(VK210)x5 (FIG. 19B) purification under native conditions. After ammonium sulfate precipitation of ZMV-(VK247)x3 and ZMV-(VK210)x5 protein (20 and 40% w/v respectively) from the soluble fraction was dialyzed in 20 mM Tris, 20 mM sodium chloride pH 9.0 to remove residual ammonium sulfate. The dialysis product was loaded onto Q sepharose and eluted with 200 mM sodium chloride. (M=Marker, L=Load, FT=Flow through, W=Wash, E=Elutions).
Figure 19B:
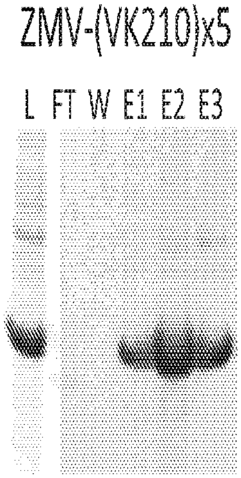
Figure 19C:
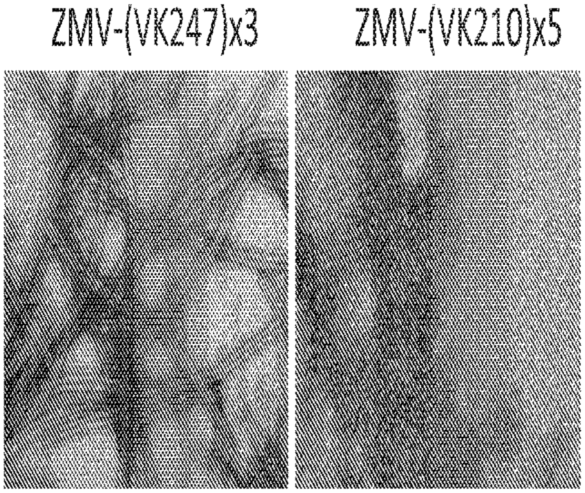
Figure 19D:
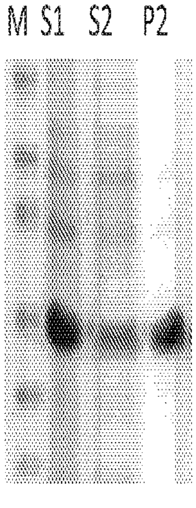
Figure 19E:
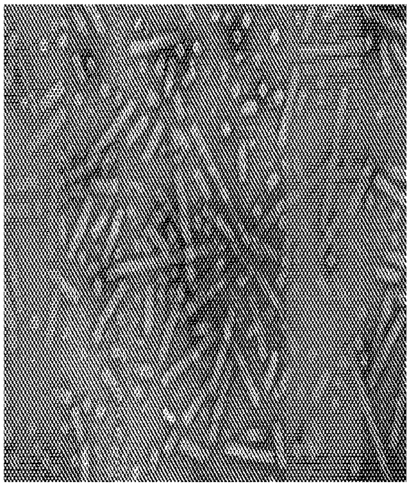

The Tobamovirus platform described herein can be used for general particulate display of vaccine epitopes, and is not limited to PfCSP. Particles produced using Sequence IDs T2, T4, T5, T7, T8, T9, T10, T11, T14, T21, T22 displayed the *P. falciparum* CSP (NPNA)n epitope on the TMV and ZMV platforms. Tobamovirus family particles have also been tested for the display of other vaccine antigens not limited to PfCSP. Based upon the success of the PfCSP repeat epitope NPNA displayed on Tobacco mosaic virus and Zucchini Green Mottle Mosaic Virus, we next determined whether Tobamovirus platforms could be amenable to the display of other antigens. Two repeat epitopes from the central region of *P. vivax* CSP were selected. These two repeats are known as Type I and Type II repeats from PvCSP strains VK210 and VK247, respectively [21]. These repeats were inserted as "exposed loop" for both TMV and ZMV backbones (SEQ ID 23, SEQ ID 24 and SEQ ID 25). ZMV-(VK210)x5 and ZMV-(VK247)x3 could both be purified from the soluble fraction using ammonium sulfate precipitation and Q sepharose chromatography (FIG. 19A, FIG. 19B). ZMV-VK210-x5 formed disk-like particles and ZMV-VK247-x3 formed rod-like particles as seen by electron microscopy (FIG. 19C). For Tobacco Mosaic Virus, only the VK247 insertion produced particles as seen by ammonium sulfate precipitation and Electron microscopy (FIG. 19D, 19E). These data show that Tobamovirus platforms can be utilized to display a versatile array of antigens. Epitopes of a dual stage malaria protein *P. falciparum* AMA1 (sequence IDs, T32, T33, T34) have also been designed.

Example 19. Expression and Purification of GST Fusion Proteins Representing Various Regions of *P. falciparum* CSP: PCR Amplified the N-Terminal, Repeat, and the C-Terminal Regions of *P. falciparum* CSP (3D7) Using Specific Primers PCR products were cloned into pGEX-His vector (GE health Care Life Sciences) in frame with a GST tag. The expression induced with 0.1 mM IPTG in BL21 (DE-3), and confirmed by Western blot using polyclonal CSP and monoclonal GST antibodies. Proteins (including GST control) were purified on Glutathione-Sepharose column and eluted with 10 mM reduced glutathione in 3×PBS pH 8.0. Peak fractions were dialyzed in 1×PBS and stored at −80° C. until vaccination.

Example 20. Expression and Purification of TMV/ZMV Particles Under Native Conditions Capsid genes containing the NPNA epitope were synthesized commercially, cloned into *E. coli* expression pD451SR plasmid and transformed into BL21(DE3) cells. A typical culture was grown in 1 L terrific broth at 37 C in the presence of 25 ug Kanamycin at 150 RPM until $OD_{600}$ between 0.6 and 0.8. Protein expression was induced with 0.03 mM IPTG for 22 h at 30° C. and cells were harvested by centrifugation, and stored at −80° C. For purification, cells were re-suspended in 50 mM sodium phosphate dibasic pH 7.0 and lysed by high pressure microfluidization. The lysate was then centrifuged at 26,000×g for 30 minutes. The supernatant was then equilibrated to room temperature for ammonium sulfate precipitation. Ammonium sulfate precipitation was performed at a final saturation of 18-40%. The precipitate was pelleted by centrifugation (13000 RPM for 30 minutes) and then re-suspended in 20 mM Tris, 20 mM sodium chloride, pH 7.5. This protein was then dialyzed against the same buffer to remove ammonium sulfate using a Slide-a-lyzer 10K MWCO cassette. Proteins was subsequently loaded onto a Q sepharose column and eluted stepwise with 20 mM Tris containing 150-400 mM sodium chloride. The resulting fractions were dialyzed against 20 mM Tris, 20 mM sodium chloride, pH 7.5 and stored at −80° C.

Example 21. Expression and Purification of TMV Particles Under Denaturing Conditions Genes for TMV capsid containing the NPNA epitope were commercially optimized for high level expression, cloned into pD451 SR expression plasmid and transformed into BL21(DE) cells. Cells were typically grown in 1 L culture in shake flasks, and induced at an $OD_{600\ nm}$ of 0.7 using 0.1 mM IPTG at 37° C. After 2 hr induction the cells were harvested by centrifugation and stored at −80° C. In a typical laboratory grade production run, 2 grams of *E. coli* paste was suspended in 100 ml of 20 mM Tris, 20 mM NaCl pH 9.0 (Buffer A). One ml of protease inhibitor cocktail was added just before microfludization. After microfludization, lyzed cells were centrifuged at 13,000 rpm for 30 min and pellet was solubilized in 20 mM Tris, 20 mM NaCl, 7M urea pH 9.0 (Buffer B). After resuspension the urea solution was centrifuged at 13,000 rpm for 30 min. Resultant supernatant was collected, and loaded onto 6 ml Ni-NTA column equilibrated in Buffer B. The column was washed with 60 ml of Buffer B, and 70 ml of Buffer B containing 20 mM imidazole. Finally, protein was eluted with 250 mM imidazole in Buffer B. The peak fractions of Ni-NTA column were pooled, and diluted 10× with Buffer B. This dilute protein was loaded onto 3 ml Q-Sepharose column equilibrated in Buffer B. Column was washed with 50 ml equilibration buffer, and protein was eluted with 1M NaCl gradient. Most of the protein was in the flow-thru. $OD_{280}$ of the flow-thru was measured, and diluted to 0.1 with Buffer B. 1 00 ml of this protein solution was dialyzed against 4.5 Lt. of Buffer A containing 0.05% β-mercaptoethanol overnight at 4° C. The following day Buffer A was exchanged with 4.5 Lt. of 20 mM Phosphate, 20 mM NaCl pH 7.4 (Buffer C). After 8 hrs, dialysis buffer was replaced with 4.5 Lt. of fresh Buffer C, and continued overnight. Next day, the protein solution was filtered through 0.22 μM filter, concentrated on a Centricon concentrator to 15 ml, and was further centrifuged to remove any precipitate. Particle size was determined by dynamic light scattering on a Malvern Zetasizer NanoS, and by electron microscopy. The presence of the NPNA epitope on the particles was confirmed by a western blot using polyclonal antibodies against CSP. Protein was stored at −80° C. until further use. Endotoxin content was measured using LAL method (Associates of Cape Cod).

Example 22. Mouse Vaccination

Six- to eight-week old female C57Bl/6 (H-2b) mice were purchased from the Jackson Laboratories (Bar Harbor, Me.). All procedures were reviewed and approved by the Walter Reed Army Institute of Research's Animal Care and Use Committee (Protocol number:16-MVD-24). Vaccines were formulated in Addavax adjuvant (Invivogen, San Diego, Calif.) or ALF-Q (WRAIR). Female C57Bl/6J mice (The Jackson Laboratory, Bar Harbor, Me., USA) were immunized intramuscularly (IM) with 0.05 ml of the vaccines containing 1.25 or 2.5 ug of antigen by injection in rear thighs at 0, 3, and 6 weeks.

Example 23. Malaria Parasite Challenge

Protective efficacy of vaccines was assessed using transgenic *P. berghei* (Tr-Pb) sporozoites expressing a functional full-length *P. falciparum* CSP gene. Animals were challenged 15 days after the last immunization with 100 μL intravenous (IV) injection of 3000 Tr-Pb sporozoites into the caudal vein, as described by Porter et al. [9]. Blood-stage parasitemia was detected by microscopy of giemsa-stained thin blood smear. Animals were considered protected if parasitemia was not detected during a two-week observation period immediately following challenge. The animals were bled three weeks after the first and second immunizations and on the day before challenge. Humane euthanasia was performed by carbon dioxide displacement. Compressed gas was supplied to the chamber using a pressure-reducing regulator and a flow meter to maintain a displacement rate of ~20% of the chamber volume/min, this procedure was followed by cervical dislocation.

Example 24. Rhesus Vaccination

Colony-bred adult rhesus macaques of Indian origin (*Macaca mulatta*), were housed at the WRAIR animal facility and used under the IACUC-approved protocol. Macaques were malaria naïve and had been used in a dengue study previously. All animals had no overt clinical signs of illness, testing negative for Macacine herpesvirus 1, measles, Simian Retrovirus, Simian Immunodeficiency Virus, Simian T-cell Leukemia Virus and tuberculin skin test. Animals were pair-housed in a controlled environment as previously described, in accordance with WRAIR Veterinary Service Programs standard operating procedures. Research was conducted under an IACUC-approved animal use protocol in an AAALAC accredited facility in compliance with the Animal Welfare Act and other federal statutes and regulations relating to animals and experiments involving animals and adheres to principles stated in the Guide for the Care and Use of Laboratory Animals, NRC Publication, 2011 edition.

Three groups of 6 Rhesus macaques were given CSP or TMV-NPNAx5 vaccines in 1 ml ALF-Q adjuvant. Antigen was suspended at 2× the desired antigen concentration and combined with an equal volume of ALF-Q. The formulation was rolled on a rotary platform for 1 hr±20 m before administration. Macaques were anesthetized with Ketamine HCl at 5-10 mg/kg in combination with acepromazine at 0.05-0.1 mg/kg. A small patch was shaved and vaccines were administered intramuscularly (IM) in the outer thigh muscle. Injection sites were alternated between right and left thigh for each administration day. Rhesus macaques were vaccinated three times at 1 month interval and bled 2 weeks after the $3^{rd}$ dose for serology

Example 24. ELISA

Immulon 2HB 96-well flat bottom microtiter plates (Thermo Scientific, Rochester, N.Y., USA) were coated with (NANP)6 peptide at 100 ng/well in PBS overnight at 4° C. All subsequent incubations were at +22° C. Plates were washed three times with PBS/0.05% Tween-20 (wash buffer) and blocked 1.5 h with 0.5% casein/PBS/1% Tween-20. Plates were washed three times and incubated 2 h with serially diluted sample in 0.5% casein/PBS/0.05% Tween-20 (dilution buffer). Plates were washed three times and 25 ng/well of secondary antibody (goat anti-mouse IgG-HRP) in dilution buffer was incubated for 1 h. Plates were then washed a final four times before being developed for 1 h with ABTS 2-component substrate (KPL) and stopped by adding SDS to a final 2% concentration. Absorbance was read at 414 nm ($OD_{414}$) Antibody titer was determined at the concentration where $OD_{414}$=1.000, using Gen5™ 4-parameter nonlinear regression (BioTek, Winooski, Vt., USA).

Example 25. Antibody Secreting Cell (ASC) ELISPOT

Mice shown to be protected in FIG. 10 were selected for the antibody secreting cell (ACS) ELISPOT at 3 weeks post challenge time point. Vaccinated mice selected for this assay had comparable FL CSP antibody titers. Bone marrow and spleens from TMV-NPNAx5 (n=2), TMV-NPNAx20 (n=2), soluble CSP (n=1) and naïve control (n=1) were processed into a single cell suspensions and incubated on FL-CSP coated ELISPOT plates for 4 hours at +37° C., 5% CO2. Cells were removed, and the presence of antibody "spots" correlating to CSP-specific ASC were developed using an ELISPOT detection kit and counted using an AID ELISPOT reader. The resulting numbers of detected ASC were reported as spots per $10^6$ plated cells.

Example 26. Inhibition of Liver Stage Development Assay (ILSDA)

The NF54 strain of *Plasmodium falciparum* (Pt) sporozoites were mixed (1:100 dilution v/v) with anti-repeat region CSP monoclonal NFS1 or polyclonal serum against CSP, GST-Nterm, GST-repeat, GST-Cterm or GST control and incubated at room temperature for 20 minutes. These sporozoite-antibody mixtures were then introduced into the wells containing cryopreserved human hepatocytes (BioReclamation IVT, Baltimore Md.) and incubated at 37° C. for 3 hours to allow sporozoites to infect hepatocytes. After the 3 hour incubation period, hepatocytes were washed with fresh culture media to remove non-invaded sporozoites and incubated at 37° C. for 96 hours. The RNA from the cells was then purified for downstream quantitative real-time PCR (qRT-PCR) analysis. Pf specific 18s rRNA level was quantified to determine the level of inhibition of liver stage development. Inhibition of >2 logs as compared to no serum control is generally considered to induce sterile protection in mice.

Example 27: Statistical Analysis

Rhesus data was analyzed as the mean group value for each parameter. ELISA titers were log transformed and analyzed by ANOVA with Tukey's correction (GraphPad Prism software, La Jolla, Calif.). Statistical significance is indicated on figures: *($p<0.05$), ($p<0.01$), *($p<0.001$) or ****($p<0.0001$).

INCORPORATION BY REFERENCE

All publications and patents mentioned herein are hereby incorporated by reference in their entirety as if each individual publication or patent was specifically and individually indicated to be incorporated by reference.

While specific aspects of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

SEQUENCES

Tobacco Mosaic Virus (TMV) native coat protein

SEQ ID NO: 1

MSYSITTPSQ FVFLSSAWAD PIELINLCTN ALGNQFQTQQ ARTVVQRQFS EVWKPSPQVT

VRFPDSDFKV YRYNAVLDPL VTALLGAFDT RNRIIEVENQ ANPTTAETLD ATRRVDDATV

AIRSAINNLI VELTRGTGSY NRSSFESSSG LVWTSSPAT.

TMV coat protein circular permutant (not native):

SEQ ID NO: 2

MHHHHHHTRR VDDATVAIRC AINNLIVELI RGTGSYNRSS FESSSGLVWT SGPAGEGSYS

ITTPSQFVFL SSAWADPIEL INLCTNALGN QFQTQQARTV VQRQFSEVWK PSPQVTVRFP

DSDFKVYRYN AVLDPLVTAL LGAFDTRN.

Zucchini green mottle mosaic virus (ZMV) native coat protein:

SEQ ID NO: 3

MPYSTSGIRS LPAFSKSFFP YLELYNLLIT NQGAALQTQN GKDILRESLV

GLLSSVASPT SQFPSGVFYV WSRESRIAAL IDSLFGALDS RNRAIEVENP

SNPSTGEALN AVKRNDDAST AAHNDIPQIL SALNEGAGVF DRASFESAFG

LVWTAGSSTS S.

Zucchini green mottle mosaic virus (ZMV) coat protein circular permutant (not native):

SEQ ID NO: 4

MHHHHHHKRN DDASTAAHND IPQILSALNE GAGVFDRASF ESAFGLTWTG

SSYSTSGIRS LPAFSKSFFP YLELYNLLIT NQGAALQTQN GKDILRESLV

GLLSSVASPT SQFPSGVFYV WSRESRIAAL IDSLFGALDQ E.

TMV-NPNAx3-L:

SEQ ID NO: 5

MHHHHHHTRR VDDATVAIRS AINNLIVELI RGTGSYNRSS FESSSGLVWT

NPNANPNANP NASYSITTPS QFVFLSSAWA DPIELINLCT NALGNQFQTQ

QARTVVQRQF SEVWKPSPQV TVRFPDSDFK VYRYNAVLDP LVTALLGAFD TRN.

TMV-NPNAx4-L:

SEQ ID NO: 6

MHHHHHHTRR VDDATVAIRS AINNLIVELI RGTGSYNRSS FESSSGLVWT

NPNANPNANP NANPNASYSI TTPSQFVFLS SAWADPIELI NLCTNALGNQ

FQTQQARTVV QRQFSEVWKP SPQVTVRFPD SDFKVYRYNA VLDPLVTALL GAFDTRN.

TMV-NPNAx5-L:

SEQ ID NO: 7

MHHHHHHTRR VDDATVAIRS AINNLIVELI RGTGSYNRSS FESSSGLVWT

NPNANPNANP NANPNANPNA SYSITTPSQF VFLSSAWADP IELINLCTNA

LGNQFQTQQA RTVVQRQFSE VWKPSPQVTV RFPDSDFKVY RYNAVLDPLV

TALLGAFDTR N.

TMV-NPNAx5-NT:

SEQ ID NO: 8

MNPNANPNAN PNANPNANPN ASYSITTPSQ FVFLSSAWAD PIELINLCTN

ALGNQFQTQQ ARTVVQRQFS EVWKPSPQVT VRFPDSDFKV YRYNAVLDPL

VTALLGAFDT RNHHHHHHHH TRRVDDATVA IRSAINNLIV ELIRGTGSYN

RSSFESSSGL VWTSG.

-continued

TMV-NPNAx5-CT:

SEQ ID NO: 9

MSYSITTPSQ FVFLSSAWAD PIELINLCTN ALGNQFQTQQ ARTVVQRQFS

EVWKPSPQVT VRFPDSDFKV YRYNAVLDPL VTALLGAFDT RNHHHHHHHH

TRRVDDATVA IRSAINNLIV ELIRGTGSYN RSSFESSSGL VWTSGNPNAN

PNANPNANPN ANPNA.

TMV-NPNAx7-L:

SEQ ID NO: 10

MHHHHHHTRR VDDATVAIRS AINNLIVELI RGTGSYNRSS FESSSGLVWT

NPNANPNANP NANPNANPNA NPNANPNASY SITTPSQFVF LSSAWADPIE

LINLCTNALG NQFQTQQART VVQRQFSEVW KPSPQVTVRF PDSDFKVYRY

NAVLDPLVTA LLGAFDTRN.

TMV-NPNAx10-L

SEQ ID NO: 11

MHHHHHHTRR VDDATVAIRS AINNLIVELI RGTGSYNRSS FESSSGLVWT

NPNANPNANP NANPNANPNA NPNANPNANP NANPNANPNA SYSITTPSQF

VFLSSAWADP IELINLCTNA LGNQFQTQQA RTVVQRQFSE VWKPSPQVTV

RFPDSDFKVY RYNAVLDPLV TALLGAFDTR N.

TMV-NPNAx20-L:

SEQ ID NO: 12

MHHHHHHTRR VDDATVAIRS AINNLIVELI RGTGSYNRSS FESSSGLVWT

NPNANPNANP NANPNANPNA NPNANPNANP NANPNANPNA NPNANPNANP

NANPNANPNA NPNANPNANP NANPNANPNA SYSITTPSQF VFLSSAWADP

IELINLCTNA LGNQFQTQQA RTVVQRQFSE VWKPSPQVTV RFPDSDFKVY

RYNAVLDPLV TALLGAFDTR N.

SEQ ID NO: 13

(None).

ZMV-NPNAx5-L

SEQ ID NO: 14

MKRNDDASTA AHNDIPQILS ALNEGAGVFD RASFESAFGL TWTNPNANPN

ANPNANPNAN PNASYSTSGI RSLPAFSKSF FPYLELYNLL ITNQGAALQT

QNGKDILRES LVGLLSSVAS PTSQFPSGVF YVWSRESRIA ALIDSLFGAL

DSRN.

ZMV-NPNAx7-L:

SEQ ID NO: 15

MKRNDDASTA AHNDIPQILS ALNEGAGVFD RASFESAFGL TWTNPNANPN

ANPNANPNAN PNANPNANPN ASYSTSGIRS LPAFSKSFFP YLELYNLLIT

NQGAALQTQN GKDILRESLV GLLSSVASPT SQFPSGVFYV WSRESRIAAL

IDSLFGALDS RN.

ZMV P. falciparum AMA1 domain III loop:

SEQ ID NO: 16

MKRNDDASTA AHNDIPQILS ALNEGAGVFD RASFESAFGL TWTMKEIERE

SKRIKLNDND DEGNKKIIAS YSTSGIRSLP AFSKSFFPYL ELYNLLITNQ

GAALQTQNGK DILRESLVGL LSSVASPTSQ FPSGVFYVWSR ESRIAALIDS

LFGALDSRN.

ZMV P. falciparum AMA1 domain II loop:

SEQ ID NO: 17

MKRNDDASTA AHNDIPQILS ALNEGAGVFD RASFESAFGL TWSDQPKQYE

QHLTDYEKIK EGFKNKNASM IKSAFLPTGA FKADRYGSYS TSGIRSLPAF

-continued

SKSFFPYLEL YNLLITNQGA ALQTQNGKD ILRESLVGLLS SVASPTSQFP

SGVFYVWSRE SRIAALIDSL FGALDSRN.

ZMV P. falciparum AMA1 Ie loop:

SEQ ID NO: 18

MKRNDDASTA AHNDIPQILS ALNEGAGVFD RASFESAFGL TWTGIPDNDK

NSNSKGSYST SGIRSLPAFS KSFFPYLELY NLLITNQGAA LQTQNGKDIL

RESLVGLLSS VASPTSQFPS GVFYVWSRES RIAALIDSLF GALDSRN.

TMV-NPNAx5-Acidic-out:

SEQ ID NO: 19

MHHHHHHTRR VDDATVAIRS AINNLIVELI RGTGSYNRSS FESSSGLVWT

SDNPNANPNA NPNANPNANP NAEGSYSITT PSQFVFLSSA WADPIELINL

CTNALGNQFQ TQQARTVVQR QFSEVWKPSP QVTVRFPDSD FKVYRYNAVL

DPLVTALLGA FDTRN.

TMV-NPNAx5-Acidic-in:

SEQ ID NO: 20

MHHHHHHDAT RRVDDATVAI RSAINNLIVE LIRGTGSYNR SSFESSSGLV

WTNPNANPNA NPNANPNANP NASYSITTPS QFVFLSSAWA DPIELINLCT

NALGNQFQTQ QARTVVQRQF SEVWKPSPQV TVRFPDSDFK VYRYNAVLDP

LVTALLGAFD TRNRIIE.

TMV-Acidic-out:

SEQ ID NO: 21

MHHHHHHTRR VDDATVAIRS AINNLIVELI RGTGSYNRSS FESSSGLVWT

SD . . . epitope insert . . . EGS YSITTPSQFV FLSSAWADPI ELINLCTNAL

GNQFQTQQAR TVVQRQFSEV WKPSPQVTVR FPDSDFKVYR YNAVLDPLVT

ALLGAFDTRN.

TMV-Acidic-in:

SEQ ID NO: 22

MHHHHHHDAT RRVDDATVAI RSAINNLIVE LIRGTGSYNR SSFESSSGLV

WT . . . epitope insert . . . SYS ITTPSQFVFL SSAWADPIEL INLCTNALGN

QFQTQQARTV VQRQFSEVWK PSPQVTVRFP DSDFKVYRYN AVLDPLVTAL

LGAFDTRNRI IE.

ZMV-(VK210)x5:

SEQ ID NO 23

MKRNDDASTA AHNDIPQILS ALNEGAGVFD RASFESAFGL TWTGDRADGQ

PAGDRAAGQP AGDRADGQPA GDRAAGQPAG DRADGQPASY STSGIRSLPA

FSKSFFPYLE LYNLLITNQG AALQTQNGKD ILRESLVGLL SSVASPTSQF

PSGVFYVWSR ESRIAALIDS LFGALDSRN.

ZMV-(VK247)x3:

SEQ ID NO 24

MKRNDDASTA AHNDIPQILS ALNEGAGVFD RASFESAFGL TWTGNQPGAN

GAGNQPGANG AGNQPGANGS YSTSGIRSLP AFSKSFFPYL ELYNLLITNQ

GAALQTQNGK DILRESLVGL LSSVASPTSQ FPSGVFYVWS RESRIAALID

SLFGALDSRN.

-continued

```
TMV-(VK247)x5:
                                                          SEQ ID NO 25
MHHHHHHTRR VDDATVAIRS AINNLIVELI RGTGSYNRSS FESSSGLVWT

GNQPGANGAG DQPGANGAGN QPGANGAGNQ PGANGAGNQP GANGAGNQPG

ANGSYSITTP SQFVFLSSAW ADPIELINLC TNALGNQFQT QQARTVVQRQ

FSEVWKPSPQ VTVRFPDSDF KVYRYNAVLD PLVTALLGAF DTRN.
```

REFERENCES

1. Davies D R, Sheriff S, Padlan E A: Antibody-antigen complexes. J Biol Chem 1988, 263:10541-10544.2.
2. MacRaild C A, Zachrdla M, Andrew D, Krishnarjuna B, Novacek J, Zidek L, Sklenar V, Richards J S, Beeson J G, Anders R F, Norton R S: Conformational dynamics and antigenicity in the disordered malaria antigen merozoite surface protein 2. PLoS One 2015, 10:e0119899.
3. Neafsey D E, Juraska M, Bedford T, Benkeser D, Valim C, et al. (2015) Genetic Diversity and Protective Efficacy of the RTS,S/AS01 Malaria Vaccine. N Engl J Med 373: 2025-2037.3.
4. Kaba S A, McCoy M E, Doll T A, Brando C, Guo Q, et al. (2012) Protective antibody and CD8+ T-cell responses to the *Plasmodium falciparum* circumsporozoite protein induced by a nanoparticle vaccine. PLoS One 7: e48304.4.
5. White M T, Bejon P, Olotu A, Griffin J T, Riley E M, et al. (2013) The relationship between RTS,S vaccine-induced antibodies, CD4(+) T cell responses and protection against *Plasmodium falciparum* infection. PLoS One 8: e61395.
6. Espinosa D A, Gutierrez G M, Rojas-Lopez M, Noe A R, Shi L, Tse S W, Sinnis P, Zavala F. Proteolytic cleavage of the *Plasmodium falciparum* circumsporozoite protein is a target of protective antibodies. The Journal of infectious diseases. 2015 Mar. 11; 212(7):1111-9.
7. Zhao L, Seth A, Wibowo N, Zhao C X, Mitter N, Yu C, Middelberg A P. Nanoparticle vaccines. Vaccine. 2014 Jan. 9; 32(3):327-37.
8. Dedeo M T, Duderstadt K E, Berger J M, Francis M B: Nanoscale protein assemblies from a circular permutant of the tobacco mosaic virus. Nano Lett 2010, 10:181-186.
9. Porter M D, Nicki J, Pool C D, DeBot M, Illam R M, Brando C, Bozick B, De La Vega P, Angra D, Spaccapelo R, et al: Transgenic parasites stably expressing full-length *Plasmodium falciparum* circumsporozoite protein as a model for vaccine down-selection in mice using sterile protection as an endpoint. Clin Vaccine Immunol 2013, 20:803-810.
10. Tan J, Sack B K, Oyen D, Zenklusen I, Piccoli L, Barbieri S, Foglierini M, Fregni C S, Marcandalli J, Jongo S, Abdulla S. A public antibody lineage that potently inhibits malaria infection through dual binding to the circumsporozoite protein. Nature medicine. 2018 April; 24(4):401.
11. Kisalu N K, Idris A H, Weidle C, Flores-Garcia Y, Flynn B J, Sack B K, Murphy S, Schott A, Freire E, Francica J R, Miller A B. A human monoclonal antibody prevents malaria infection by targeting a new site of vulnerability on the parasite. Nature medicine. 2018 April; 24(4):408.
12. Oyen D, Torres J L, Wille-Reece U, Ockenhouse C F, Emerling D, Glanville J, Volkmuth W, Flores-Garcia Y, Zavala F, Ward A B, King C R. Structural basis for antibody recognition of the NANP repeats in *Plasmodium falciparum* circumsporozoite protein. Proceedings of the National Academy of Sciences. 2017 Nov. 14:201715812.
13. Triller G, Scally S W, Costa G, Pissarev M, Kreschel C, Bosch A, Marois E, Sack B K, Murugan R, Salman A M, Janse C J. Natural parasite exposure induces protective human anti-malarial antibodies. Immunity. 2017 Dec. 19; 47(6):1197-209.
14. Collins K A, Snaith R, Cottingham M G, Gilbert S C, Hill AVS: Enhancing protective immunity to malaria with a highly immunogenic virus-like particle vaccine. Sci Rep 2017, 7:46621.
15. Kim D E, Chivian D, Baker D: Protein structure prediction and analysis using the Robetta server. Nucleic Acids Res 2004, 32:W526-531.
16. Schwenk R, DeBot M, Porter M, Nikki J, Rein L, Spaccapelo R, Crisanti A, Wightman P D, Ockenhouse C F, Dutta S: IgG2 antibodies against a clinical grade *Plasmodium falciparum* CSP vaccine antigen associate with protection against transgenic sporozoite challenge in mice. PLoS One 2014, 9:e111020.
17. Wang H, Planchart A, Stubbs G. Caspar carboxylates: the structural basis of tobamovirus disassembly. Biophysical journal. 1998 Jan. 1; 74(1):633-8.
18. Lu B, Stubbs G, Culver J N. Carboxylate interactions involved in the disassembly of tobacco mosaic tobamovirus. Virology. 1996 Nov. 1; 225(1):11-20.
19. Bendahmane M, Koo M, Karrer E, Beachy R N. Display of epitopes on the surface of tobacco mosaic virus: impact of charge and isoelectric point of the epitope on virus-host interactionsl. Journal of molecular biology. 1999 Jul. 2; 290(1):9-20.
20. Zhang Y B, Howitt J, McCorkle S, Lawrence P, Springer K, Freimuth P. Protein aggregation during overexpression limited by peptide extensions with large net negative charge. Protein expression and purification. 2004 Aug. 1; 36(2):207-16.
21. Qari S H, Goldman I F, Povoa M M, di Santi S, Alpers M P, Lal A A. Polymorphism in the circumsporozoite protein of the human malaria parasite *Plasmodium vivax*. Molecular and Biochemical Parasitology. 1992 Oct. 1; 55(1-2):105-13.
22. RTS,S CTP, Agnandji S T, Lell B, Fernandes J F, Abossolo B P, Methogo B G, Kabwende A L, Adegnika A A, Mordmuller B, Issifou S, et al: A phase 3 trial of RTS,S/AS01 malaria vaccine in African infants. N Engl J Med 2012, 367:2284-2295.

We claim:

1. A recombinant protein comprising a modified Tobamovirus capsid protein and an immunogenic epitope of an antigen of interest, wherein the modified Tobamovirus capsid protein comprises an amino acid sequence selected from the group consisting of: amino acid residues 8-148 of SEQ ID NO: 2, amino acid residues 8-141 of SEQ ID NO: 4, amino acid residues 8-146 of SEQ ID NO: 21, and amino acid residues 8-148 of SEQ ID NO: 22, and wherein:

when the modified Tobamovirus capsid protein comprises SEQ ID NO: 2, the immunogenic epitope replaces amino acid residues 51-57 of SEQ ID NO: 2;

when the modified Tobamovirus capsid protein comprises SEQ ID NO: 4, the immunogenic epitope replaces amino acid residues 50-51 of SEQ ID NO: 4;

when the modified Tobamovirus capsid protein comprises SEQ ID NO: 21, the immunogenic epitope is inserted at amino acid residue 53 of SEQ ID NO: 21; and when the modified Tobamovirus capsid protein comprises SEQ ID NO: 22, the immunogenic epitope is inserted at amino acid residue 53 of SEQ ID NO: 22.

2. The recombinant protein of claim 1, wherein the immunogenic epitope is derived from an antigen that induces an immune response against cancer cells; an antigen that induces an immune response against an infectious disease; or an antigen that induces an immune response against allergens.

3. The recombinant protein of claim 1, wherein the immunogenic epitope is derived from a virus or bacterium.

4. The recombinant protein of claim 1, wherein the immunogenic epitope is derived from a *Plasmodium* species.

5. The recombinant protein of claim 1, selected from the group consisting of: SEQ ID NO: 5; SEQ ID NO: 6; SEQ ID NO: 7; SEQ ID NO: 10; SEQ ID NO: 11; SEQ ID NO: 12; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 23; SEQ ID NO: 24; and SEQ ID NO: 25.

6. A composition comprising the recombinant protein of claim 1, selected from the group consisting of: SEQ ID NO: 5; SEQ ID NO: 6, SEQ ID NO: 7; SEQ ID NO: 10; SEQ ID NO: 11; SEQ ID NO: 12; SEQ ID NO: 14; SEQ ID NO: 15; SEQ ID NO: 16; SEQ ID NO: 17; SEQ ID NO: 18, SEQ ID NO: 19, SEQ ID NO: 20; SEQ ID NO: 23; SEQ ID NO: 24; and SEQ ID NO: 25.

7. A vaccine comprising the recombinant protein of claim 1.

8. The vaccine of claim 7 further comprising an adjuvant.

9. The vaccine of claim 7, wherein the vaccine comprises a plurality of the recombinant proteins that assemble in an array that forms an interior region and an external region, wherein the immunogenic epitope is displayed on the external region of the array.

10. The vaccine of claim 9, wherein the immunogenic epitope comprises the amino acid sequence (NPNA)n of circumsporozoite protein (CSP) from *P. falciparum*, wherein n is an integer selected from 1 to 20.

11. The vaccine of claim 10, wherein n is an integer selected from 1-10.

12. The vaccine of claim 10, wherein n is 5.

13. A method for purifying the recombinant protein of claim 1, the method comprising: expressing the recombinant protein in a host cell; and isolating the recombinant protein.

14. A method of enhancing immunogenicity of an amino acid antigen, wherein the method comprises:

expressing a recombinant protein that comprises the amino acid antigen and a modified Tobamovirus capsid protein;

isolating the recombinant protein under conditions that allow the recombinant protein to assemble in an array of monomers that forms an interior region and an external region, wherein the amino acid antigen is displayed on the external region of the array of monomers, and wherein the modified Tobamovirus capsid protein comprises an amino acid sequence selected from the group consisting of: amino acid residues 8-148 of SEQ ID NO: 2, amino acid residues 8-141 of SEQ ID NO: 4, amino acid residues 8-146 of SEQ ID NO: 21, and amino acid residues 8-148 of SEQ ID NO: 22, and wherein:

when the modified Tobamovirus capsid protein comprises SEQ ID NO: 2, the amino acid antigen replaces amino acid residues 51-57 of SEQ ID NO: 2;

when the modified Tobamovirus capsid protein comprises SEQ ID NO: 4, the amino acid antigen replaces amino acid residues 50-51 of SEQ ID NO: 4;

when the modified Tobamovirus capsid protein comprises SEQ ID NO: 21, the amino acid antigen is inserted at amino acid residue 53 of SEQ ID NO: 21; and when the modified Tobamovirus capsid protein comprises SEQ ID NO: 22, the amino acid antigen is inserted at amino acid residue 53 of SEQ ID NO: 22.

15. The method of claim 14, wherein the modified Tobamovirus capsid protein is selected from the group consisting of a modified Tobacco mosaic virus (TMV) capsid protein and a modified zucchini green mottled mosaic virus (ZMV) capsid protein.

16. A method of inducing an immune response in a mammal comprising:

administering to the mammal an effective amount of the composition of claim 6, to induce an immune response in the mammal.

17. The recombinant protein of claim 1, further comprising a N-terminal histidine tag.

18. The recombinant protein of claim 4, wherein the immunogenic epitope comprises the amino acid sequence (NPNA)n of circumsporozoite protein (CSP) from *P. falciparum*, wherein n is an integer selected from 1 to 20.

19. The vaccine of claim 10, wherein the vaccine comprises an amino acid sequence selected from the group consisting of: SEQ ID NO: 5, SEQ ID NO: 6, SEQ ID NO:

7, SEQ ID NO: 10, SEQ ID NO: 11, SEQ ID NO: 12, SEQ ID NO: 19, and SEQ ID NO: 20.

20. The method of claim 13, wherein the host cell is *E. coli*.

* * * * *

SEQUENCE LISTING

<160> NUMBER OF SEQ ID NOS: 25

<210> SEQ ID NO 1
<211> LENGTH: 159
<212> TYPE: PRT
<213> ORGANISM: Tobacco mosaic virus

<400> SEQUENCE: 1

Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125

Leu Ile Val Glu Leu Thr Arg Gly Thr Gly Ser Tyr Asn Arg Ser Ser
    130                 135                 140

Phe Glu Ser Ser Ser Gly Leu Val Trp Thr Ser Ser Pro Ala Thr
145                 150                 155

<210> SEQ ID NO 2
<211> LENGTH: 148
<212> TYPE: PRT
<213> ORGANISM: Artificial Sequence
<220> FEATURE:
<223> OTHER INFORMATION: Synthetic

<400> SEQUENCE: 2

Met His His His His His His Thr Arg Arg Val Asp Asp Ala Thr Val
1               5                   10                  15

Ala Ile Arg Cys Ala Ile Asn Asn Leu Ile Val Glu Leu Ile Arg Gly
            20                  25                  30

Thr Gly Ser Tyr Asn Arg Ser Ser Phe Glu Ser Ser Ser Gly Leu Val
        35                  40                  45

Trp Thr Ser Gly Pro Ala Gly Glu Gly Ser Tyr Ser Ile Thr Thr Pro
    50                  55                  60

Ser Gln Phe Val Phe Leu Ser Ser Ala Trp Ala Asp Pro Ile Glu Leu
65                  70                  75                  80

Ile Asn Leu Cys Thr Asn Ala Leu Gly Asn Gln Phe Gln Thr Gln Gln
                85                  90                  95

Ala Arg Thr Val Val Gln Arg Gln Phe Ser Glu Val Trp Lys Pro Ser
            100                 105                 110

Pro Gln Val Thr Val Arg Phe Pro Asp Ser Asp Phe Lys Val Tyr Arg
        115                 120                 125

Tyr Asn Ala Val Leu Asp Pro Leu Val Thr Ala Leu Leu Gly Ala Phe
    130                 135                 140

Asp Thr Arg Asn
145

<210> SEQ ID NO 3
<211> LENGTH: 161
<212> TYPE: PRT
<213> ORGANISM: Zucchini mosaic virus

<400> SEQUENCE: 3

```
Met Pro Tyr Ser Thr Ser Gly Ile Arg Ser Leu Pro Ala Phe Ser Lys
1               5                   10                  15

Ser Phe Phe Pro Tyr Leu Glu Leu Tyr Asn Leu Leu Ile Thr Asn Gln
            20                  25                  30

Gly Ala Ala Leu Gln Thr Gln Asn Gly Lys Asp Ile Leu Arg Glu Ser
        35                  40                  45

Leu Val Gly Leu Leu Ser Ser Val Ala Ser Pro Thr Ser Gln Phe Pro
    50                  55                  60

Ser Gly Val Phe Tyr Val Trp Ser Arg Glu Ser Arg Ile Ala Ala Leu
65                  70                  75                  80

Ile Asp Ser Leu Phe Gly Ala Leu Asp Ser Arg Asn Arg Ala Ile Glu
                85                  90                  95

Val Glu Asn Pro Ser Asn Pro Ser Thr Gly Glu Ala Leu Asn Ala Val
            100                 105                 110

Lys Arg Asn Asp Asp Ala Ser Thr Ala Ala His Asn Asp Ile Pro Gln
        115                 120                 125

Ile Leu Ser Ala Leu Asn Glu Gly Ala Gly Val Phe Asp Arg Ala Ser
    130                 135                 140

Phe Glu Ser Ala Phe Gly Leu Val Trp Thr Ala Gly Ser Ser Thr Ser
145                 150                 155                 160

Ser
```

<210> SEQ ID NO 4
<211> LENGTH: 141
<212> TYPE: PRT
<213> ORGANISM: Artificial Sequence
<220> FEATURE:
<223> OTHER INFORMATION: Synthetic

<400> SEQUENCE: 4

```
Met His His His His His His Lys Arg Asn Asp Asp Ala Ser Thr Ala
1               5                   10                  15

Ala His Asn Asp Ile Pro Gln Ile Leu Ser Ala Leu Asn Glu Gly Ala
            20                  25                  30

Gly Val Phe Asp Arg Ala Ser Phe Glu Ser Ala Phe Gly Leu Thr Trp
        35                  40                  45

Thr Gly Ser Ser Tyr Ser Thr Ser Gly Ile Arg Ser Leu Pro Ala Phe
    50                  55                  60

Ser Lys Ser Phe Phe Pro Tyr Leu Glu Leu Tyr Asn Leu Leu Ile Thr
65                  70                  75                  80

Asn Gln Gly Ala Ala Leu Gln Thr Gln Asn Gly Lys Asp Ile Leu Arg
                85                  90                  95

Glu Ser Leu Val Gly Leu Leu Ser Ser Val Ala Ser Pro Thr Ser Gln
            100                 105                 110

Phe Pro Ser Gly Val Phe Tyr Val Trp Ser Arg Glu Ser Arg Ile Ala
        115                 120                 125

Ala Leu Ile Asp Ser Leu Phe Gly Ala Leu Asp Gln Glu
    130                 135                 140
```

-continued

<210> SEQ ID NO 5
<211> LENGTH: 153
<212> TYPE: PRT
<213> ORGANISM: Artificial Sequence
<220> FEATURE:
<223> OTHER INFORMATION: Synthetic

<400> SEQUENCE: 5

```
Met His His His His His His Thr Arg Arg Val Asp Asp Ala Thr Val
1               5                   10                  15

Ala Ile Arg Ser Ala Ile Asn Asn Leu Ile Val Glu Leu Ile Arg Gly
            20                  25                  30

Thr Gly Ser Tyr Asn Arg Ser Ser Phe Glu Ser Ser Ser Gly Leu Val
        35                  40                  45

Trp Thr Asn Pro Asn Ala Asn Pro Asn Ala Asn Pro Asn Ala Ser Tyr
    50                  55                  60

Ser Ile Thr Thr Pro Ser Gln Phe Val Phe Leu Ser Ser Ala Trp Ala
65                  70                  75                  80

Asp Pro Ile Glu Leu Ile Asn Leu Cys Thr Asn Ala Leu Gly Asn Gln
                85                  90                  95

Phe Gln Thr Gln Gln Ala Arg Thr Val Val Gln Arg Gln Phe Ser Glu
            100                 105                 110

Val Trp Lys Pro Ser Pro Gln Val Thr Val Arg Phe Pro Asp Ser Asp
        115                 120                 125

Phe Lys Val Tyr Arg Tyr Asn Ala Val Leu Asp Pro Leu Val Thr Ala
    130                 135                 140

Leu Leu Gly Ala Phe Asp Thr Arg Asn
145                 150
```

<210> SEQ ID NO 6
<211> LENGTH: 157
<212> TYPE: PRT
<213> ORGANISM: Artificial Sequence
<220> FEATURE:
<223> OTHER INFORMATION: Synthetic

<400> SEQUENCE: 6

```
Met His His His His His His Thr Arg Arg Val Asp Asp Ala Thr Val
1               5                   10                  15

Ala Ile Arg Ser Ala Ile Asn Asn Leu Ile Val Glu Leu Ile Arg Gly
            20                  25                  30

Thr Gly Ser Tyr Asn Arg Ser Ser Phe Glu Ser Ser Ser Gly Leu Val
        35                  40                  45

Trp Thr Asn Pro Asn Ala Asn Pro Asn Ala Asn Pro Asn Ala Asn Pro
    50                  55                  60

Asn Ala Ser Tyr Ser Ile Thr Thr Pro Ser Gln Phe Val Phe Leu Ser
65                  70                  75                  80

Ser Ala Trp Ala Asp Pro Ile Glu Leu Ile Asn Leu Cys Thr Asn Ala
                85                  90                  95

Leu Gly Asn Gln Phe Gln Thr Gln Gln Ala Arg Thr Val Val Gln Arg
            100                 105                 110

Gln Phe Ser Glu Val Trp Lys Pro Ser Pro Gln Val Thr Val Arg Phe
        115                 120                 125

Pro Asp Ser Asp Phe Lys Val Tyr Arg Tyr Asn Ala Val Leu Asp Pro
    130                 135                 140

Leu Val Thr Ala Leu Leu Gly Ala Phe Asp Thr Arg Asn
145                 150                 155
```

-continued

<210> SEQ ID NO 7
<211> LENGTH: 161
<212> TYPE: PRT
<213> ORGANISM: Artificial Sequence
<220> FEATURE:
<223> OTHER INFORMATION: Sythetic

<400> SEQUENCE: 7

```
Met His His His His His His Thr Arg Arg Val Asp Asp Ala Thr Val
1               5                   10                  15

Ala Ile Arg Ser Ala Ile Asn Asn Leu Ile Val Glu Leu Ile Arg Gly
            20                  25                  30

Thr Gly Ser Tyr Asn Arg Ser Ser Phe Glu Ser Ser Ser Gly Leu Val
        35                  40                  45

Trp Thr Asn Pro Asn Ala Asn Pro Asn Ala Asn Pro Asn Ala Asn Pro
    50                  55                  60

Asn Ala Asn Pro Asn Ala Ser Tyr Ser Ile Thr Thr Pro Ser Gln Phe
65                  70                  75                  80

Val Phe Leu Ser Ser Ala Trp Ala Asp Pro Ile Glu Leu Ile Asn Leu
                85                  90                  95

Cys Thr Asn Ala Leu Gly Asn Gln Phe Gln Thr Gln Gln Ala Arg Thr
            100                 105                 110

Val Val Gln Arg Gln Phe Ser Glu Val Trp Lys Pro Ser Pro Gln Val
        115                 120                 125

Thr Val Arg Phe Pro Asp Ser Asp Phe Lys Val Tyr Arg Tyr Asn Ala
    130                 135                 140

Val Leu Asp Pro Leu Val Thr Ala Leu Leu Gly Ala Phe Asp Thr Arg
145                 150                 155                 160

Asn
```

<210> SEQ ID NO 8
<211> LENGTH: 165
<212> TYPE: PRT
<213> ORGANISM: Artificial Sequence
<220> FEATURE:
<223> OTHER INFORMATION: Synthetic

<400> SEQUENCE: 8

```
Met Asn Pro Asn Ala Asn Pro Asn Ala Asn Pro Asn Ala Asn Pro Asn
1               5                   10                  15

Ala Asn Pro Asn Ala Ser Tyr Ser Ile Thr Thr Pro Ser Gln Phe Val
            20                  25                  30

Phe Leu Ser Ser Ala Trp Ala Asp Pro Ile Glu Leu Ile Asn Leu Cys
        35                  40                  45

Thr Asn Ala Leu Gly Asn Gln Phe Gln Thr Gln Gln Ala Arg Thr Val
    50                  55                  60

Val Gln Arg Gln Phe Ser Glu Val Trp Lys Pro Ser Pro Gln Val Thr
65                  70                  75                  80

Val Arg Phe Pro Asp Ser Asp Phe Lys Val Tyr Arg Tyr Asn Ala Val
                85                  90                  95

Leu Asp Pro Leu Val Thr Ala Leu Leu Gly Ala Phe Asp Thr Arg Asn
            100                 105                 110

His His His His His His His His Thr Arg Arg Val Asp Asp Ala Thr
        115                 120                 125

Val Ala Ile Arg Ser Ala Ile Asn Asn Leu Ile Val Glu Leu Ile Arg
    130                 135                 140
```

-continued

```
Gly Thr Gly Ser Tyr Asn Arg Ser Ser Phe Glu Ser Ser Ser Gly Leu
145                 150                 155                 160

Val Trp Thr Ser Gly
                165
```

<210> SEQ ID NO 9
<211> LENGTH: 165
<212> TYPE: PRT
<213> ORGANISM: Artificial Sequence
<220> FEATURE:
<223> OTHER INFORMATION: Synthetic

<400> SEQUENCE: 9

```
Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn His His His His
                85                  90                  95

His His His His Thr Arg Arg Val Asp Asp Ala Thr Val Ala Ile Arg
            100                 105                 110

Ser Ala Ile Asn Asn Leu Ile Val Glu Leu Ile Arg Gly Thr Gly Ser
        115                 120                 125

Tyr Asn Arg Ser Ser Phe Glu Ser Ser Ser Gly Leu Val Trp Thr Ser
    130                 135                 140

Gly Asn Pro Asn Ala Asn Pro Asn Ala Asn Pro Asn Ala Asn Pro Asn
145                 150                 155                 160

Ala Asn Pro Asn Ala
                165
```

<210> SEQ ID NO 10
<211> LENGTH: 169
<212> TYPE: PRT
<213> ORGANISM: Artificial Sequence
<220> FEATURE:
<223> OTHER INFORMATION: Synthetic

<400> SEQUENCE: 10

```
Met His His His His His His Thr Arg Arg Val Asp Asp Ala Thr Val
1               5                   10                  15

Ala Ile Arg Ser Ala Ile Asn Asn Leu Ile Val Glu Leu Ile Arg Gly
            20                  25                  30

Thr Gly Ser Tyr Asn Arg Ser Ser Phe Glu Ser Ser Ser Gly Leu Val
        35                  40                  45

Trp Thr Asn Pro Asn Ala Asn Pro Asn Ala Asn Pro Asn Ala Asn Pro
    50                  55                  60

Asn Ala Asn Pro Asn Ala Asn Pro Asn Ala Asn Pro Asn Ala Ser Tyr
65                  70                  75                  80

Ser Ile Thr Thr Pro Ser Gln Phe Val Phe Leu Ser Ser Ala Trp Ala
                85                  90                  95

Asp Pro Ile Glu Leu Ile Asn Leu Cys Thr Asn Ala Leu Gly Asn Gln
            100                 105                 110
```

Phe Gln Thr Gln Gln Ala Arg Thr Val Val Gln Arg Gln Phe Ser Glu
115 120 125

Val Trp Lys Pro Ser Pro Gln Val Thr Val Arg Phe Pro Asp Ser Asp
130 135 140

Phe Lys Val Tyr Arg Tyr Asn Ala Val Leu Asp Pro Leu Val Thr Ala
145 150 155 160

Leu Leu Gly Ala Phe Asp Thr Arg Asn
165

<210> SEQ ID NO 11
<211> LENGTH: 181
<212> TYPE: PRT
<213> ORGANISM: Artificial Sequence
<220> FEATURE:
<223> OTHER INFORMATION: Synthetic

<400> SEQUENCE: 11

Met His His His His His His Thr Arg Arg Val Asp Asp Ala Thr Val
1 5 10 15

Ala Ile Arg Ser Ala Ile Asn Asn Leu Ile Val Glu Leu Ile Arg Gly
20 25 30

Thr Gly Ser Tyr Asn Arg Ser Ser Phe Glu Ser Ser Ser Gly Leu Val
35 40 45

Trp Thr Asn Pro Asn Ala Asn Pro Asn Ala Asn Pro Asn Ala Asn Pro
50 55 60

Asn Ala Asn Pro Asn Ala Asn Pro Asn Ala Asn Pro Asn Ala Asn Pro
65 70 75 80

Asn Ala Asn Pro Asn Ala Asn Pro Asn Ala Ser Tyr Ser Ile Thr Thr
85 90 95

Pro Ser Gln Phe Val Phe Leu Ser Ser Ala Trp Ala Asp Pro Ile Glu
100 105 110

Leu Ile Asn Leu Cys Thr Asn Ala Leu Gly Asn Gln Phe Gln Thr Gln
115 120 125

Gln Ala Arg Thr Val Val Gln Arg Gln Phe Ser Glu Val Trp Lys Pro
130 135 140

Ser Pro Gln Val Thr Val Arg Phe Pro Asp Ser Asp Phe Lys Val Tyr
145 150 155 160

Arg Tyr Asn Ala Val Leu Asp Pro Leu Val Thr Ala Leu Leu Gly Ala
165 170 175

Phe Asp Thr Arg Asn
180

<210> SEQ ID NO 12
<211> LENGTH: 221
<212> TYPE: PRT
<213> ORGANISM: Artificial Sequence
<220> FEATURE:
<223> OTHER INFORMATION: Synthetic

<400> SEQUENCE: 12

Met His His His His His His Thr Arg Arg Val Asp Asp Ala Thr Val
1 5 10 15

Ala Ile Arg Ser Ala Ile Asn Asn Leu Ile Val Glu Leu Ile Arg Gly
20 25 30

Thr Gly Ser Tyr Asn Arg Ser Ser Phe Glu Ser Ser Ser Gly Leu Val
35 40 45

Trp Thr Asn Pro Asn Ala Asn Pro Asn Ala Asn Pro Asn Ala Asn Pro

```
    50                  55                  60

Asn Ala Asn Pro Asn Ala Asn Pro Asn Ala Asn Pro Asn Ala Asn Pro
65                  70                  75                  80

Asn Ala Asn Pro Asn Ala Asn Pro Asn Ala Asn Pro Asn Ala Asn Pro
                85                  90                  95

Asn Ala Asn Pro Asn Ala Asn Pro Asn Ala Asn Pro Asn Ala Asn Pro
            100                 105                 110

Asn Ala Asn Pro Asn Ala Asn Pro Asn Ala Asn Pro Asn Ala Asn Pro
        115                 120                 125

Asn Ala Ser Tyr Ser Ile Thr Thr Pro Ser Gln Phe Val Phe Leu Ser
    130                 135                 140

Ser Ala Trp Ala Asp Pro Ile Glu Leu Ile Asn Leu Cys Thr Asn Ala
145                 150                 155                 160

Leu Gly Asn Gln Phe Gln Thr Gln Gln Ala Arg Thr Val Val Gln Arg
                165                 170                 175

Gln Phe Ser Glu Val Trp Lys Pro Ser Pro Gln Val Thr Val Arg Phe
            180                 185                 190

Pro Asp Ser Asp Phe Lys Val Tyr Arg Tyr Asn Ala Val Leu Asp Pro
        195                 200                 205

Leu Val Thr Ala Leu Leu Gly Ala Phe Asp Thr Arg Asn
    210                 215                 220


<210> SEQ ID NO 13

<400> SEQUENCE: 13

000


<210> SEQ ID NO 14
<211> LENGTH: 154
<212> TYPE: PRT
<213> ORGANISM: Artificial Sequence
<220> FEATURE:
<223> OTHER INFORMATION: Synthetic

<400> SEQUENCE: 14

Met Lys Arg Asn Asp Asp Ala Ser Thr Ala Ala His Asn Asp Ile Pro
1               5                   10                  15

Gln Ile Leu Ser Ala Leu Asn Glu Gly Ala Gly Val Phe Asp Arg Ala
            20                  25                  30

Ser Phe Glu Ser Ala Phe Gly Leu Thr Trp Thr Asn Pro Asn Ala Asn
        35                  40                  45

Pro Asn Ala Asn Pro Asn Ala Asn Pro Asn Ala Asn Pro Asn Ala Ser
    50                  55                  60

Tyr Ser Thr Ser Gly Ile Arg Ser Leu Pro Ala Phe Ser Lys Ser Phe
65                  70                  75                  80

Phe Pro Tyr Leu Glu Leu Tyr Asn Leu Leu Ile Thr Asn Gln Gly Ala
                85                  90                  95

Ala Leu Gln Thr Gln Asn Gly Lys Asp Ile Leu Arg Glu Ser Leu Val
            100                 105                 110

Gly Leu Leu Ser Ser Val Ala Ser Pro Thr Ser Gln Phe Pro Ser Gly
        115                 120                 125

Val Phe Tyr Val Trp Ser Arg Glu Ser Arg Ile Ala Ala Leu Ile Asp
    130                 135                 140

Ser Leu Phe Gly Ala Leu Asp Ser Arg Asn
145                 150
```

<210> SEQ ID NO 15
<211> LENGTH: 162
<212> TYPE: PRT
<213> ORGANISM: Artificial Sequence
<220> FEATURE:
<223> OTHER INFORMATION: Synthetic

<400> SEQUENCE: 15

```
Met Lys Arg Asn Asp Asp Ala Ser Thr Ala Ala His Asn Asp Ile Pro
1               5                   10                  15

Gln Ile Leu Ser Ala Leu Asn Glu Gly Ala Gly Val Phe Asp Arg Ala
            20                  25                  30

Ser Phe Glu Ser Ala Phe Gly Leu Thr Trp Thr Asn Pro Asn Ala Asn
        35                  40                  45

Pro Asn Ala Asn Pro Asn Ala Asn Pro Asn Ala Asn Pro Asn Ala Asn
    50                  55                  60

Pro Asn Ala Asn Pro Asn Ala Ser Tyr Ser Thr Ser Gly Ile Arg Ser
65                  70                  75                  80

Leu Pro Ala Phe Ser Lys Ser Phe Phe Pro Tyr Leu Glu Leu Tyr Asn
                85                  90                  95

Leu Leu Ile Thr Asn Gln Gly Ala Ala Leu Gln Thr Gln Asn Gly Lys
            100                 105                 110

Asp Ile Leu Arg Glu Ser Leu Val Gly Leu Leu Ser Ser Val Ala Ser
        115                 120                 125

Pro Thr Ser Gln Phe Pro Ser Gly Val Phe Tyr Val Trp Ser Arg Glu
    130                 135                 140

Ser Arg Ile Ala Ala Leu Ile Asp Ser Leu Phe Gly Ala Leu Asp Ser
145                 150                 155                 160

Arg Asn
```

<210> SEQ ID NO 16
<211> LENGTH: 160
<212> TYPE: PRT
<213> ORGANISM: Artificial Sequence
<220> FEATURE:
<223> OTHER INFORMATION: Synthetic

<400> SEQUENCE: 16

```
Met Lys Arg Asn Asp Asp Ala Ser Thr Ala Ala His Asn Asp Ile Pro
1               5                   10                  15

Gln Ile Leu Ser Ala Leu Asn Glu Gly Ala Gly Val Phe Asp Arg Ala
            20                  25                  30

Ser Phe Glu Ser Ala Phe Gly Leu Thr Trp Thr Met Lys Glu Ile Glu
        35                  40                  45

Arg Glu Ser Lys Arg Ile Lys Leu Asn Asp Asn Asp Asp Glu Gly Asn
    50                  55                  60

Lys Lys Ile Ile Ala Ser Tyr Ser Thr Ser Gly Ile Arg Ser Leu Pro
65                  70                  75                  80

Ala Phe Ser Lys Ser Phe Phe Pro Tyr Leu Glu Leu Tyr Asn Leu Leu
                85                  90                  95

Ile Thr Asn Gln Gly Ala Ala Leu Gln Thr Gln Asn Gly Lys Asp Ile
            100                 105                 110

Leu Arg Glu Ser Leu Val Gly Leu Leu Ser Ser Val Ala Ser Pro Thr
        115                 120                 125

Ser Gln Phe Pro Ser Gly Val Phe Tyr Val Trp Ser Arg Glu Ser Arg
    130                 135                 140
```

```
Ile Ala Ala Leu Ile Asp Ser Leu Phe Gly Ala Leu Asp Ser Arg Asn
145                 150                 155                 160


<210> SEQ ID NO 17
<211> LENGTH: 178
<212> TYPE: PRT
<213> ORGANISM: Artificial Sequence
<220> FEATURE:
<223> OTHER INFORMATION: Synthetic

<400> SEQUENCE: 17

Met Lys Arg Asn Asp Asp Ala Ser Thr Ala Ala His Asn Asp Ile Pro
1               5                   10                  15

Gln Ile Leu Ser Ala Leu Asn Glu Gly Ala Gly Val Phe Asp Arg Ala
            20                  25                  30

Ser Phe Glu Ser Ala Phe Gly Leu Thr Trp Ser Asp Gln Pro Lys Gln
        35                  40                  45

Tyr Glu Gln His Leu Thr Asp Tyr Glu Lys Ile Lys Glu Gly Phe Lys
    50                  55                  60

Asn Lys Asn Ala Ser Met Ile Lys Ser Ala Phe Leu Pro Thr Gly Ala
65                  70                  75                  80

Phe Lys Ala Asp Arg Tyr Gly Ser Tyr Ser Thr Ser Gly Ile Arg Ser
                85                  90                  95

Leu Pro Ala Phe Ser Lys Ser Phe Phe Pro Tyr Leu Glu Leu Tyr Asn
            100                 105                 110

Leu Leu Ile Thr Asn Gln Gly Ala Ala Leu Gln Thr Gln Asn Gly Lys
        115                 120                 125

Asp Ile Leu Arg Glu Ser Leu Val Gly Leu Leu Ser Ser Val Ala Ser
    130                 135                 140

Pro Thr Ser Gln Phe Pro Ser Gly Val Phe Tyr Val Trp Ser Arg Glu
145                 150                 155                 160

Ser Arg Ile Ala Ala Leu Ile Asp Ser Leu Phe Gly Ala Leu Asp Ser
                165                 170                 175

Arg Asn


<210> SEQ ID NO 18
<211> LENGTH: 147
<212> TYPE: PRT
<213> ORGANISM: Artificial Sequence
<220> FEATURE:
<223> OTHER INFORMATION: Synthetic

<400> SEQUENCE: 18

Met Lys Arg Asn Asp Asp Ala Ser Thr Ala Ala His Asn Asp Ile Pro
1               5                   10                  15

Gln Ile Leu Ser Ala Leu Asn Glu Gly Ala Gly Val Phe Asp Arg Ala
            20                  25                  30

Ser Phe Glu Ser Ala Phe Gly Leu Thr Trp Thr Gly Ile Pro Asp Asn
        35                  40                  45

Asp Lys Asn Ser Asn Ser Lys Gly Ser Tyr Ser Thr Ser Gly Ile Arg
    50                  55                  60

Ser Leu Pro Ala Phe Ser Lys Ser Phe Phe Pro Tyr Leu Glu Leu Tyr
65                  70                  75                  80

Asn Leu Leu Ile Thr Asn Gln Gly Ala Ala Leu Gln Thr Gln Asn Gly
                85                  90                  95

Lys Asp Ile Leu Arg Glu Ser Leu Val Gly Leu Leu Ser Ser Val Ala
            100                 105                 110
```

-continued

```
Ser Pro Thr Ser Gln Phe Pro Ser Gly Val Phe Tyr Val Trp Ser Arg
        115                 120                 125

Glu Ser Arg Ile Ala Ala Leu Ile Asp Ser Leu Phe Gly Ala Leu Asp
    130                 135                 140

Ser Arg Asn
145


<210> SEQ ID NO 19
<211> LENGTH: 165
<212> TYPE: PRT
<213> ORGANISM: Artificial Sequence
<220> FEATURE:
<223> OTHER INFORMATION: Synthetic

<400> SEQUENCE: 19

Met His His His His His His Thr Arg Arg Val Asp Asp Ala Thr Val
1               5                   10                  15

Ala Ile Arg Ser Ala Ile Asn Asn Leu Ile Val Glu Leu Ile Arg Gly
            20                  25                  30

Thr Gly Ser Tyr Asn Arg Ser Ser Phe Glu Ser Ser Ser Gly Leu Val
        35                  40                  45

Trp Thr Ser Asp Asn Pro Asn Ala Asn Pro Asn Ala Asn Pro Asn Ala
    50                  55                  60

Asn Pro Asn Ala Asn Pro Asn Ala Glu Gly Ser Tyr Ser Ile Thr Thr
65                  70                  75                  80

Pro Ser Gln Phe Val Phe Leu Ser Ser Ala Trp Ala Asp Pro Ile Glu
                85                  90                  95

Leu Ile Asn Leu Cys Thr Asn Ala Leu Gly Asn Gln Phe Gln Thr Gln
            100                 105                 110

Gln Ala Arg Thr Val Val Gln Arg Gln Phe Ser Glu Val Trp Lys Pro
        115                 120                 125

Ser Pro Gln Val Thr Val Arg Phe Pro Asp Ser Asp Phe Lys Val Tyr
    130                 135                 140

Arg Tyr Asn Ala Val Leu Asp Pro Leu Val Thr Ala Leu Leu Gly Ala
145                 150                 155                 160

Phe Asp Thr Arg Asn
                165


<210> SEQ ID NO 20
<211> LENGTH: 167
<212> TYPE: PRT
<213> ORGANISM: Artificial Sequence
<220> FEATURE:
<223> OTHER INFORMATION: Synthetic

<400> SEQUENCE: 20

Met His His His His His His Asp Ala Thr Arg Arg Val Asp Asp Ala
1               5                   10                  15

Thr Val Ala Ile Arg Ser Ala Ile Asn Asn Leu Ile Val Glu Leu Ile
            20                  25                  30

Arg Gly Thr Gly Ser Tyr Asn Arg Ser Ser Phe Glu Ser Ser Ser Gly
        35                  40                  45

Leu Val Trp Thr Asn Pro Asn Ala Asn Pro Asn Ala Asn Pro Asn Ala
    50                  55                  60

Asn Pro Asn Ala Asn Pro Asn Ala Ser Tyr Ser Ile Thr Thr Pro Ser
65                  70                  75                  80

Gln Phe Val Phe Leu Ser Ser Ala Trp Ala Asp Pro Ile Glu Leu Ile
                85                  90                  95
```

```
Asn Leu Cys Thr Asn Ala Leu Gly Asn Gln Phe Gln Thr Gln Gln Ala
            100                 105                 110

Arg Thr Val Val Gln Arg Gln Phe Ser Glu Val Trp Lys Pro Ser Pro
        115                 120                 125

Gln Val Thr Val Arg Phe Pro Asp Ser Asp Phe Lys Val Tyr Arg Tyr
    130                 135                 140

Asn Ala Val Leu Asp Pro Leu Val Thr Ala Leu Leu Gly Ala Phe Asp
145                 150                 155                 160

Thr Arg Asn Arg Ile Ile Glu
                165


<210> SEQ ID NO 21
<211> LENGTH: 146
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (53)..(53)
<223> OTHER INFORMATION: X at position 53 denotes placeholder for
      location of insertion of immunogenic epitopes of interest.

<400> SEQUENCE: 21

Met His His His His His His Thr Arg Arg Val Asp Asp Ala Thr Val
1               5                   10                  15

Ala Ile Arg Ser Ala Ile Asn Asn Leu Ile Val Glu Leu Ile Arg Gly
            20                  25                  30

Thr Gly Ser Tyr Asn Arg Ser Ser Phe Glu Ser Ser Ser Gly Leu Val
        35                  40                  45

Trp Thr Ser Asp Xaa Glu Gly Ser Tyr Ser Ile Thr Thr Pro Ser Gln
    50                  55                  60

Phe Val Phe Leu Ser Ser Ala Trp Ala Asp Pro Ile Glu Leu Ile Asn
65                  70                  75                  80

Leu Cys Thr Asn Ala Leu Gly Asn Gln Phe Gln Thr Gln Gln Ala Arg
                85                  90                  95

Thr Val Val Gln Arg Gln Phe Ser Glu Val Trp Lys Pro Ser Pro Gln
            100                 105                 110

Val Thr Val Arg Phe Pro Asp Ser Asp Phe Lys Val Tyr Arg Tyr Asn
        115                 120                 125

Ala Val Leu Asp Pro Leu Val Thr Ala Leu Leu Gly Ala Phe Asp Thr
    130                 135                 140

Arg Asn
145


<210> SEQ ID NO 22
<211> LENGTH: 148
<212> TYPE: PRT
<213> ORGANISM: Artificial Sequence
<220> FEATURE:
<223> OTHER INFORMATION: Synthetic
<220> FEATURE:
<221> NAME/KEY: misc_features
<222> LOCATION: (53)..(53)
<223> OTHER INFORMATION: X at position 53 denotes placeholder for
      location of insertion of immunogenic epitopes of interest.

<400> SEQUENCE: 22

Met His His His His His His Asp Ala Thr Arg Arg Val Asp Asp Ala
1               5                   10                  15
```

Thr Val Ala Ile Arg Ser Ala Ile Asn Asn Leu Ile Val Glu Leu Ile
20 25 30

Arg Gly Thr Gly Ser Tyr Asn Arg Ser Ser Phe Glu Ser Ser Ser Gly
35 40 45

Leu Val Trp Thr Xaa Ser Tyr Ser Ile Thr Thr Pro Ser Gln Phe Val
50 55 60

Phe Leu Ser Ser Ala Trp Ala Asp Pro Ile Glu Leu Ile Asn Leu Cys
65 70 75 80

Thr Asn Ala Leu Gly Asn Gln Phe Gln Thr Gln Gln Ala Arg Thr Val
85 90 95

Val Gln Arg Gln Phe Ser Glu Val Trp Lys Pro Ser Pro Gln Val Thr
100 105 110

Val Arg Phe Pro Asp Ser Asp Phe Lys Val Tyr Arg Tyr Asn Ala Val
115 120 125

Leu Asp Pro Leu Val Thr Ala Leu Leu Gly Ala Phe Asp Thr Arg Asn
130 135 140

Arg Ile Ile Glu
145

<210> SEQ ID NO 23
<211> LENGTH: 179
<212> TYPE: PRT
<213> ORGANISM: Artificial Sequence
<220> FEATURE:
<223> OTHER INFORMATION: Synthetic

<400> SEQUENCE: 23

Met Lys Arg Asn Asp Asp Ala Ser Thr Ala Ala His Asn Asp Ile Pro
1 5 10 15

Gln Ile Leu Ser Ala Leu Asn Glu Gly Ala Gly Val Phe Asp Arg Ala
20 25 30

Ser Phe Glu Ser Ala Phe Gly Leu Thr Trp Thr Gly Asp Arg Ala Asp
35 40 45

Gly Gln Pro Ala Gly Asp Arg Ala Ala Gly Gln Pro Ala Gly Asp Arg
50 55 60

Ala Asp Gly Gln Pro Ala Gly Asp Arg Ala Ala Gly Gln Pro Ala Gly
65 70 75 80

Asp Arg Ala Asp Gly Gln Pro Ala Ser Tyr Ser Thr Ser Gly Ile Arg
85 90 95

Ser Leu Pro Ala Phe Ser Lys Ser Phe Phe Pro Tyr Leu Glu Leu Tyr
100 105 110

Asn Leu Leu Ile Thr Asn Gln Gly Ala Ala Leu Gln Thr Gln Asn Gly
115 120 125

Lys Asp Ile Leu Arg Glu Ser Leu Val Gly Leu Leu Ser Ser Val Ala
130 135 140

Ser Pro Thr Ser Gln Phe Pro Ser Gly Val Phe Tyr Val Trp Ser Arg
145 150 155 160

Glu Ser Arg Ile Ala Ala Leu Ile Asp Ser Leu Phe Gly Ala Leu Asp
165 170 175

Ser Arg Asn

<210> SEQ ID NO 24
<211> LENGTH: 160
<212> TYPE: PRT
<213> ORGANISM: Artificial Sequence
<220> FEATURE:
<223> OTHER INFORMATION: Synthetic

<400> SEQUENCE: 24

Met Lys Arg Asn Asp Asp Ala Ser Thr Ala Ala His Asn Asp Ile Pro
1 5 10 15

Gln Ile Leu Ser Ala Leu Asn Glu Gly Ala Gly Val Phe Asp Arg Ala
20 25 30

Ser Phe Glu Ser Ala Phe Gly Leu Thr Trp Thr Gly Asn Gln Pro Gly
35 40 45

Ala Asn Gly Ala Gly Asn Gln Pro Gly Ala Asn Gly Ala Gly Asn Gln
50 55 60

Pro Gly Ala Asn Gly Ser Tyr Ser Thr Ser Gly Ile Arg Ser Leu Pro
65 70 75 80

Ala Phe Ser Lys Ser Phe Phe Pro Tyr Leu Glu Leu Tyr Asn Leu Leu
85 90 95

Ile Thr Asn Gln Gly Ala Ala Leu Gln Thr Gln Asn Gly Lys Asp Ile
100 105 110

Leu Arg Glu Ser Leu Val Gly Leu Leu Ser Ser Val Ala Ser Pro Thr
115 120 125

Ser Gln Phe Pro Ser Gly Val Phe Tyr Val Trp Ser Arg Glu Ser Arg
130 135 140

Ile Ala Ala Leu Ile Asp Ser Leu Phe Gly Ala Leu Asp Ser Arg Asn
145 150 155 160

<210> SEQ ID NO 25
<211> LENGTH: 194
<212> TYPE: PRT
<213> ORGANISM: Artificial Sequence
<220> FEATURE:
<223> OTHER INFORMATION: Synthetic

<400> SEQUENCE: 25

Met His His His His His His Thr Arg Arg Val Asp Asp Ala Thr Val
1 5 10 15

Ala Ile Arg Ser Ala Ile Asn Asn Leu Ile Val Glu Leu Ile Arg Gly
20 25 30

Thr Gly Ser Tyr Asn Arg Ser Ser Phe Glu Ser Ser Ser Gly Leu Val
35 40 45

Trp Thr Gly Asn Gln Pro Gly Ala Asn Gly Ala Gly Asp Gln Pro Gly
50 55 60

Ala Asn Gly Ala Gly Asn Gln Pro Gly Ala Asn Gly Ala Gly Asn Gln
65 70 75 80

Pro Gly Ala Asn Gly Ala Gly Asn Gln Pro Gly Ala Asn Gly Ala Gly
85 90 95

Asn Gln Pro Gly Ala Asn Gly Ser Tyr Ser Ile Thr Thr Pro Ser Gln
100 105 110

Phe Val Phe Leu Ser Ser Ala Trp Ala Asp Pro Ile Glu Leu Ile Asn
115 120 125

Leu Cys Thr Asn Ala Leu Gly Asn Gln Phe Gln Thr Gln Gln Ala Arg
130 135 140

Thr Val Val Gln Arg Gln Phe Ser Glu Val Trp Lys Pro Ser Pro Gln
145 150 155 160

-continued

```
Val Thr Val Arg Phe Pro Asp Ser Asp Phe Lys Val Tyr Arg Tyr Asn
                165                 170                 175

Ala Val Leu Asp Pro Leu Val Thr Ala Leu Leu Gly Ala Phe Asp Thr
            180                 185                 190

Arg Asn
```